US011361527B2

(12) United States Patent
Finkbeiner et al.

(10) Patent No.: US 11,361,527 B2
(45) Date of Patent: *Jun. 14, 2022

(54) AUTOMATED ROBOTIC MICROSCOPY SYSTEMS

(71) Applicant: The J. David Gladstone Institutes, a testamentary trust established under the Will of J. David Gladstone, San Francisco, CA (US)

(72) Inventors: Steven M. Finkbeiner, Corte Madera, CA (US); Dale Michael Ando, San Francisco, CA (US); Aaron C. Daub, San Francisco, CA (US)

(73) Assignee: The J. David Gladstone Institutes, San Francisco, CA (US), a testamentary trust established under the Will of J. David Gladstone ( * ) Notice: Subject to any disclaimer, the term of this patent is extended or adjusted under 35 U.S.C. 154(b) by 0 days.

This patent is subject to a terminal disclaimer.

(21) Appl. No.: 16/584,494

(22) Filed: Sep. 26, 2019

(65) Prior Publication Data

US 2020/0089986 A1 Mar. 19, 2020

Related U.S. Application Data

(63) Continuation of application No. 14/737,325, filed on Jun. 11, 2015, now Pat. No. 10,474,920, which is a
(Continued)

(51) Int. Cl.
*G02B 21/34* (2006.01)
*G06V 10/24* (2022.01)
(Continued)

(52) U.S. Cl.
CPC ......... *G06V 10/245* (2022.01); *G01N 21/253* (2013.01); *G01N 35/0099* (2013.01);
(Continued)

(58) Field of Classification Search
None
See application file for complete search history.

(56) References Cited

U.S. PATENT DOCUMENTS

| 4,000,417 A | 12/1976 | Adkisson et al. |
| 4,012,112 A | 3/1977 | Masterson |
(Continued)

FOREIGN PATENT DOCUMENTS

| CA | 2893590 | 6/2014 |
| EP | 2439576 | 4/2012 |
(Continued)

OTHER PUBLICATIONS

Arrasate M., et al., "Prospective Analysis of Huntingtin Conformation and Degeneration in Neurons," *Gladstone Inst Neurological Diseases*, Departments of Neurology and Physiology, University of California, San Francisco, CA USA; Aug. 5, 2002; p. 26.
(Continued)

*Primary Examiner* — Christopher G Findley
(74) *Attorney, Agent, or Firm* — Schwegman Lundberg & Woessner, P.A.

(57) ABSTRACT

The present disclosure provides automated robotic microscopy systems that facilitate high throughput and high content analysis of biological samples, such as living cells and/or tissues. In certain aspects, the systems are configured to reduce user intervention relative to existing technologies, and allow for precise return to and re-imaging of the same field (e.g., the same cell) that has been previously imaged. This capability enables experiments and testing of hypotheses that deal with causality over time with greater precision and throughput than conventional microscopy methods.

37 Claims, 32 Drawing Sheets

Related U.S. Application Data continuation-in-part of application No. PCT/US2013/075045, filed on Dec. 13, 2013.

(60) Provisional application No. 61/737,683, filed on Dec. 14, 2012.

(51) Int. Cl.

| | |
|---|---|
| *G02B 21/36* | (2006.01) |
| *G02B 21/26* | (2006.01) |
| *G02B 27/32* | (2006.01) |
| *G02B 21/00* | (2006.01) |
| *G06V 20/69* | (2022.01) |
| *G01N 21/25* | (2006.01) |
| *G01N 35/00* | (2006.01) |
| *C12M 1/34* | (2006.01) |

(52) U.S. Cl.
CPC ......... *G02B 21/0088* (2013.01); *G02B 21/26* (2013.01); *G02B 21/365* (2013.01); *G02B 27/32* (2013.01); *G06V 20/693* (2022.01); *C12M 41/36* (2013.01); *G02B 21/34* (2013.01)

(56) References Cited

U.S. PATENT DOCUMENTS

| | | | |
|---|---|---|---|
| 4,232,970 A | 11/1980 | Sawamura et al. | |
| 4,513,438 A | 4/1985 | Graham et al. | |
| 4,705,949 A | 11/1987 | Grimes, II et al. | |
| 4,810,869 A | 3/1989 | Yabe et al. | |
| 4,833,382 A | 5/1989 | Gibbs | |
| 4,920,053 A | 4/1990 | Inoue et al. | |
| 4,958,920 A | 9/1990 | Jorgens et al. | |
| 4,974,952 A | 12/1990 | Focht | |
| 5,000,554 A | 3/1991 | Gibbs | |
| 5,073,857 A | 12/1991 | Peters et al. | |
| 5,109,429 A | 4/1992 | Bacus et al. | |
| 5,231,279 A | 7/1993 | Namamura | |
| 5,473,706 A | 12/1995 | Bacus et al. | |
| 5,480,804 A | 1/1996 | Niwa et al. | |
| 5,574,594 A | 1/1996 | Fowler et al. | |
| 5,539,521 A | 7/1996 | Otokake et al. | |
| 5,594,235 A | 1/1997 | Lee | |
| 5,861,985 A | 1/1999 | Ikoh | |
| 5,991,028 A | 11/1999 | Cabib et al. | |
| 6,005,964 A | 12/1999 | Reid et al. | |
| 6,049,421 A | 4/2000 | Raz et al. | |
| 6,128,129 A | 10/2000 | Yoneyama | |
| 6,130,745 A | 10/2000 | Manian et al. | |
| 6,150,173 A | 11/2000 | Schubert | |
| 6,151,161 A | 11/2000 | Mayer et al. | |
| 6,160,662 A | 12/2000 | Uchida et al. | |
| 6,175,642 B1 | 1/2001 | Gobbi et al. | |
| 6,204,962 B1 | 3/2001 | Kawamura | |
| 6,226,392 B1 | 5/2001 | Bacus et al. | |
| 6,246,785 B1 | 6/2001 | Molnar et al. | |
| 6,285,498 B1 | 9/2001 | Mayer | |
| 6,319,668 B1 | 11/2001 | Nova et al. | |
| 6,483,948 B1 | 11/2002 | Spink et al. | |
| 6,517,781 B1 | 2/2003 | Coassin et al. | |
| 6,818,403 B2 | 11/2004 | Kirk et al. | |
| 6,986,993 B1 | 1/2006 | Ghosh et al. | |
| 7,006,674 B1 | 2/2006 | Zahniser et al. | |
| 7,139,415 B2 | 11/2006 | Finkbeiner | |
| 10,474,920 B2 * | 11/2019 | Finkbeiner ............ | G02B 27/32 |
| 2001/0033414 A1 | 10/2001 | Kanji | |
| 2002/0053244 A1 | 5/2002 | Goenner et al. | |
| 2002/0101654 A1 | 8/2002 | Pfeifer | |
| 2003/0017085 A1 | 1/2003 | Kercso et al. | |
| 2003/0103662 A1 | 6/2003 | Finkbeiner | |
| 2004/0013576 A1 | 1/2004 | Gfrorer et al. | |
| 2005/0213090 A1 | 9/2005 | Namba et al. | |
| 2006/0115182 A1 | 6/2006 | Deng et al. | |
| 2007/0153369 A1 | 7/2007 | Schutze et al. | |
| 2009/0180684 A1 | 7/2009 | Tani | |
| 2010/0129789 A1 * | 5/2010 | Self ........................ | B01L 9/06 |
| | | | 435/5 |
| 2010/0209957 A1 | 8/2010 | Hogan et al. | |
| 2011/0188726 A1 | 8/2011 | Nathaniel et al. | |
| 2011/0267448 A1 | 11/2011 | Thomas | |
| 2013/0078149 A1 * | 3/2013 | Holmes ................ | G01N 1/4077 |
| | | | 422/72 |
| 2013/0128035 A1 | 5/2013 | Johns et al. | |
| 2013/0315802 A1 | 11/2013 | Manian et al. | |
| 2014/0171829 A1 * | 6/2014 | Holmes ................ | B01L 3/5082 |
| | | | 600/575 |
| 2015/0278625 A1 | 10/2015 | Finkbeiner et al. | |

FOREIGN PATENT DOCUMENTS

| | | |
|---|---|---|
| EP | 2932425 | 10/2015 |
| JP | 2001299379 | 10/2001 |
| JP | 2003513251 | 4/2003 |
| JP | 2004517341 | 6/2004 |
| JP | 2005514589 | 5/2005 |
| JP | 2011128019 | 6/2011 |
| JP | 2012177805 | 9/2012 |
| JP | 2012529048 | 11/2012 |
| JP | 6373864 | 12/2013 |
| JP | 2014514580 | 6/2014 |
| JP | 2016501534 | 1/2016 |
| WO | WO 2001011340 | 2/2001 |
| WO | WO 200131566 | 5/2001 |
| WO | WO 2001042796 | 6/2001 |
| WO | WO 2010022391 | 2/2010 |
| WO | 2014093838 | 6/2014 |
| WO | 2014093838 | 7/2015 |

OTHER PUBLICATIONS

Bahlmann K., et al., "4Pi-confocal Microscopy of Live Cells," *Ultamircoscopy*, 87; (2001) pp. 155-164.

Berg, RH (2004) "Evaluation of spectral imaging for plant cell analysis"; Journal of Microscopy 214; pp. 174-181.

Bradley J, et al., "An Evaluation of Specificity In Activity-Department Gene Expression in Neurons," *Progress in Neurobiology 67*; (2002) pp. 469-477.

Chen, Y. et al. (2007) "Characterization of spectral FRET imaging microscopy for monitoring nuclear protein interactions"; Journal of Microscopy 22.8; pp. 139-152.

Dickinson, et al (2003) "Multiphoton excitation spectra in biological samples"; Journal of Biomedical Optics 8; pp. 329-338.

Fiji; "Image Stitching"; Retrieved from http://fiji.sc/wiki/index.php/Image_Stitching; last modified on Jul. 16, 2012; 9 pages.

Finkbeiner R., "Robotic Microscope Monitors Gradual Cell Changes"; *Biophotonics International*; Jul./Aug. 2002,p. 15.

Finkbeiner R., "New Roles for Introns: Sites of Combinatorial Regulation of $Ca^{2+}$- and Cyclic AMP-Dependent Gene Transcription," *Science's stke*; www.stke.org/cgi/content/full/OC_sigtrans;2001/94/pe1: Aug. 7, 2001; pp. 1-4.

Finkbeiner R., "Calcium Regulation of the Brain-Derived Neurotrophic Factor Gene"; *CMLS, Cell. Mod. Life Sci.* 57; (2000) pp. 394-401.

Finkbeiner R., "CREB Couples Neurotrophin Signals to Survival Messages"; *Neuron*, vol. 25, 11-14; (Jan. 2000), Copyright © 2000 by Cell Press; pp. 11-14.

Friedman R., "Is Neurodogeneration a Misnomer?" *BioMedNet News and Comments*, Nov. 15, 2001; pp. 1-2; http://news/story?day=011115&story=2.

Garini, et al (2006) "Spectral imaging: principles and applications"; Cytometry A 69; pp. 735-747.

Guy R, et al., "A Fluorescence Microscopy Based Genetic Screen to Identify Mutants Altered for Interactions with Host Cells"; *J Microbiol Methods*42(2); (Oct. 2000); pp. 129-138.

Hiraoka, et al (2002) "Multiphoton excitation spectra in biological samples"; Cell Structure and Function 27; pp. 367-374.

Humbert S., et al., "The IGF-1/Akt Pathway is Neuroprotective in Huntington's Disease and Involves Huntingtin Phosphorylation By Akt"; *Development Cell* 2(6); (Jun. 2002) pp. 831-837.

(56) References Cited

OTHER PUBLICATIONS

Kam Z., et al, "Probing Molecular Processes in Live Cells by Quantitative Multidimensional Microscopy"; *Trends Cell Biol* 11(8); (Aug. 2001) pp. 329-334.

Kobatake Hidefumi (2001) "Morphology for Three Dimensional image processing"; Medical Imaging Technology vol. 19 No. 1; 7 pages.

Lansford, et al (2001) "Resolution of multiple green fluorescent protein color variants and dyes using two-photon microscopy and imaging spectroscopy"; Journal of Biomedical Optics 6; pp. 311-318.

Lerner JM and Zucker RM (2004) "Calibration and validation of confocal spectral imaging systems"; Cytometry A 62; pp. 8-34.

Levnson, RM and Mansfield, Jr (2006) "Multispectral imaging in biology and medicine: slices of life"; Cytometry A 69; pp. 748-758.

Lowe, David G. (2004) "Distinctive Image Features from Scale-Invariant Keypoints"; International Journal of Computer Vision, vol. 60, No. 2; pp. 91-110.

Medlin J., "New Microscope Gives Scientists The Inside Scoop on Living Cells," *Environmental Health Perspectives* vol. 107, No. 11, (Nov. 1999); pp. A566-A568.

Megias, D., et al (2009) "Novel lambda FRET spectral confocal microscopy imaging method"; Microscopy Research and Technique 72; pp. 1-11.

Neher, RA and Neher, E (2003) "Optimizing imaging parameters for the separation of multiple labels in a fluorescence image"; Journal of Microscopy 213; pp. 46-62.

Reynaud K, et al., "Confocal Microscopy: Principles and Applications to the Field of Reproductive Biology," *Folia Histochem Cytobiol* 39(2); (2001); pp. 75-85.

Saudou F. et al., "Huntingtin Acts in the Nucleus to Induce Apoptosis But Death Does Not Correlate With The Formation of Intranuclear Inclusions," *Cell* 95(1); Oct. 21, 1998; pp. 55-66.

Spriet C., et al (2007) "Correlated fluorescence lifetime and spectral measurements in living cells"; Microscopy Research and Technique 70: 85-94.

Thaler, et al (2005) "Quantitative multiphoton spectral imaging and its use for measuring resonance energy transfer"; Biophysical Journal 89; pp. 2736-2749.

Thevenaz, et al; "StackReg—An ImageJ plugin for the recursive alignment of a stack of images"; *Biomedical Imaging Group*; (2012); 2 pages.

Thevenaz, et al; "A Pyramid Approach to Subpixel Registration Based on Intensity"; *IEEE Transactions on Image Processing*, vol. 7, No. 1; Jan. 1998; pp. 27-41.

Ward GE, et al., "96-Well Plates Providing High Optical Resolution for High-Throughput, Immunofluorescence-Based Screening of Monoclonal Antibodies Against Toxoplasma Gondii,"; *J Immunol Methods*230(1-2); Nov. 19, 1999; pp. 11-18.

Ziauddin et al., entitled "Microarrays of Cells Expressing Defined cDNAs," *Nature*, vol. 411, May 3, 2001, www.nature.com.

Zimmerman, et al (2003) "Spectral imaging and its applications in live cell microscopy"; FEBS Letters. 546(1); pp. 87-92.

Zimmerman (2005) "Spectral imaging and linear unmixing in light microscopy"; Advances in Biochemical Engineering/Biotechnology 95; pp. 245-265.

"European Application Serial No. 13862299.8, Communication Pursuant to Article 94(3) EPC dated Jan. 8, 2020", 7 pgs.

"European Application Serial No. 13862299.8, Response filed Feb. 1, 2016 to Communication Pursuant to Rules 161(1) and 162 EPC dated Jul. 24, 2015", 4 pgs.

"European Application Serial No. 13862299.8, Partial Supplementary European Search Report dated Jun. 30, 2016", 8 pgs.

"European Application Serial No. 13862299.8, Extended European Search Report dated Nov. 17, 2016", 14 pgs.

"European Application Serial No. 13862299.8, Response filed Aug. 16, 2017 to Extended European Search Report dated Nov. 17, 2016", 56 pgs.

"Canadian Application Serial No. 2,893,590, Office Action dated Jan. 24, 2020", 3 pgs.

"U.S. Appl. No. 14/737,325, Preliminary Amendment filed Oct. 22, 2015", 8 pgs.

"U.S. Appl. No. 14/737,325, Non Final Office Action dated May 18, 2017", 12 pgs.

"U.S. Appl. No. 14/737,325, Response filed Aug. 9, 2017 to Non Final Office Action dated May 18, 2017", 17 pgs.

"U.S. Appl. No. 14/737,325, Final Office Action dated Dec. 15, 2017", 15 pgs.

"U.S. Appl. No. 14/737,325, Response filed Mar. 1, 2018 to Final Office Action dated Dec. 15, 2017", 17 pgs.

"U.S. Appl. No. 14/737,325, Advisory Action dated Apr. 10, 2018", 3 pgs.

"U.S. Appl. No. 14/737,325, Non Final Office Action dated Jul. 11, 2018", 14 pgs.

"U.S. Appl. No. 14/737,325, Response filed Oct. 8, 2018 to Non Final Office Action dated Jul. 11, 2018", 16 pgs.

"U.S. Appl. No. 14/737,325, Final Office Action dated Feb. 8, 2019", 14 pgs.

"U.S. Appl. No. 14/737,325, Response filed Apr. 5, 2019 to Final Office Action dated Feb. 8, 2019", 19 pgs.

"U.S. Appl. No. 14/737,325, Advisory Action dated Apr. 29, 2019", 3 pgs.

"U.S. Appl. No. 14/737,325, Notice of Allowance dated Jun. 28, 2019", 8 pgs.

"International Application Serial No. PCT US2013 075045, International Search Report dated Jun. 10, 2014", 4 pgs.

"International Application Serial No. PCT US2013 075045, Written Opinion dated Jun. 10, 2014", 8 pgs.

"International Application Serial No. PCT US2013 075045, International Preliminary Report on Patentability dated Jun. 25, 2015", 10 pgs.

"Japanese Application Serial No. 2015-547991, Amendment filed Dec. 7, 2016", W English Translation, 14 pgs.

"Japanese Application Serial No. 2015-547991, Notice of Reason for Rejection dated Dec. 12, 2017", W English Translation, 8 pgs.

"Japanese Application Serial No. 2015-547991, Response filed Mar. 7, 2018 to Notice of Reason for Rejection dated Dec. 12, 2017", W English Translation, 22 pgs.

"Canadian Application Serial No. 2,893,590, Response filed May 20, 2020 to Office Action dated Jan. 24, 2020", 103 pgs.

Kobata, Hidefumi, "3 dimensional image and morphology", Medical Imaging Technology, Japan, 19, 3 (with English abstract), (May 2001), 168-173.

"Canadian Application Serial No. 2,893,590, Office Action dated Nov. 2, 2020", 4 pgs.

"Canadian Application Serial No. 2,893,590, Response filed Mar. 2, 2021 to Office Action dated Nov. 2, 2020", 113 pgs.

"European Application Serial No. 13862299.8, Communication Pursuant to Article 94(3) EPC dated Nov. 5, 2020", 5 pgs.

"Canadian Application Serial No. 2,893,590, Office Action dated Jun. 11, 2021", 4 pgs.

"Canadian Application Serial No. 2,893,590, Response filed Oct. 12, 2021 to Office Action dated Jun. 11, 2021", 4 pgs.

"Canadian Application Serial No. 2893590, Office Action dated Feb. 11, 2022", 4 pgs.

\* cited by examiner

C

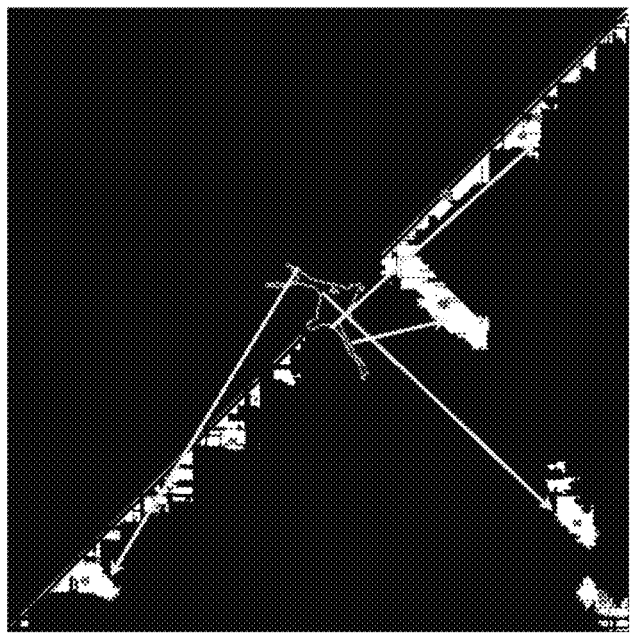
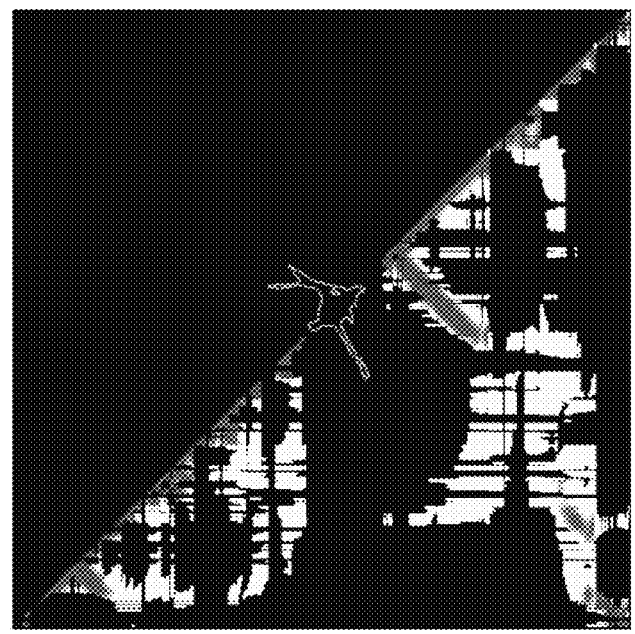
FIG. 26 (Continued)

E

AUTOMATED ROBOTIC MICROSCOPY SYSTEMS

CROSS-REFERENCE

This application is a continuation of U.S. application Ser. No. 14/737,325, filed Jun. 11, 2015, now U.S. Pat. No. 10,474,920, which is a continuation-in-part of International Application No. PCT/US2013/075045, filed Dec. 13, 2013, which application claims the benefit of U.S. Provisional Application No. 61/737,683, filed Dec. 14, 2012, which applications are incorporated herein by reference in their entirety.

INTRODUCTION

Recent advances in microscopy have contributed to the analysis of samples and systems, including biological samples and systems, with improved efficiency. For example, inverted microscope configurations and computer control for automatic focusing and microscope stage positioning have been developed to facilitate the repeated imaging of biological samples. U.S. Pat. No. 4,000,417 describes a computer automated system that permits re-viewing of previously viewed cells on previously used slides. Further, U.S. Pat. No. 7,139,415 describes a robotic microscope system and methods that allow high through-put analysis of biological materials, particularly living cells, and precise return to and re-imaging of the same field (e.g., the same cell) over time.

SUMMARY

The present disclosure provides automated robotic microscopy systems that facilitate high throughput and high content analysis of samples, including biological samples such as living cells and/or tissues. In certain aspects, the systems are configured to reduce user intervention relative to existing technologies, and allow for precise return to and re-imaging of the same field (e.g., the same cell) that has been previously imaged. This capability enables experiments and testing of hypotheses that deal with causality over time with greater precision and throughput than existing technologies.

For example, embodiments of the subject systems provide a degree of throughput and analytic capability not possible with the systems described in U.S. Pat. Nos. 4,920,053; 5,991,028; 4,705,949; 5,594,235; 6,005,964; 5,861,985; 6,049,421; 6,246,785; 4,958,920; and 7,139,415; or the systems described in the publications: *Anal Biochem* 2001 Jun. 15; 293(2):258-63, *Ultramicroscopy* 2001, April; 87(3): 155-64, *Folia Histochem Cytobiol* 2001; 39(2):75-85, *Trends Cell Biol* 2001 August; 11(8): 329-34, *J Microbiol Methods* 2000 October; 42(2):129-38, *J Immunol Methods* 1999 Nov. 19; 230(1-2):11-8, *Environmental Health Perspective* 1999, November; 107(11), and *Nature* 2001 May; 411: 107-110; the disclosures of which are incorporated herein by reference.

In certain aspects, systems of the present disclosure include an imaging device including a sample holder; a transport device configured to place a sample in the sample holder; a processor in communication with the imaging device and the transport device; and memory operably coupled to the processor, wherein the memory includes instructions stored thereon for acquiring an image of the sample, wherein the instructions, when executed by the processor, cause the processor to: move the sample via the transport device to the sample holder of the imaging device; identify a fiduciary mark on the sample using the imaging device; move the sample holder so that the fiduciary mark is in substantially the same position as in a reference image; and acquire an image of the sample using the imaging device.

In other aspects, systems of the present disclosure include an imaging device and a robotic arm configured to automatically retrieve a sample from a first surface and place the sample on the imaging device, wherein the system is configured to automatically identify a fiduciary mark on the sample, move the sample so that the fiduciary mark is in substantially the same position as in a reference image, and acquire an image of the sample. The robotic arm may be configured to interact with a plurality of imaging devices (e.g., a system includes two imaging devices and one robotic arm).

Systems of the present disclosure may be used with a variety of sample types. In some aspects, a sample includes biological material, such as living cells (e.g., neurons) and/or tissues. Biological material may be obtained from an in vitro source (e.g., a suspension of cells from laboratory cells grown in culture) or from an in vivo source (e.g., a mammalian subject, a human subject, etc.). Samples of interest further include non-biological samples, such as those from chemical or synthetic sources. Samples may be present on a variety of different sample-containing means, such as plates, including multi-well plates of any convenient number, composition, color, and the like.

Systems of the present disclosure may include a bulk sample storage subsystem. In such systems, a transport device may be configured to move a sample from the bulk sample storage subsystem to the imaging device, such as to a sample holder of the imaging device. Such movement may be automated, such that the transport device is controlled by a processor programmed to control the transport device. The bulk sample storage subsystem itself may store one or more samples, such as 5 or more, including 20 or more, 40 or more, or 80 or more. The samples may be kept at desired conditions (e.g., a desired temperature, humidity, etc.) within the bulk sample storage subsystem. In certain aspects, such desired conditions may be user-defined and/or under closed-loop control. Aspects of embodiments of systems of the present disclosure include systems in which samples are stored under homogeneous or heterogeneous conditions, e.g., a first population of the samples are stored under first desired conditions, a second population of the samples are stored under second desired conditions, etc. In such embodiments in which the samples are stored under heterogeneous conditions, the first, second, etc. conditions may differ from one another by one or more properties, such as temperature, humidity, and the like.

Transport devices used in systems of the present disclosure may vary greatly. In certain aspects, a transport device is a robotic arm. Robotic arms of interest may include one or more sample engagement elements, such as grippers, which facilitate the acquisition or transport of a sample. In certain embodiments, grippers may exert a lateral pressure on a sample, and may be adjustable so as to engage samples of different sizes. Aspects include systems comprising a plurality of transport devices, including 2 or more, such as 2 to 4, 4 to 6, 6 to 10, or 10 to 15. In such embodiments, the transport devices may be identical (e.g., all transport devices are the same model of robotic arm) or different (e.g., different types of transport devices, different models of similar transport devices such as robotic arms, etc.).

In certain aspects, systems of the present disclosure may include one or more elements for identifying a particular sample, such as a sample identification subsystem. Any convenient means for identifying a sample may be employed, such as a barcode, QR code, and the like. The handling, imaging, or image processing of an identified sample may each be tailored for a particular sample. For example, where samples are present on multi-well plates, the handling, imaging, and/or image processing of each well of the multi-well plate may be tailored for that particular well.

A variety of imaging devices may be employed in systems of the present disclosure, such as imaging devices that include an inverted microscope body. Imaging devices of interest include, but are not limited to, imaging devices in which acquiring an image of a sample includes deconvolving a multi-wavelength image into its component wavelengths and/or obtaining 3-dimensional pixel intensities. A number of components may be included in an imaging device, such as a camera (e.g., an EMCCD camera), light source (e.g., a Xenon light source with light guide), filters, automated focusing components, and the like, as is described herein. Systems of interest include, but are not limited to, systems comprising 2 or more heterogeneous and/or homogeneous imaging devices, such as systems containing 2 imaging devices, 3 to 5 imaging devices, and the like. In such embodiments, the imaging devices may be identical or may differ from at least one other imaging device in at least one way, such as the objective power, speed of image acquisition, type of filter(s) (e.g., different filter wheels), type of camera(s), source of illumination(s), and the like.

Imaging devices may be adapted to include a sample holding device of the present disclosure. Embodiments of sample holding devices of the present disclosure include two first walls of approximately equal length positioned in opposition, the first walls each defining a cutout portion, an internal beveled edge and an internal bottom lip portion; and two second walls of approximately equal length positioned in opposition, the second walls each defining an internal beveled edge and an internal bottom lip portion; wherein each of the two second walls are shorter in length than each of the two first walls, and wherein the two first walls and the two second walls together define a sample receiving area. In certain aspects, the device is so dimensioned as to receive a sample having a standard size, such as a multi-well plate having a 127.5 mm×85 mm footprint. Sample holding devices may include an actuator (e.g., a passive or active actuator) configured to secure a sample that is placed in the sample holding device.

Systems may include hardware and/or software for performing a number of additional tasks. For instance, in certain aspects systems include a processor programmed to acquire an image of the sample using the imaging device; identify a fiduciary mark in the image; compare the image of the fiduciary mark with a reference image; and move the sample so that the fiduciary mark is in substantially the same position as in the reference image. Moreover, in certain aspects systems include a processor programmed to process one or more images of a sample, such as by organizing a plurality of images of the sample; stitching two or more images of the sample together (e.g., using rigid or flexible stitching); aligning two or more images of the sample; identifying objects within an image of the sample; tracking an object through a temporal series of images of the sample; and/or extracting data from objects identified within an image.

Also provided by the present disclosure are methods of acquiring images of a sample, and methods for organizing and/or processing such images. For example, in certain embodiments methods of acquiring an image of a sample include moving the sample using a transport device controlled by a processor to a sample holder of an imaging device identifying, with the processor, a fiduciary mark on the sample; aligning, with the processor, the sample holder so that the fiduciary mark is in substantially the same position as in a reference image; and acquiring, using the imaging device controlled by the processor, an image of the sample. Also provided are methods for processing one or more images, such as by organizing a plurality of images of the sample; stitching two or more images of the sample together (e.g., using rigid and/or flexible stitching); aligning two or more images of the sample; identifying objects within an image of the sample; tracking an object through a temporal series of images of the sample; and/or extracting data from objects identified within an image.

These and other features will be apparent to the ordinarily skilled artisan upon reviewing the present disclosure.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

In certain aspects, the systems and methods of the invention involve imaging of one or more cells which are provided on a substrate. In this context, "substrate" is meant to describe the material on which the sample(s) for imaging are provided (e.g., where cells are grown). The substrate may comprise a plurality of wells (i.e., at least two), which can be provided in an array format. The term "sample" may be used herein to refer to a substrate of any type (e.g., a multi-well plate) that includes a biological material, such as cells and/or tissues, and/or a non-biological material (e.g., a synthetic, chemical, or other material), thereon. Non-biological samples of interest include, but are not limited to, carbon nanotubes.

A "multi-well plate" is a non-limiting example of a well-containing substrate in which multiple discrete regions are provided, whereby the wells are provided in an array. Another manner of providing discrete regions is presented, for example, in *Nature* vol. 411: 107-110 noted above where a monolayer of cells is grown over DNA spots, whereby discrete image/analysis areas are provided. A further example is in a DNA or protein array. Substrates can comprise any suitable material, such as plastic (e.g., polystyrene, black polystyrene, etc.), glass, and the like. Plastic is conventionally used for maintenance and/or growth of cells in vitro, and is referred to in the specification as exemplary of substrate materials without limitation.

By "well" it is meant generally a bounded area of a substrate (e.g., defined by a substrate), which may be either discrete (e.g., to provide for an isolated sample) or in communication with one or more other bounded areas (e.g., to provide for fluid communication between one or more samples in a well). For example, cells grown on the substrate are normally contained within a well, which can further provide for containing culture medium for living cells.

A "multi-well plate", as noted above, is an example of a substrate comprising wells in an array. Multi-well plates that are useful in connection with the methods, systems and/or devices of the present disclosure can be of any of a variety of standard formats (e.g., plates having 2, 4, 6, 24, or 96, wells), but can also be in a non-standard format (e.g., 3, 5, 7, etc. wells).

By "discrete region" it is meant a spot or grouping of interest that may be bounded (as in a well) or simply have a definable boundary, separate from other adjacent units. Whether presented in an array or otherwise, such discrete regions are advantageously provided in a preset pattern. Oftentimes, the pattern will be regular and repeating, though it need not be.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
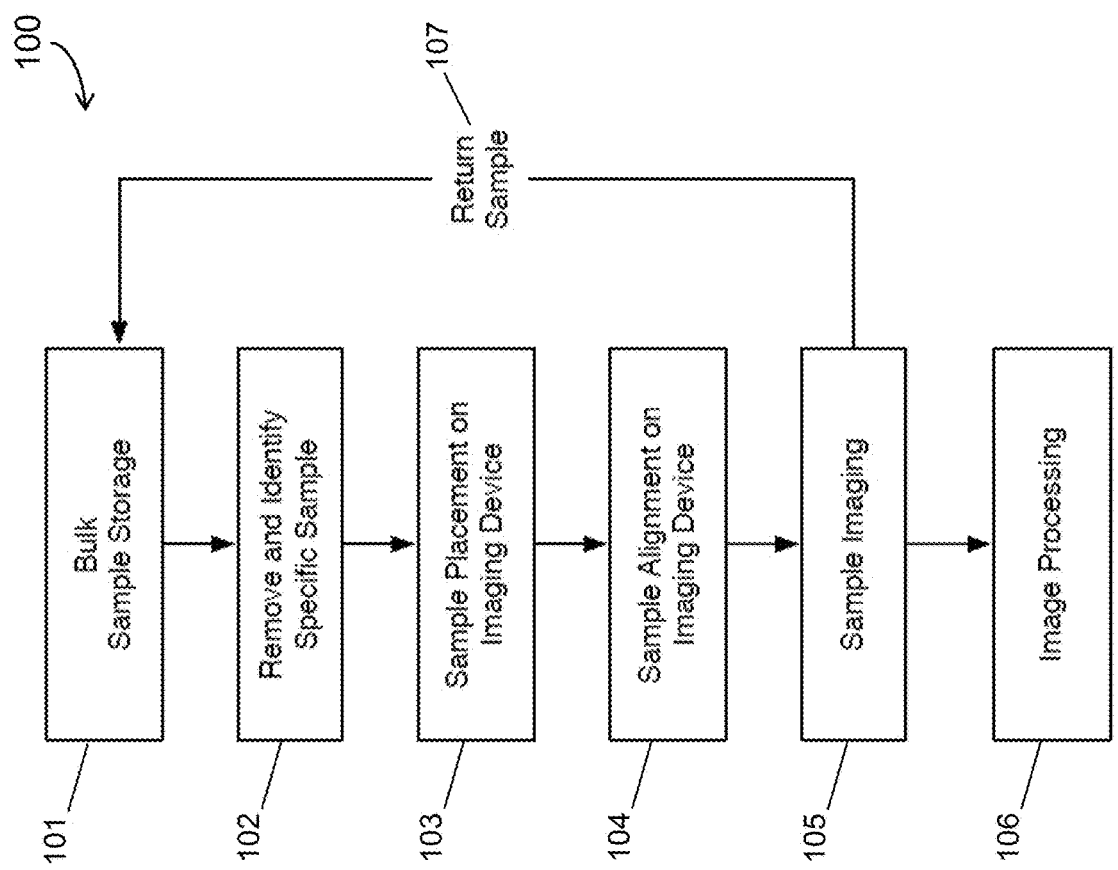
FIG. 1 is a flowchart representing capabilities of certain embodiments of the present disclosure.

As described above, the present disclosure provides automated robotic microscopy systems that facilitate high throughput and high content analysis of samples, including biological samples such as living cells and/or tissues. In certain aspects, the systems are configured to reduce user intervention relative to existing technologies, and allow for precise return to and re-imaging of the same field (e.g., the same cell) that has been previously imaged. This capability enables experiments and testing of hypotheses that deal with causality over time with greater precision and throughput than conventional microscopy methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

For example, reference to a "well" or a "multi-well plate" is made throughout the specification for the purposes of clarity and convenience only, and is not meant to be limiting as to the substrate, since aspects of the present invention encompass imaging of any discrete region as described herein or otherwise. It should also be apparent from the context herein, that many aspects of the invention are applicable to imaging or scanning any region—whether discrete or not. Furthermore, while the invention is described primarily in terms of use with biological samples and living cells, it may, however, be used for imaging of any types of samples, with biological materials being of particular interest. For example, the invention can be used in imaging and analysis of a variety of biological materials, such as cells, particularly living cells; the specification refers to "cells" throughout for the purposes of clarity and convenience only, and is not meant to be limiting. In addition, the invention can be applied to acquisition and analysis of any suitable optical image, of a variety of different spectral ranges, e.g., any range of color, produced for example by, reflected light fluorescent emissions, luminescent emissions, chemiluminescent emissions, etc. Reference is made throughout the specification to, for example, phase contrast and fluorescent images; however, the invention is not so limited. The scope of the present invention will be established by the appended claims.

As used herein and in the appended claims, the singular forms "a", "and", and "the" include plural referents unless the context clearly dictates otherwise. Thus, for example, reference to "an image" includes a plurality of such images, and reference to "the objective" includes reference to one or more objectives and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any element. As such, this statement is intended to serve as antecedent basis for use of such exclusive terminology as "solely", "only" and the like in connection with the recitation of claim elements, or the use of a "negative" limitation.

The publications (including patents) discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Aspects of the present disclosure relate to an automated or robotic microscope system and methods that facilitate high through-put analyses on samples, such as living or fixed biological materials such as cells or tissues. One aspect of the invention allows for precise return to and re-imaging of the same field of living cells that have been imaged earlier.

System hardware is preferably configured to allow imaging of live cells grown on tissue culture plastic that can be maintained for long lengths of time (days to months) in tissue culture dishes. By growing cells on a substrate (e.g., tissue culture plastic), cell positions become relatively fixed with respect to the substrate, which permits subsequent return to precisely the same field of cells.

The invention is implemented by way of hardware, optionally as described below, and computer programming. Programming embodying the features or methodology described herein may be originally loaded into the automated microscope, or the microscope may be preprogrammed to run the same. Such programming, routines and associated hardware constitute various "means" as may be referenced in the claims made hereto. For example, the programmed computer referenced herein comprises a means for directing the action of the various controllers provided. Associated programming can be recorded on computer readable media (i.e., any medium that can be read and accessed by a computer). Such media include, but are not limited to, magnetic storage media, such as floppy discs, hard disc storage medium, and magnetic tape; optical storage media such as CD-ROMs and DVDs; electrical storage media such as RAM, ROM and EPROM; and hybrids of these categories such as magnetic/optical storage media.

Various aspects of the system and methods of the invention will now be described in more detail. Such descriptions are followed by Examples providing additional, optional aspects of the invention.

Systems

As described above, aspects of the present disclosure relate to an automated or robotic microscope system and methods that facilitate high throughput analyses on samples, such as living or fixed biological materials such as cells or tissues. In certain aspects, such systems of the present disclosure may include hardware and/or software that facilitates bulk sample storage, removal and identification of a specific sample from the bulk sample storage, placement of the sample on an imaging device, aligning the sample on the imaging device, imaging the sample, and/or returning the sample back to the bulk sample storage (see, e.g., FIG. 1). In certain embodiments, systems further include the capability of processing the image(s) taken of a sample.

Aspects of embodiments of the systems of the present disclosure include systems with one or more subsystems with components for carrying out the aforementioned steps. For instance, in certain aspects systems of the present disclosure may include one or more of the following: a bulk sample storage subsystem; a sample identification subsystem; a sample placement subsystem; a sample alignment subsystem; a sample imaging subsystem; an image processing subsystem; and a sample transport subsystem, each of which are described herein.

A system, or a subsystem thereof, may be controlled by one or more processors configured to control the system and/or subsystem. In certain aspects, the processor(s) may execute instructions from one or more software modules to cause the system or subsystems thereof to facilitate bulk sample storage, to remove and/or identify a specific sample from bulk sample storage, to place a sample on an imaging device, to align a sample on an imaging device, to image a sample, to place a sample into bulk sample storage, and/or to process image(s) taken of a sample. A software module may reside in RAM memory, flash memory, ROM memory, EPROM memory, EEPROM memory, registers, hard disk, a removable disk, a CD-ROM, or any other form of storage medium known in the art. A storage medium may be coupled to the processor such that the processor can read information from, and write information to, the storage medium. In the alternative, the storage medium may be integral to the processor.

In certain aspects, one or more samples (e.g., one or more multi-well plates containing biological material, such as cells) may be stored in a bulk sample storage subsystem. A processor may be configured to cause the bulk sample storage subsystem to heat, cool and/or maintain the sample(s) contained therein at a given temperature(s). A processor may be configured to cause the bulk sample storage subsystem to remove a sample stored therein, such as by using an automated arm contained within the bulk sample storage subsystem.

The sample removed from bulk sample storage may be transferred, e.g. to a sample identification subsystem or to an imaging device. In certain aspects, such transfer is achieved using a sample transport subsystem, which may include one or more components (e.g., a belt, robotic arm, and the like) controlled by a processor for moving the sample.

A sample identification subsystem may contain one or more sensors (e.g., a barcode reader, optical sensor, and the like) that may detect one or more distinguishing marks on the sample (e.g., a barcode, QR code, and the like). The sample identification subsystem may be in electronic communication with a processor, configured to receive the information from the sensor(s) so as to identify the particular sample. Once a sample has been identified, the processor may apply one or more different parameters (e.g., from a parameter file) to tailor the handling, imaging and/or image processing for that particular sample.

In certain aspects, a sample may be placed on an imaging device (e.g., an optical scanner, microscope and the like) by a sample placement subsystem. The sample placement subsystem may include one or more components (e.g., a belt, robotic arm, and the like) controlled by a processor for moving the sample into position on the imaging device. The particular components included in a sample placement subsystem may vary based upon, for example, the specific sample type, the particular imaging device, the distance to be moved, and the like. For instance, in certain aspects, a sample placement subsystem may include the use of a plate holder (e.g., a plate holder as depicted in any of FIGS. 7-17), into which a sample (e.g., a multi-well plate containing biological material thereon) is placed using a robotic arm. Once placed on an imaging device, systems of the present disclosure may include a sample alignment subsystem to refine the alignment of the sample placed on an imaging device. Such sample alignment subsystems may include, for example, components to move the imaging stage, to move the imaging lens or camera, software modules, and other components, as described herein.

Figure 3:
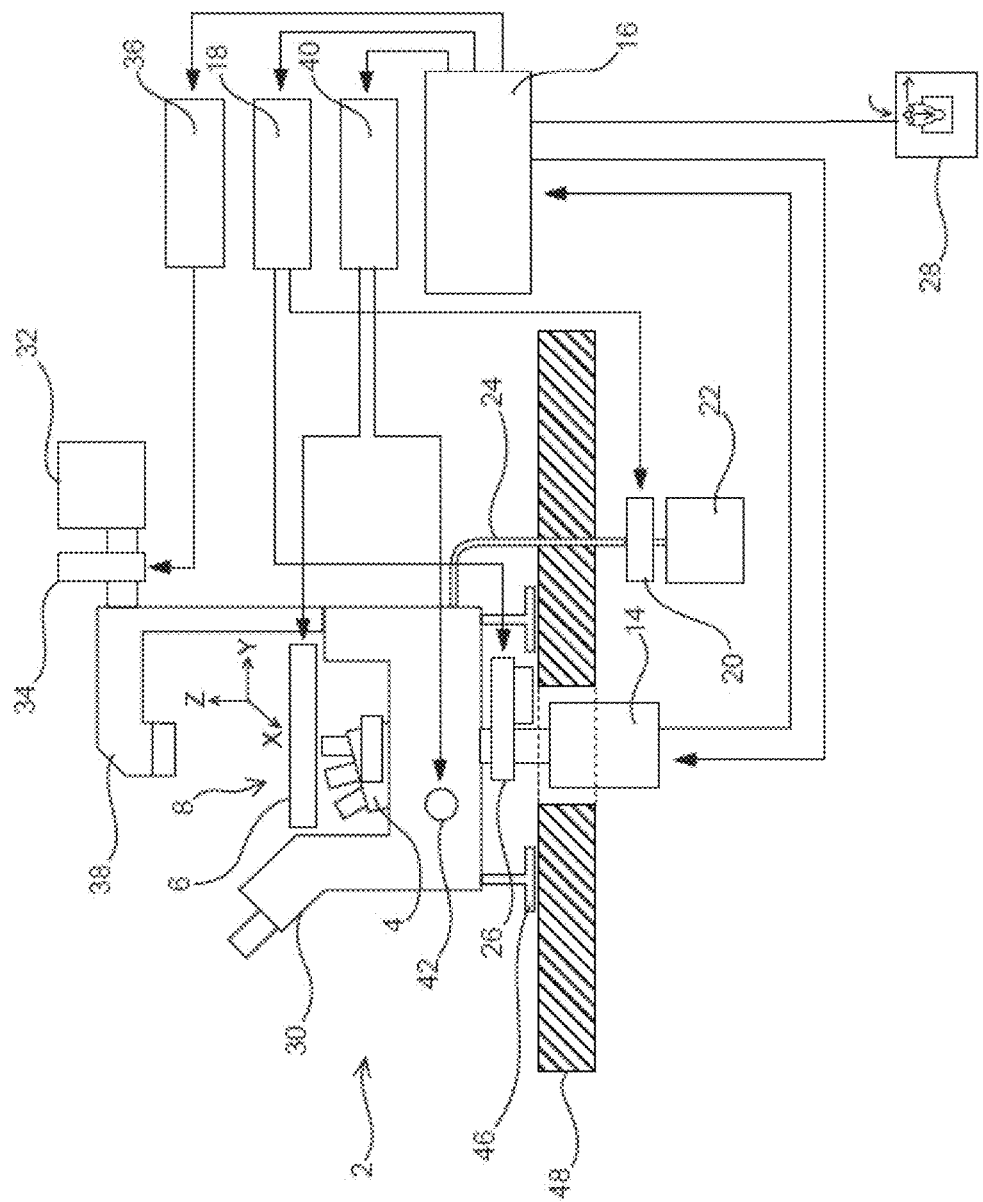
FIG. 3 schematically illustrates an imaging device (e.g., an optical scanner or microscope) as may be used in systems of the present disclosure.
Figure 4:
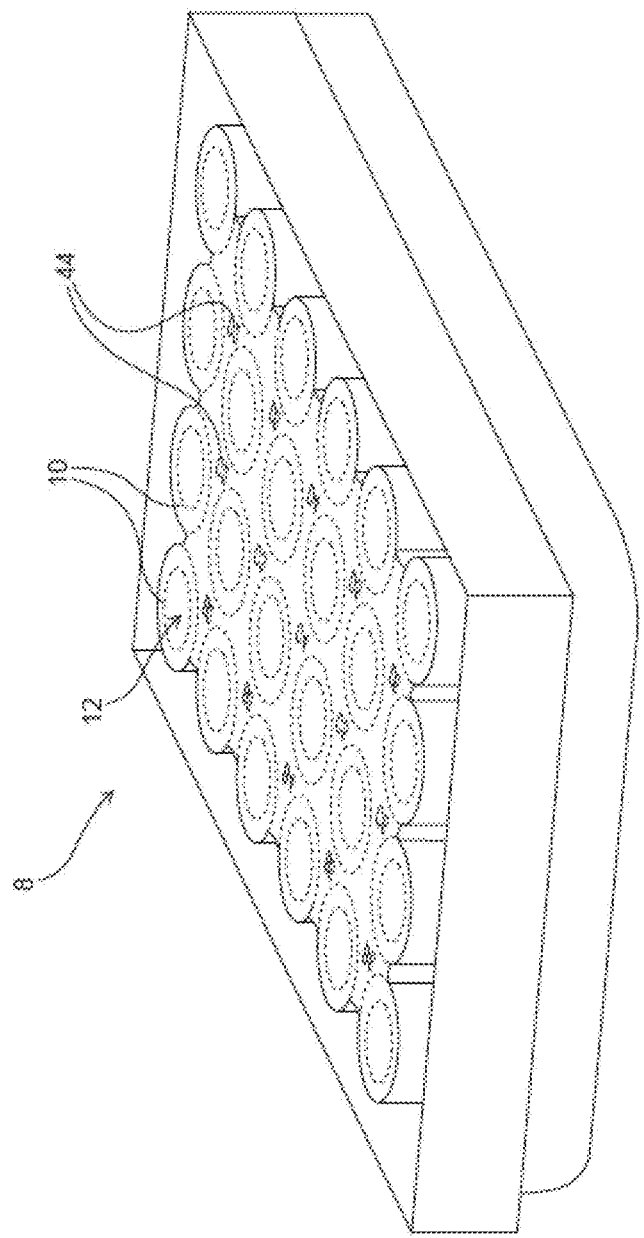
FIG. 4 is a perspective view of the underside of a multi-well plate as may be used in growing, storing and observing cells with automated microscopes of the present disclosure. The side shown is that which faces to the optics of an inverted microscope for inspection, though the plate itself will generally be right side up in use.

Systems of the present disclosure include at least one imaging system. In certain aspects, an imaging system includes an optical scanner or microscope as depicted in FIG. 3, which depicts an inverted microscope body 2, with objectives 4 positioned beneath the stage 6, that is used to image a sample and to keep the specimen plane a relatively fixed distance from the objectives. FIG. 4 shows a dish or well plate 8 with individual wells 10 for samples. Imaging is generally performed through the base material 12 of the culture dish or well plate as will be discussed further below in terms of reducing phototoxicity. The camera 14 (e.g., comprising a CCD (charged coupled device)) is shown placed directly beneath the microscope body to eliminate the need for an extra mirror within the microscope body that could reduce the amount of emitted light. A fast, high sensitivity CCD camera with a wide dynamic range may be used for high throughput capability with computer control, to allow resolving and measuring of objects based on intensity, and so that less illumination of the specimen is required. Programmed computer 16 controls automatic switching (via controller 18) between different fluorescence excitation and emission filter combinations is achieved by interposing one position filter wheel 10 or filter wheel and shutter combination 20 between a light source 22, e.g., a Xenon light source, and a fiber optic (liquid light guide) 24 that carries the light to the microscope (excitation) and another filter wheel 26 between the microscope body and the camera (emission). Automated filter changes (again, via controller 18) make it possible to resolve and relate different structures or functional processes using multiple fluorescence indicators. Additional hardware may include a manual input/control device 28 such as a "joy-stick", touch pad, keypad, or the like in order to manually scan the plate to verify features though eyepiece(s) 30. Though such features are not required of the present invention, they provide a convenience to which many users are accustomed. Also, vibration isolating footings 46 to interface with a table 48 or other support surface may be advantageously employed.

Additional hardware which may be utilized in connection with system focusing is described below. Such hardware may include an incandescent or LED light source 32 moderated by an electronic shutter 34, which is in turn operated by a controller 36. When the shutter is open, light is transmitted from the source via optics 38 to illuminate the field of view of the objectives. Such lighting is utilized, preferably in connection with phase contrast optics where a plastic well plate is used, to enable focusing without the use of the xenon light source. Such an approach using a secondary light source may be desirable in that very low intensity (substantially) white light is all that is required to achieve focus. It also avoids dependence on light from fluorescent objects that may become less numerous or even disappear over time. In contrast, use of a xenon light source and the fluorescence resulting from exposure of a sample to the same requires much greater light intensity that may result in sample phototoxicity if used in connection with system focusing. The focus routines discussed below further limit the potential effects of phototoxicity (even by virtue of exposure to light source 32) by minimizing time spent under illumination for the purpose of focusing. In some embodiments, an automated focusing system, such as the Nikon perfect focus system (PFS) may be utilized as described in greater detail below.

Further, systems of the present disclosure may include an image processing subsystem. An image processing subsystem may include one or more processors that may execute instructions from one or more software modules to, for example, organize the images for a particular sample; stitch two or more images for a particular sample together; align images; identify objects (e.g., cells, such as neurons) within an image; track an object (e.g., a cell, such as a neuron) through a temporal series of images; extract data (e.g., fluorescence data) from objects identified within an image; and/or analyze the resulting images.

Figure 2:
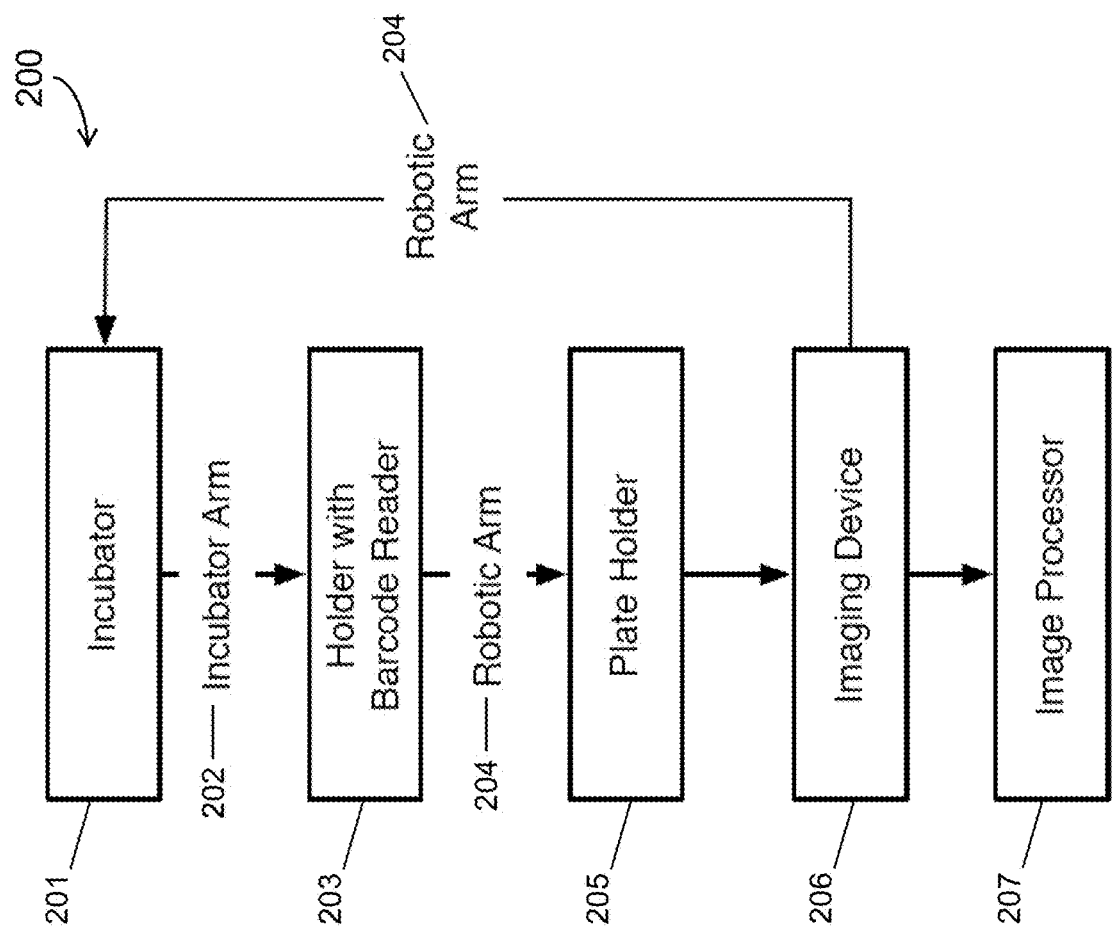
FIG. 2 is a graphical overview of the components of certain systems of the present disclosure.

FIG. 2 presents a further illustration of embodiments of systems 200 of the present disclosure. In the embodiment illustrated here, the bulk storage subsystem includes an incubator 201, which may store two or more samples at a pre-determined temperature. A sample is removed from the incubator by a robotic arm 202 contained within the incubator 201, which places a sample on a sample identification system that includes a holder with a barcode reader 203. The barcode reader 203 reads a specific barcode placed on the plate containing the sample. The barcode reader 203 is in communication with a processor, which is configured to identify the particular sample based at least in part on the particular barcode.

The processor instructs the sample transport system, which includes a robotic arm 204, to pick up the sample from the holder with a barcode reader 203, and transport it to a sample placement subsystem that includes a plate holder 205 (e.g., a plate holder as depicted in FIGS. 7-17). Once placed, a sample alignment subsystem which includes an electronic actuator attached to the plate holder 205, and causes the sample to be aligned within the plate holder 205. Further, the sample alignment subsystem causes the imaging stages of the imaging device 206 to move to a particular location, based upon the identification of a fiduciary mark on the plate, such as a mark that is that is consistently set on or into the plate such as alphanumeric identifiers as element(s) 44 seen in FIG. 4.

The sample is then imaged by the sample imaging subsystem, which includes an imaging device 206 (e.g., an optical scanner or microscope as depicted in FIG. 3). Once the sample has been imaged, the robotic arm 204 of the sample transport subsystem returns the sample to the incubator 201 of the bulk sample storage subsystem. The robotic arm 204 may place the sample back on the holder contained in the sample identification subsystem, at which point the robotic arm 202 of the incubator 201 may pick up the sample and return it to storage. In certain aspects, the barcode reader 203 of the sample identification subsystem records that the sample has been imaged and returned to the incubator, by communicating the barcode to the processor, which is configured to identify the sample and record such information.

Further, the imaging device 206 is in communication (e.g., wired and/or wireless communication) with an image processor 207. In some embodiments, the image processor 207 includes a processor configured to execute instructions from software modules to organize the images taken of the sample; stitch the images together; align the images; identify objects (e.g., cells, such as neurons) within the images; track an object (e.g., a cell, such as a neuron) through a temporal series of images; extract data (e.g., fluorescence data) from objects identified within an image; and/or analyze the resulting images.

The preceding describes general features and components of certain embodiments of systems of the present disclosure. Specific features and components of the systems are described in greater detail below.

Sample Storage

As described above, system hardware is preferably configured to allow imaging of samples can be maintained for long lengths of time. Accordingly, in certain embodiments a system includes a bulk sample storage subsystem that facilitates the storage of samples (e.g., biological materials, such as live cells, on a substrate) for long lengths of time (e.g., days to months).

The bulk sample storage subsystem may include one or more elements to maintain the sample(s) at a desired temperature, humidity, $O_2$ concentration, $N_2$ concentration, $CO_2$ concentration, and the like. The bulk sample storage subsystem may thus contain one or more heating and/or cooling elements, humidifying and/or dehumidifying elements, and the like. Such desired parameters may be maintained using one or more sensors (e.g., a temperature sensor) in electronic communication with a processor in a closed-loop fashion. For example, a processor may be configured to cause the bulk sample storage subsystem to heat, cool and/or maintain the sample(s) contained therein at a given temperature(s) by receiving from a temperature sensor the present temperature, and activating a heating and/or cooling element to raise or lower the temperature to a desired value or range. Aspects of embodiments of systems of the present disclosure include systems in which samples are stored under homogeneous or heterogeneous conditions, e.g., a first portion of the samples are stored under first desired conditions, a second portion of the samples are stored under second desired conditions, etc. In such embodiments in which the samples are stored under heterogeneous conditions, the first, second, etc. conditions may differ from one another by one or more properties, such as temperature, humidity, and the like.

A variety of biological materials may be imaged using systems of the present disclosure. In certain aspects, the biological materials are cells. Suitable cells include eukaryotic cells (e.g., mammalian cells) and/or prokaryotic cells (e.g., bacterial cells or archaeal cells). Biological materials may be obtained from an in vitro source (e.g., laboratory cells grown in culture) or from and in vivo source (e.g., a mammalian subject, a human subject, etc.). In some embodiments, the biological material is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the biological material is obtained from an in vivo source and can include materials obtained from tissues (e.g., cells from a tissue biopsy, cells from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to imaging using the subject systems.

Embodiments of the systems and methods of the present disclosure involve the use of an automated liquid handling workstation (e.g., a MICROLAB® STAR or MICROLAB® NIMBUS liquid handling workstation, such as a MICROLAB® STARlet ML 8 96-prep system, available from Hamilton Robotics, Reno, Nev.) to prepare one or more samples. In such embodiments, the sample(s) may be prepared and moved to the bulk storage subsystem (e.g., using a transport device, as described herein). Such preparation and/or movement may be controlled by one or more processors, wherein the preparation and/or movement are achieved in a semi-automated or automated manner. An example is provided as Example 6 herein.

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys).

Accordingly, a range of sample storage means may be employed by systems of the present disclosure. In some embodiments, systems of the present disclosure include an automated incubator configured to interact with one or more additional components of the transport subsystem described herein, e.g., a robotic arm (e.g., a KiNEDx KX-300-250 robotic arm equipped with a plate gripper including first and second gripper arms, available from Peak Robotics, Colorado Springs, Colo.) as described herein, and referred to in this context as an external robotic arm. In some embodiments, the incubator includes a robotic access gate, an internal robotic arm and an externally located transfer nest or docking location which together allow for the removal and return of a sample plate from and to a specific location in the incubator. The transfer nest includes a sample plate platform which provides an interface location between the incubator and the external robotic arm where the external robotic arm can pick up and return a sample plate during operation of the system. The transfer nest aligns sample plates received from the internal robotic arm or the external robotic arm for accurate transfer positioning, and in some embodiments can correct for a sample plate misalignment of +/−2 mm. For example, in some embodiments, the transfer nest includes beveled posts positioned around the plate nest and meant to guide the plate into the correct location for transfer to and from the microscope and incubator. Suitable incubators include those available from LiCONiC Instruments, Liconic US, Inc., Woburn, Mass., e.g., the STX44-ICBT 70 deg. C. incubator, equipped with a Transfer Nest™.

Despite the beveled posts around the plate nest meant to guide the plate into the correct location for transport to or from the microscope, it is still possible for misalignment to occur if the area of the plate nest is larger than the area of the plate. If physically altering the area of the nest to reduce the variability in plate position is not possible, then a number of mechanical solutions are available. For example, in some aspects the robotic transport device, for instance a robotic arm, is utilized to initially push the plate against one edge or corner and set it down before the actual transport movements to or from the plate nest. In other aspects, an independent motor, for instance a servo motor, is utilized which is placed on the underside of the plate nest. This motor is attached to an arm which can rotate up to push the plate against one edge or corner and then rotate down so that it can not interfere with the transport movements.

Sample Identification

As described above, systems of the present disclosure may include a sample identification subsystem that may contain one or more sensors (e.g., a barcode reader, optical sensor, and the like) that may detect one or more distinguishing marks on the sample (e.g., a barcode, QR code, and the like).

For example, in some embodiments, the robotic microscopy system of the present disclosure includes a bar code reader configured to read a bar code on a sample plate. In some embodiments, the bar code reader is configured to read a barcode positioned along the length of a sample plate. In other embodiments, the bar code reader is positioned to read a barcode positioned along the width of the sample plate. The bar code reader may be positioned to read a barcode on the sample plate while the sample plate is positioned in the transfer nest or docking location described above. In such embodiments, the barcode reader may be positioned on the external surface of the sample storage (e.g., an incubator) or attached to a portion of the transfer nest or docking station such that the barcode reader is positioned to read a barcode on the sample plate, e.g., along the length of the sample plate, while the sample plate is positioned in the transfer nest or docking location. The use of sample plates having unique barcodes thereon in combination with a barcode reader as described herein allows for accurate tracking of specific sample plates as they are transferred to and from the incubator and the plate holder during operation of the system. Sample plates may be provided from the manufacturer with barcodes present, e.g., printed, etched, stamped, provided on a label, etc., or they may be added subsequently using any suitable method known in the art, e.g., printing, etching, stamping, application of an adhesive label, etc.

In some embodiments, a means other than a barcode is used for identifying a sample. Any convenient means of identifying a sample may be used in systems of the present disclosure, such as QR codes, fiducial markers, geometric markers, and the like. Such markers may be detected using optical sensors and other identification means known in the art.

Transport

As discussed above, in some embodiments a system may include a subsystem for transporting a sample, e.g., from an incubator to an imaging device.

In some embodiments, the robotic microscopy system of the present disclosure includes a robotic arm such as a KiNEDx KX-300-250 robotic arm, available from Peak Robotics, Colorado Springs, Colo., equipped with a plate gripper including first and second gripper arms. The robotic arm acts as an intermediary between the incubator and its associated transfer nest or docking location (described above) and the plate holder and associated microscope stage (described below). The robotic arm may include an electric or pneumatic plate gripper, which may be configured to engage a plate in either landscape orientation (two gripper arms positioned to contact the sample plate along the shorter sides of the sample plate) or portrait orientation (two gripper arms positioned to contact the sample plate along the longer sides of the sample plate) for a generally rectangular sample plate. The robotic arm is capable of moving in three dimensions and accordingly many possibilities exist for the relative positions of the plate holder, the incubator and the robotic arm provided that the maximum reach of the robotic arm is not exceeded.

Figure 5:
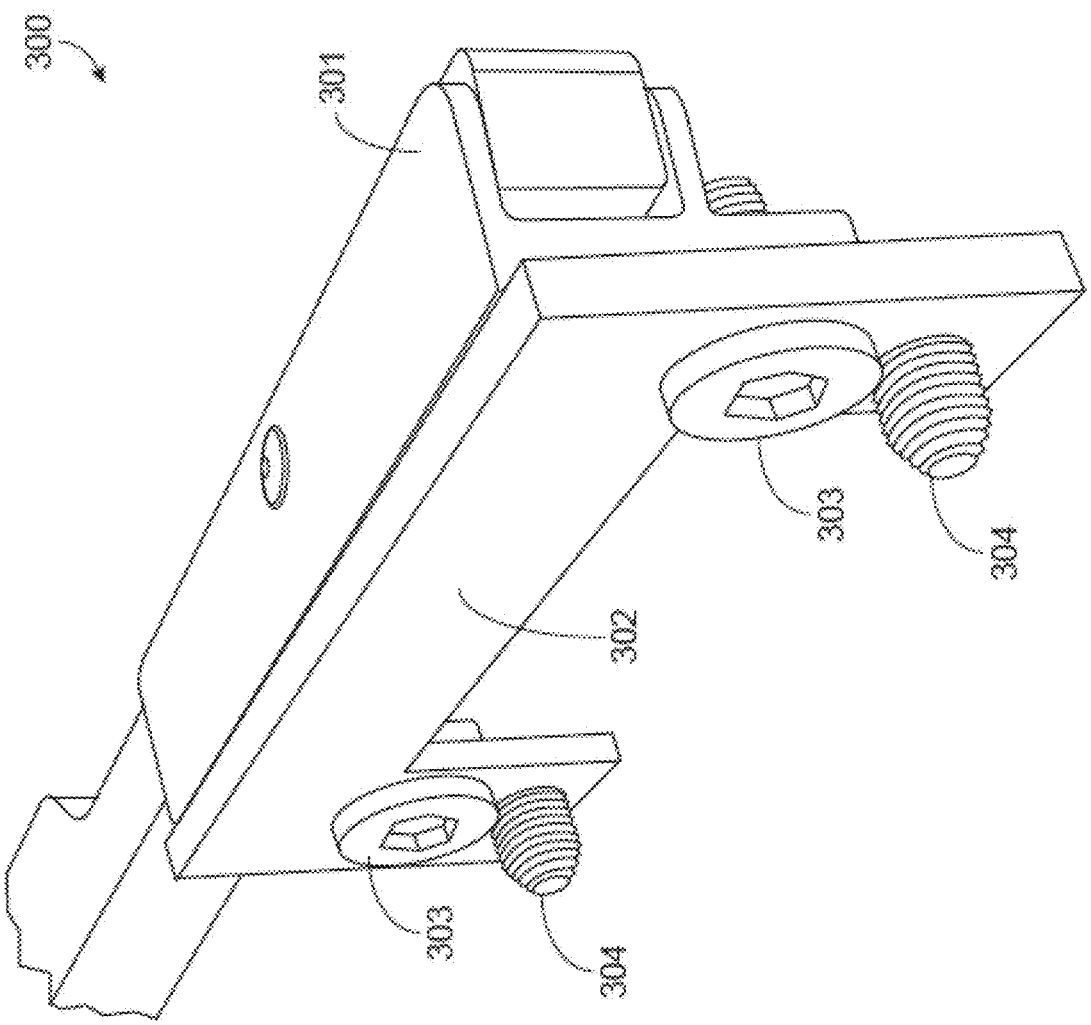
FIG. 5 is a perspective view of the plate-contacting portion of a gripper arm, as may be used with a robotic arm in systems of the present disclosure.
Figure 6:
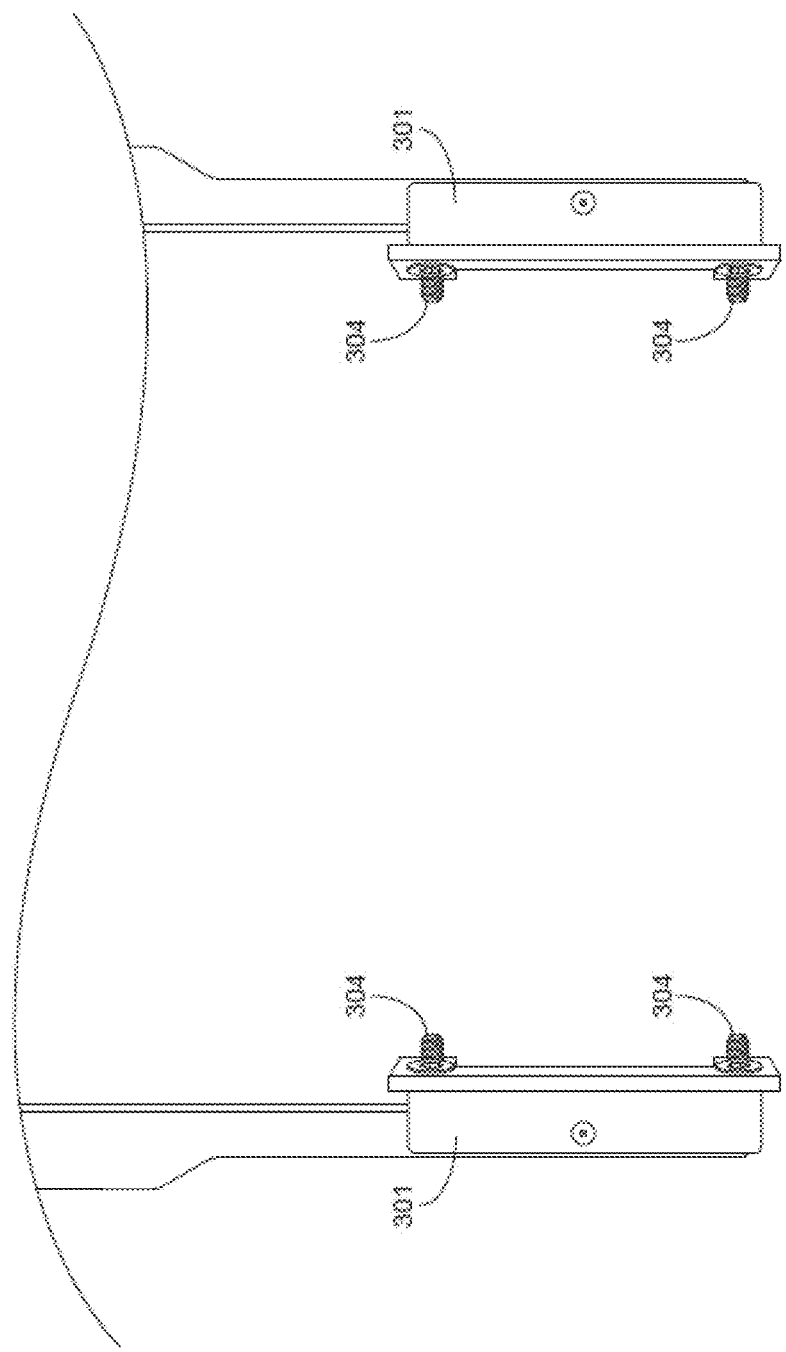
FIG. 6 is a top view of first and second gripper arms of the type shown in FIG. 5, attached to a robotic arm as may be used in systems of the present disclosure.

In certain aspects, a robotic arm may include a plate gripper of the type depicted in FIGS. 5 and 6. The plate gripper may be sized and shaped to facilitate the deposition and/or retrieval of a sample plate to and/or from a transfer nest or docking station of a sample storage device and a plate holder as described herein. Turning to FIG. 5, a gripper arm 300 may include a plurality of extensions 304 (e.g., screws) that contact the periphery of a plate. The extensions 304 may preferably be adjustable for depth, such that when closed the gripper arm contacts the plate via the extensions on a vertical surface of the plate, without causing damage to the plate. In certain aspects, the extensions 304 contain a surface treatment, such as an adhesive, etching, high-friction material, and the like, so as to facilitate securely holding a plate. In certain aspects, the extensions 304 may be manually adjustable. For example, in certain embodiments the extensions 304 include screw sides that may facilitate the lengthening or shortening of the extensions by turning the screws. In other aspects, the extensions 304 may be self-adjustable. By self-adjustable it is meant that the extensions may adjust to accommodate plates of varying sizes without additional intervention by a user. For instance, in certain embodiments the extensions are mounted using springs configured to allow the extensions to move horizontally to accommodate plates of slightly varying dimensions.

FIG. 6 depicts a top view of first and second plate grippers 301. A plate may be retrieved by the gripper arm by being placed between the plate grippers 301, which move towards each other so as to exert a lateral pressure on the plate so as to secure it for transport. A plate may be deposited by the gripper arm by moving the plate to a desired location and causing the plate grippers to move away from each other thereby releasing the lateral pressure on the plate so as to deposit it at a desired location. The grippers may be configured to engage a plate in either landscape orientation or portrait orientation for a generally rectangular sample plate.

Imaging System

Systems of the present disclosure may include an imaging system. In certain embodiments, an imaging system includes an optical scanner or microscope as depicted in FIG. 3.

As depicted in FIG. 3, imaging systems of interest may include an inverted microscope body 2, such as an Eclipse Ti-E/B inverted research microscope, available from Nikon Corporation. Such a body can be used to take advantage of the extra long working distance lenses provided by longer tube length for the objective 6. This makes it possible to capture a focal plane that is farther (many millimeters) away from the tip of the objective but still have a relatively good numerical aperture. The relatively long working distances offered by the setup allows focusing beyond the floor of the tissue culture plate 8, into thick specimens such as transfected neurons within a brain slice without bumping the objective into the dish. Generally, such samples range in thickness from about 50 to about 400 microns.

In certain aspects, the objective 6 is selected so as to balance a need for acquiring a large field of view and high resolution images. In certain aspects, the objective 6 is a Nikon Fluor Series microscope objective, such as a 20× Nikon CFI Plan Fluor ELWD objective, with a 0.45 numerical aperture (NA) and a 6.9-8.2 mm working distance.

In other aspects, a 4× objective may be used. A 4× image is especially well suited for counting cells (e.g., measuring survival) and for some measurements of overall morphology. 4× objectives of interest include commercially available objectives such as those from Nikon and Olympus, such as an Olympus Uplan SL 4×\0.13\PhL, which transmits roughly the same amount of light as the Nikon objective. However, the Olympus objective transmits light more evenly across the field, and the difference in transmission from the edge of the field to the center of the field is twice as good for the Olympus objective as for the Nikon objective.

Embodiments include the use of relatively high NA objectives. Normally, a relatively high numerical aperture objective is preferred to allow collection of more light (i.e., form an image with less signal) with better spatial resolution. In the microscope system of the invention, however, a relatively low numerical aperture lens can still collect enough light to form an image while providing substantially greater depth-of-field such that that the image remains in visible focus over a wider range of actual Z-positions, even where the system does not include a Nikon TiE Perfect Focus System (PFS; described below). In systems lacking such a PFS, this allows focusing once per well (preferably, in the center) followed by capture of a series (e.g., 3×3 or 4×4) of adjacent fields within the same well, that remain in focus; focusing only once per well cuts the time required to image or scan a 24-well plate by one half. This problem is largely obviated in systems that include a PFS because the PFS is engaged in a well which maintains focus the entire time while imaging the well, and it is only turned off prior to moving to the next well.

Plate Holder

As shown in FIG. 3, an imaging system may include a stage 6 that is used to image a sample and to keep the specimen plane a relatively fixed distance from the objectives 4. In some embodiments, the robotic microscopy system of the present disclosure includes a plate holder on the stage 6 configured to interact with one or more additional components of the robotic microscopy system described herein in an automated manner. Specifically, the present disclosure provides a plate holder configured to physically engage, e.g., mechanically attach to, a microscope stage (e.g., an MS2500 XY Flat-Top Extended Travel Stage, available from Applied Scientific Instrumentation (ASI), Eugene Oreg.). The plate holder may be physically attached to the microscope stage using any suitable attachment means known in the art, e.g., screws, bolts, rivets, interlocking mechanisms and the like.

The plate holder is further configured to facilitate the deposition and removal of a sample plate (e.g., a multi-well plate as described herein) using a robotic arm (e.g., a KiNEDx KX-300-250 robotic arm, available from Peak Robotics, Colorado Springs, Colo.) equipped with a plate gripper including first and second gripper arms, e.g., an electric or pneumatic plate gripper, (e.g., an electric Side-Grip-Servo (SGS) plate gripper configured in portrait configuration, available from Peak Robotics, Colorado Springs, Colo.).

In some embodiments, the plate holder includes four walls connected in an approximately rectangular configuration so as to define an internal sample plate receiving area, an internal opening and external, top, side and bottom surfaces. FIGS. 7-10 show various views of one embodiment of a plate holder 400 as may be used in systems of the present disclosure. As shown the top view shown in FIG. 7, the four walls of the plate holder 400 include two first walls 415 of approximately equal length positioned in opposition and two second walls 420 of approximately equal length positioned in opposition wherein each of the two second walls 420 are shorter in length than each of the two first walls 415. The two first walls 415 each include a cutout portion 416, an internal beveled edge 417 and an internal bottom lip portion 418, as best seen in the top perspective view in FIG. 10. The two second walls 420 each include an internal beveled edge 421 and an internal bottom lip portion 422. These elements are provided such that the internal sample plate receiving area is defined in part by a bottom lip portion, which bottom lip portion is made up of the bottom lip portions of the first and second walls. The bottom lip portion of the internal sample plate receiving area in combination with the cutout portions of the walls defines the perimeter of the internal opening.

As discussed above, the cutout portions 416 may be positioned in the two first walls 415, e.g., to provide for engagement with a plate gripper having first and second gripper arms configured to hold a sample plate in portrait configuration. However, it should be noted that the plate holder may additionally, or alternatively, be configured to provide for engagement with a plate gripper having first and second gripper arms configured to hold a sample plate in landscape configuration, in which case the cutout portions would be positioned in the two second walls 420 or in both the two first walls 415 and the two second walls 420.

Figure 7:
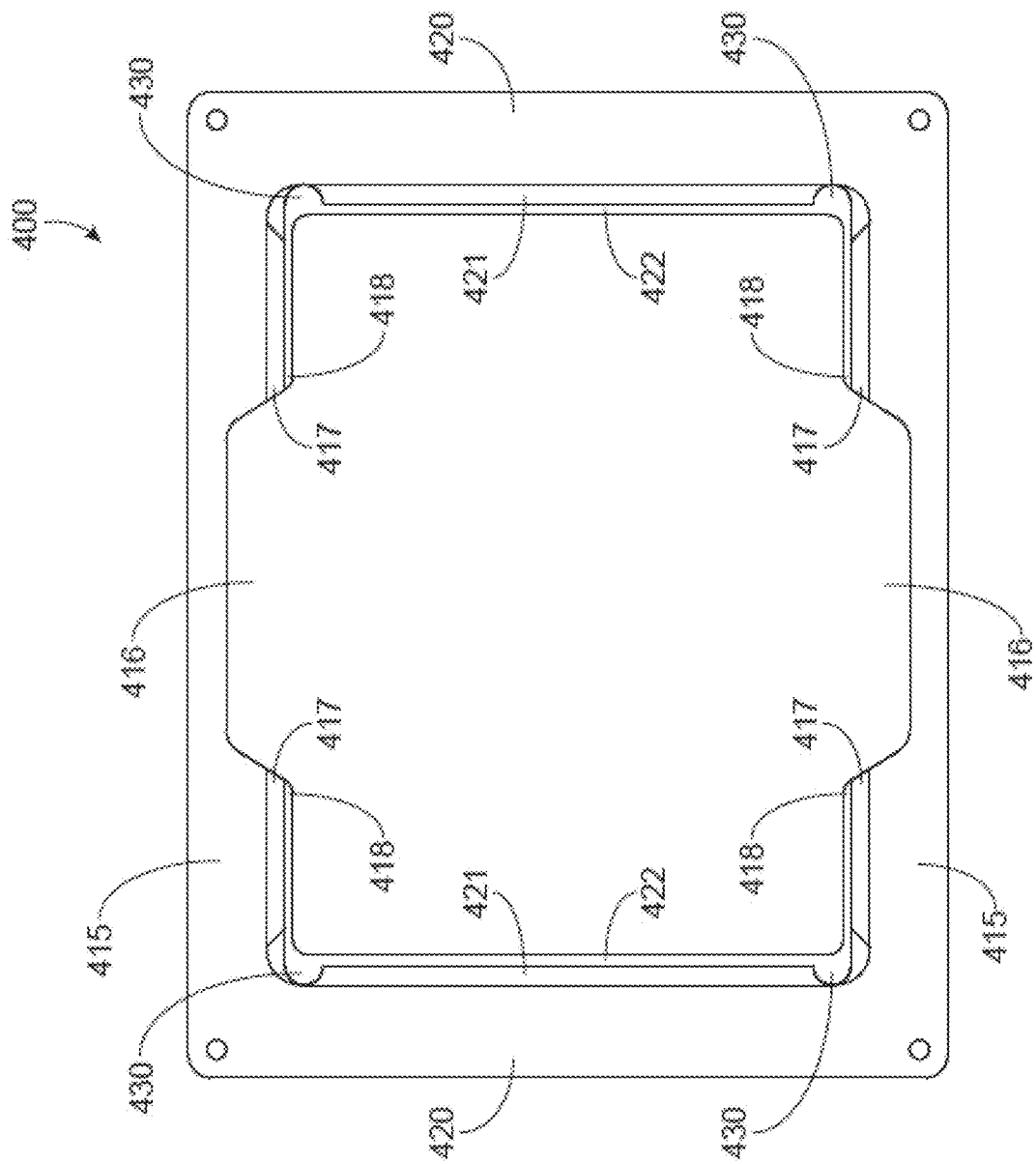
FIG. 7 is a top view of a plate holder as may be used in systems of the present disclosure.
Figure 8:
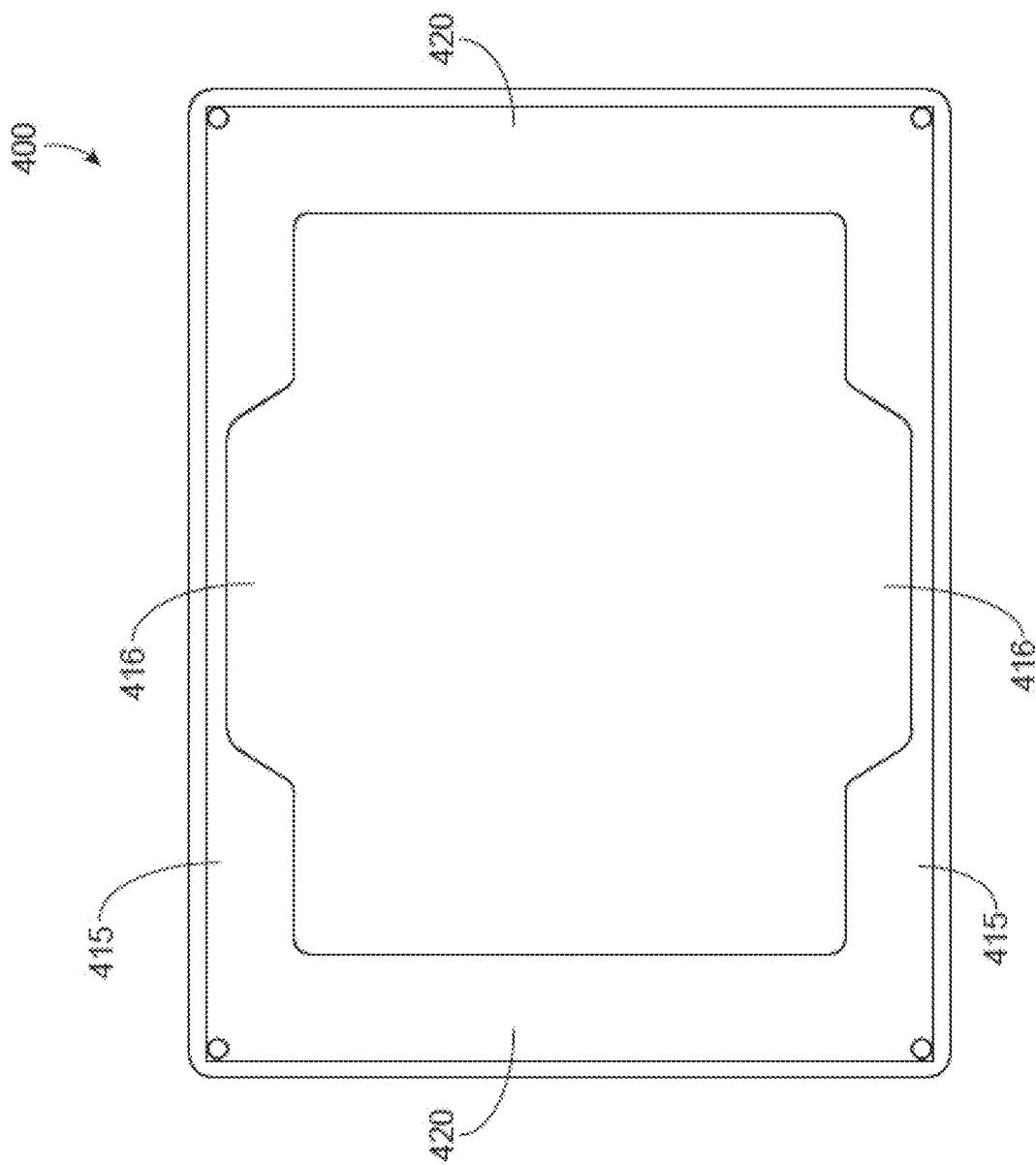
FIG. 8 is a bottom view of the plate holder of FIG. 7.
Figure 9:
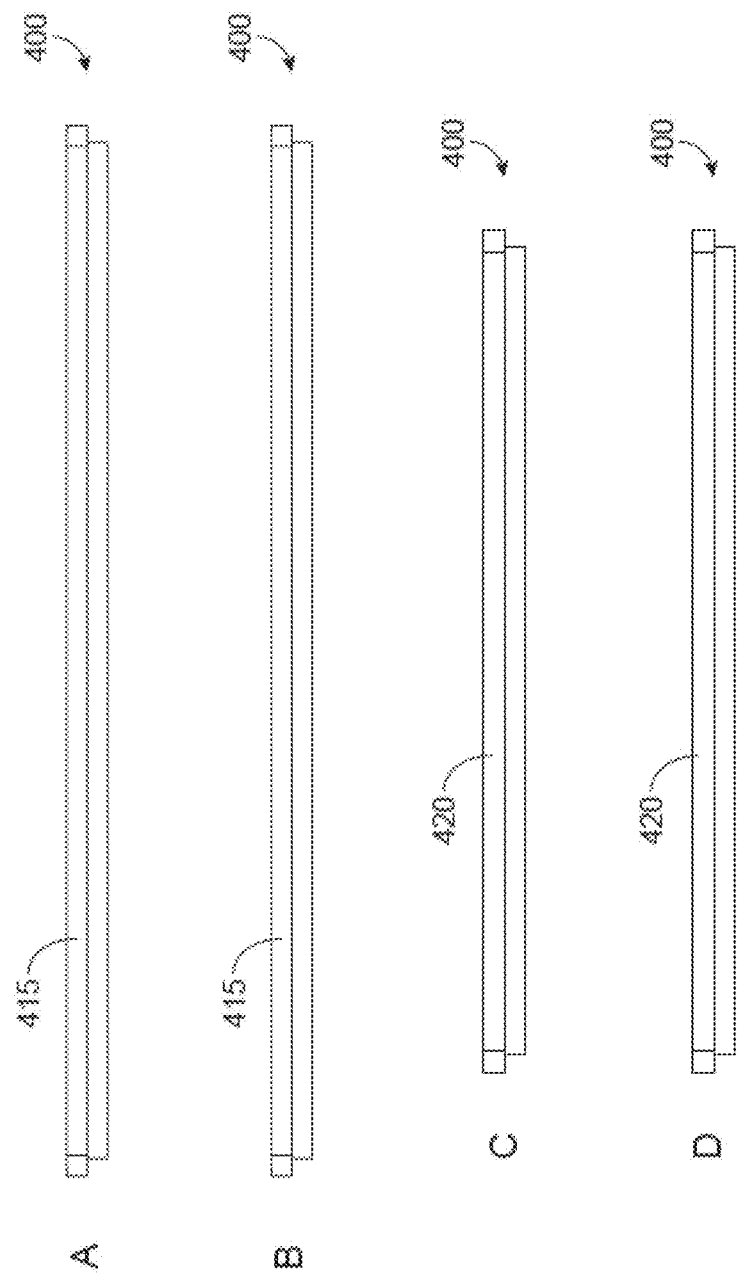
FIG. 9, Panels A-D are side views showing the four sides of the plate holder of FIG. 7.
Figure 10:
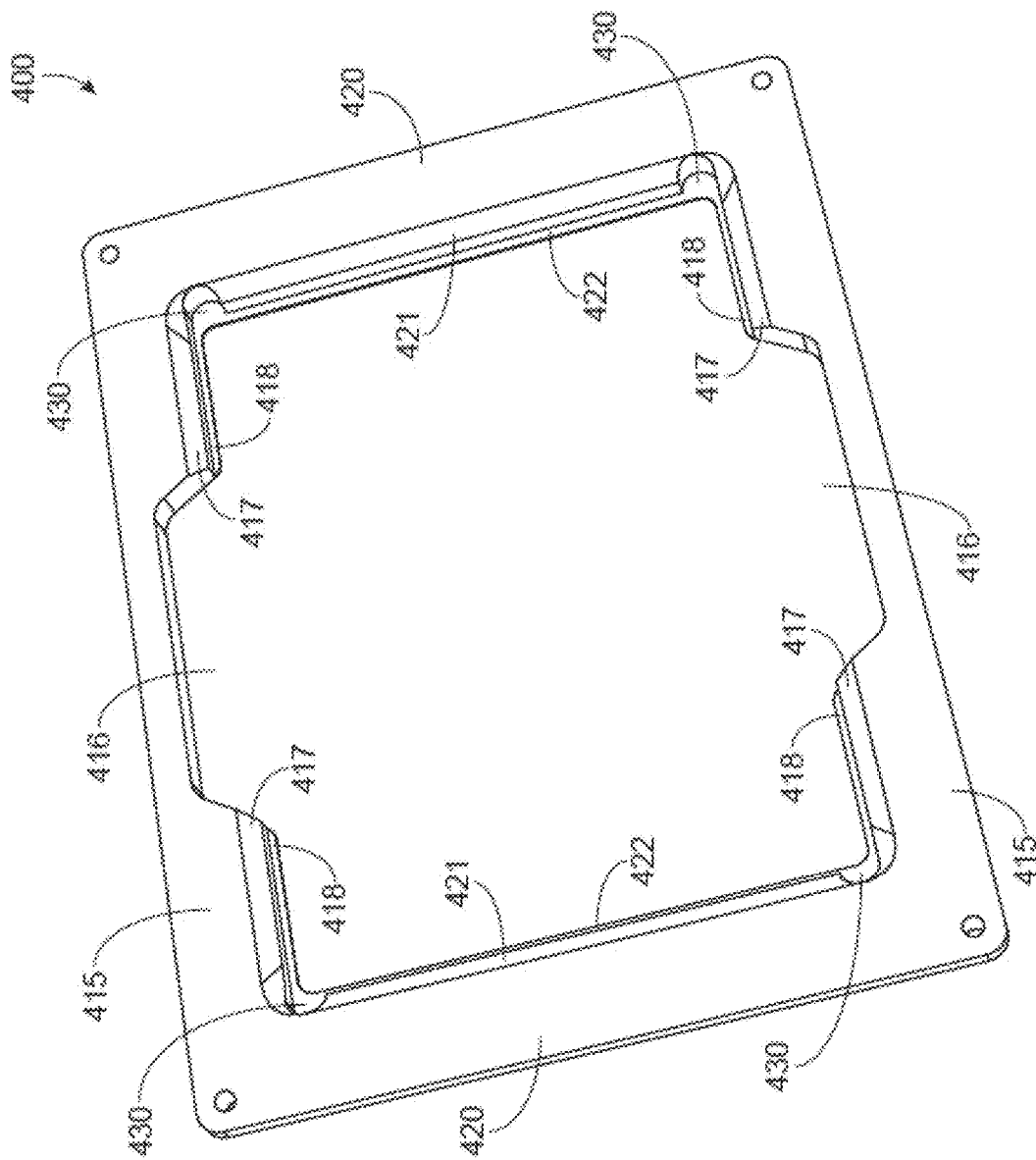
FIG. 10 is a top perspective view of the plate holder of FIG. 7.

In some embodiments, the cutout portions 416 of the two first walls 415 are positioned in an opposed configuration as shown in FIG. 7. However, it should be noted that these cutouts 416 may be modified or repositioned to address changes in the configuration of the plate gripper 400 or plate gripper arms or vice versa. Generally, the cutout portions 416 are sized and shaped to accommodate the dimensions of the gripper arms or vice versa such that the gripper arms can descend vertically into the cutouts such that the sample plate is positioned on the bottom lip portion of the internal sample plate receiving area, release the sample plate and ascend vertically leaving the sample plate positioned in the plate holder for subsequent imaging. The cutout portions 416 are also sized and shaped to accommodate the dimensions of the gripper arms or vice versa to facilitate the removal of a sample plate from the plate holder, in which case the gripper arms descend vertically into the cutouts such that they are positioned on opposing sides of the sample plate. The gripper arms then move towards each other until they contact and grip the sample plate. The gripper arms then ascend vertically thereby removing the sample plate from the plate holder.

As discussed above, the internal sample plate receiving area is defined in part by an internal beveled edge. The internal beveled edge of the internal sample plate receiving area is generally continuous with the exception of the cutout portions (discussed above) and the optional arcuate or rounded corners 430 (discussed below). The angle of the beveled edge relative to the plane of the bottom lip portion of the plate holder is less than 90 deg., e.g., less than 85 deg., less than 80 deg., less than 75 deg., less than 70 deg., less than 65 deg., less than 60 deg., less than 55 deg., less than 50 deg., less than 45 deg., less than 40 deg., less than 35 deg., less than 30 deg., less than 25 deg., or less than 20 deg. In some embodiments, the angle of the beveled edge relative to the plane of the bottom lip portion of the plate holder is from about 90 deg. to about 20 deg., e.g., from about 85 deg. to about 25 deg., from about 80 deg. to about 30 deg., from about 75 deg. to about 35 deg., from about 70 deg. to about 40 deg., from about 65 deg. to about 45 deg., from about 60 deg. to about 50 deg. or about 55 deg.

In some embodiments the beveled edge of the internal sample plate receiving area extends from the plane of the bottom lip portion of the sample plate receiving area to the plane of the top surface of the plate holder, which planes are generally parallel. In other embodiments, the two first walls 415 and the two second walls 420 each include a first portion which contacts the bottom lip portion of the plate holder at an approximately 90 deg. angle and a second beveled edge portion that contacts the top surface of the plate holder and has a beveled edge angle as discussed above relative to the plane of the bottom lip portion of the plate holder. The first and second portions of the respective walls may meet at a point in the respective walls which is approximately equidistant between the planes of the bottom lip portion of the plate holder and the top surface of the plate holder. Alternatively, this meeting point may be positioned closer to the bottom lip portion of the plate holder or the top surface of the plate holder.

As discussed above, the internal sample plate receiving area is defined by a bottom lip portion, which, in some embodiments, meets a portion of each plate holder wall at an approximately 90 deg. angle. The bottom lip portion extends inward, e.g., along its entire length, from the intersection of the bottom lip and the portion of each plate holder wall which meets the bottom lip portion at an approximately 90 deg. angle (or other suitable angle as discussed above). The bottom lip portion extends a sufficient distance to provide a stable base for a deposited sample plate. In some embodiments, the bottom lip portion extends about 2 mm to about 20 mm, e.g., from about 2 mm to about 18 mm, from about 2 mm to about 16 mm, from 2 mm to about 14 mm, from about 2 mm to about 12 mm, from about 2 mm to about 10 mm, from about 2 mm to about 8 mm, from about 2 mm to about 6 mm, or from about 2 mm to about 4 mm from the intersection of the bottom lip and the portion of each plate holder wall which meets the bottom lip portion at an approximately 90 deg. angle (or other suitable angle as discussed above). As discussed above, the bottom lip portion is interrupted along a portion of its length by the cutouts which provide for access by the gripper arms of the plate gripper. In some embodiments the bottom lip portion has a thickness of from about 0.4 to about 0.8 mm, e.g., about 0.5 to about 0.7 mm, or about 0.6 mm.

In some embodiments, in addition to the above components, the plate holder is configured to include arcuate or rounded corners 430 at the internal junction of the two first walls 415 and the two second walls 420. These optional rounded corners 430 may facilitate plate positioning, e.g., during deposition and removal of a sample plate.

The plate holder according to the present disclosure may be made from any suitable material, e.g., aluminum or titanium, and may be produced using any of a variety of suitable methods known in the art, e.g., milling or injection molding.

In some embodiments, the plate holder has an overall thickness of approximately 8 mm and is sized and shaped to receive a sample plate having a Society for Biomolecular Sciences (SBS) Standard 127.5 mm×85 mm footprint. Such embodiments may be configured to provide an internal sample plate receiving area which includes dimensions defined by the internal termination of the beveled edge which dimensions are a length of approximately 128 mm and a width of approximately 86.1 mm.

The beveled edge of the plate holder provides advantages in that it allows for accurate placement of a sample plate despite slight inaccuracies in the x, y, and/or z plate positioning dimensions which may result when using a robotic arm equipped with a plate gripper as described herein to deposit a sample plate in the plate holder. The beveled edge serves to "guide" the sample plate into the correct position in the plate holder for subsequent viewing, imaging and/or analysis.

In some embodiments a plate holder as described herein may be adapted to include an actuator including an arm, which, when actuated, functions to push a sample plate positioned in the internal sample plate receiving area into a consistent corner of the internal sample plate receiving area each time a sample plate is positioned in the internal sample plate receiving area. This allows the plate position to be corrected for rotation once positioned in the internal sample plate receiving area. In certain aspects, the actuator may be passive, such as a passive lever. In other aspects, the actuator may be active, such as an electronically controlled actuator controlled by a processor.

Figure 11:
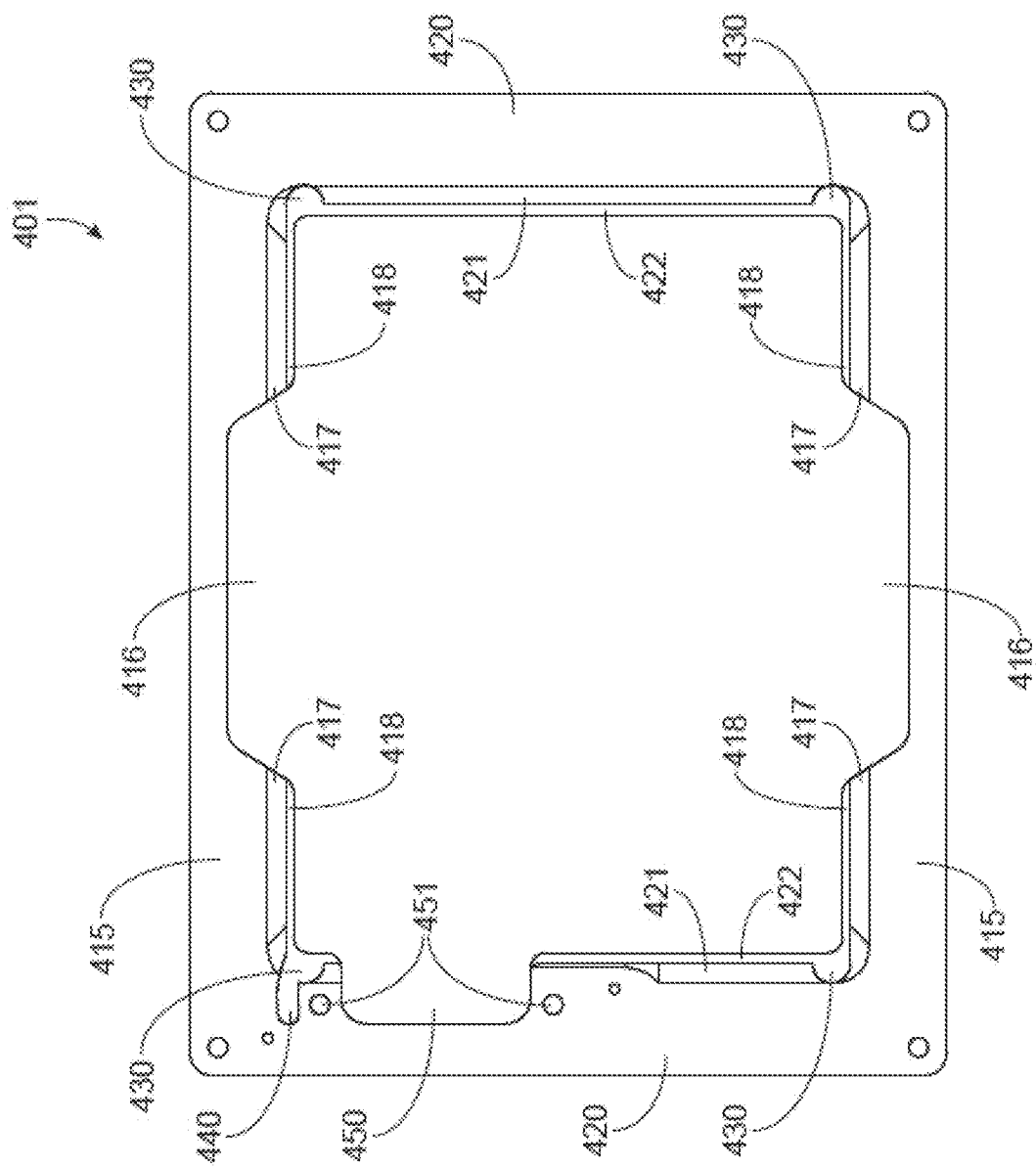
FIG. 11 is a top view of a plate holder having a mounting point for an actuator, as may be used in systems of the present disclosure.
Figure 12:
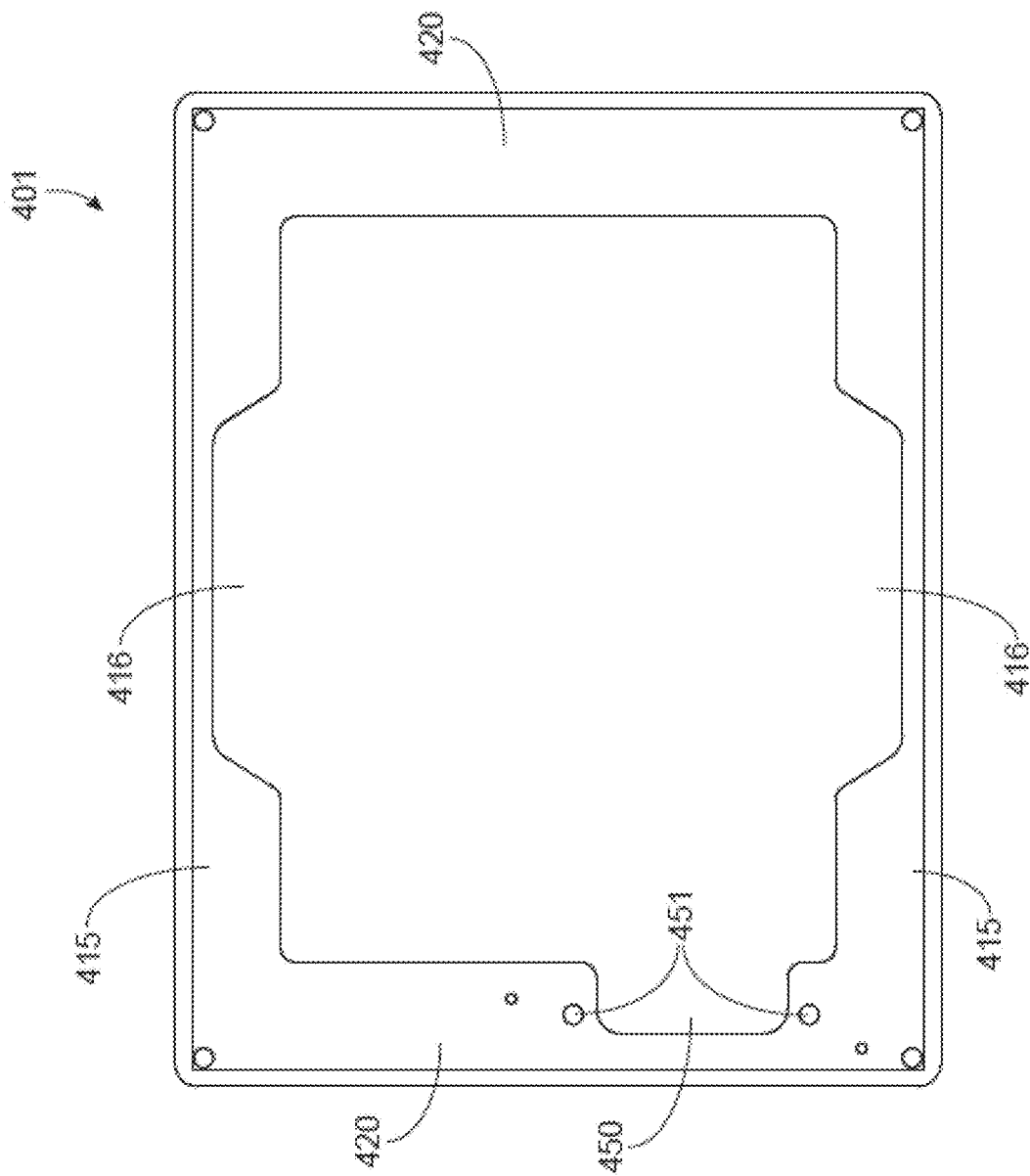
FIG. 12 is a bottom view of the plate holder of FIG. 11.
Figure 13:
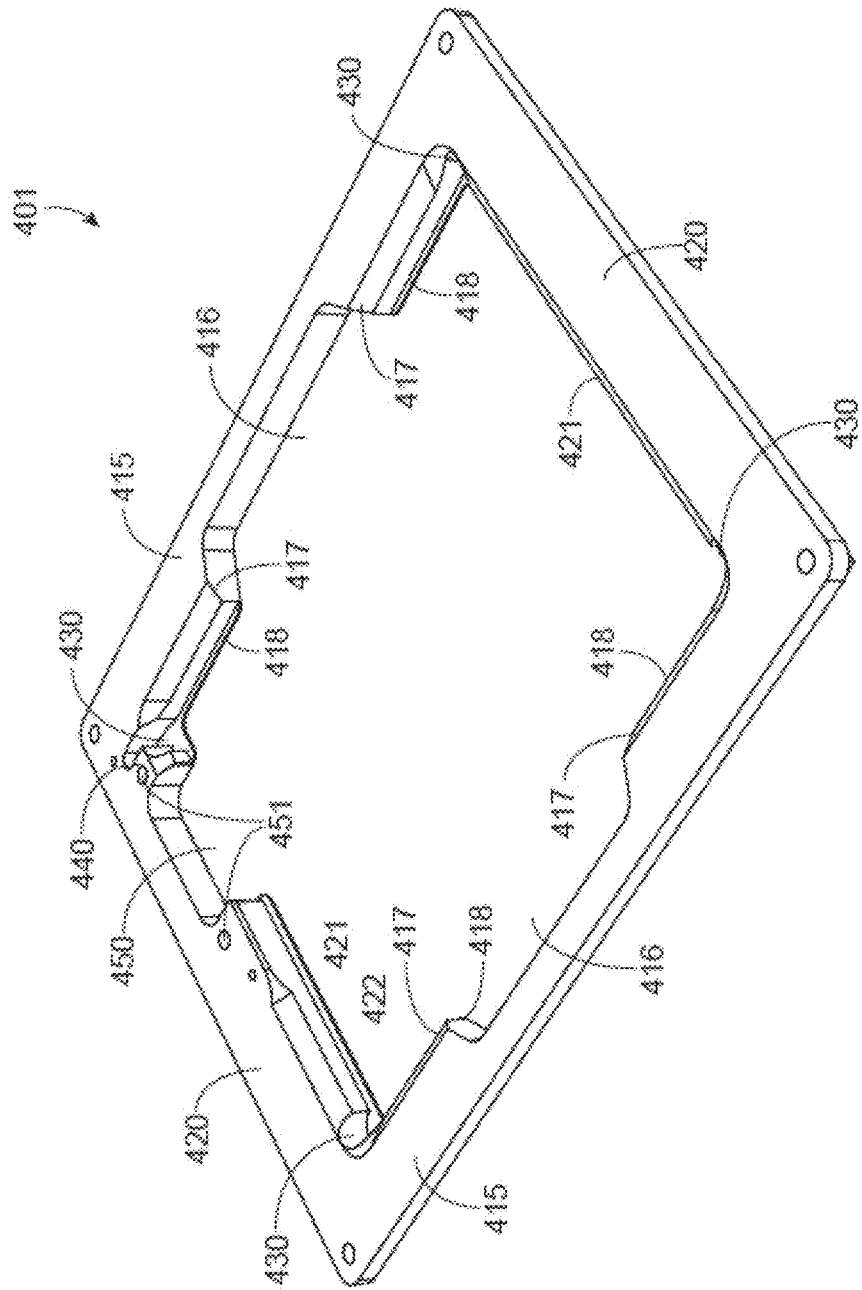
FIG. 13 is a top perspective view of the plate holder of FIG. 11.

FIG. 11 is a top view of a plate holder 401 that has been adapted for inclusion of such an actuator. FIGS. 12-13 provide alternative views of the plate holder 401 depicted in FIG. 11. In the embodiment presented in FIG. 11, the plate holder 401 has been adapted from the embodiment depicted in FIG. 6 by the removal of a portion of material, into which an actuator may be placed, shown as the portion 450. The plate holder 401 also contains mounting holes 451 for securing such an actuator, and an actuator arm cutout 440 to accommodate an actuator arm.

Figure 14:
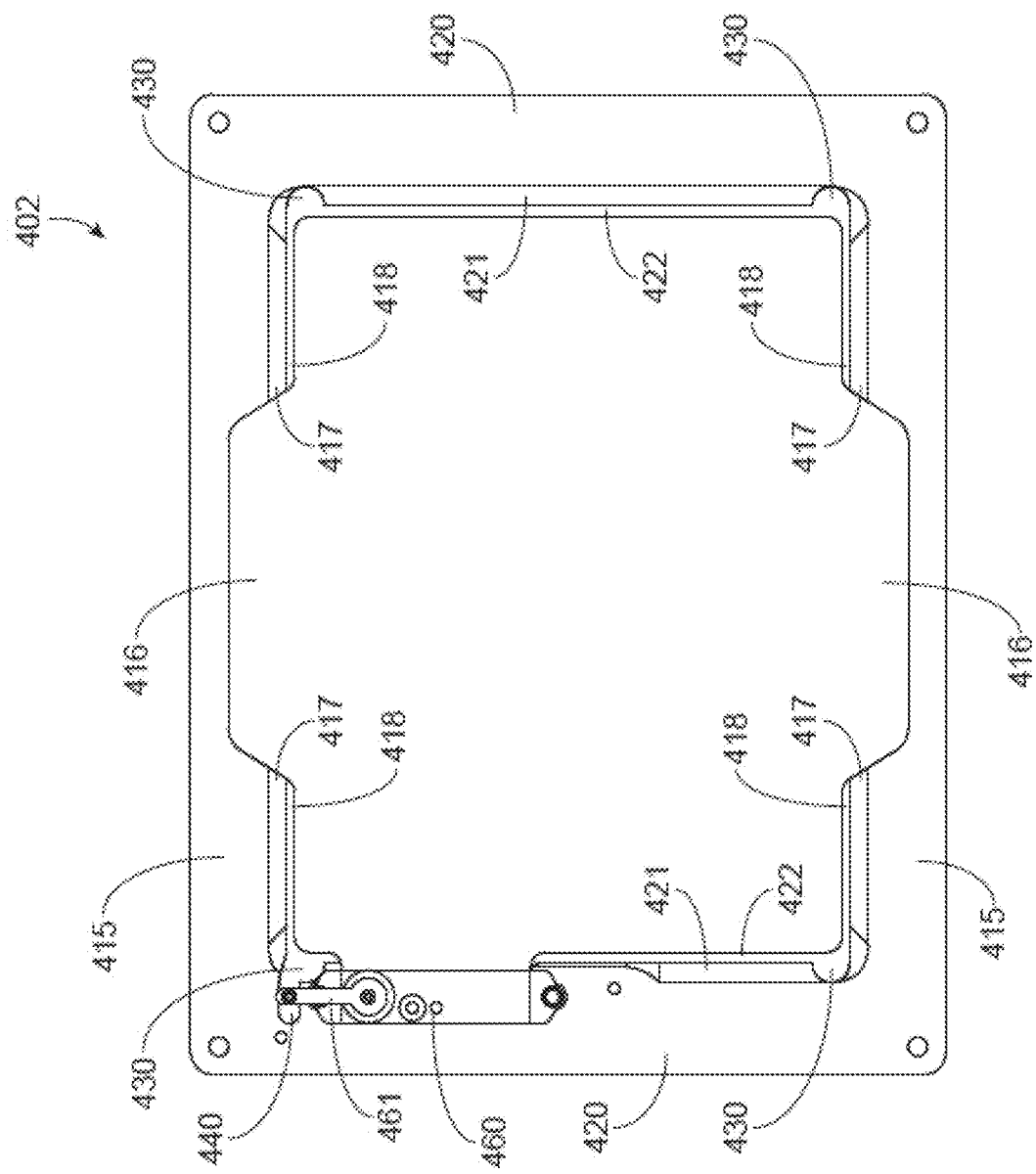
FIG. 14 is a top view of a plate holder with an actuator, as may be used in systems of the present disclosure.
Figure 15:
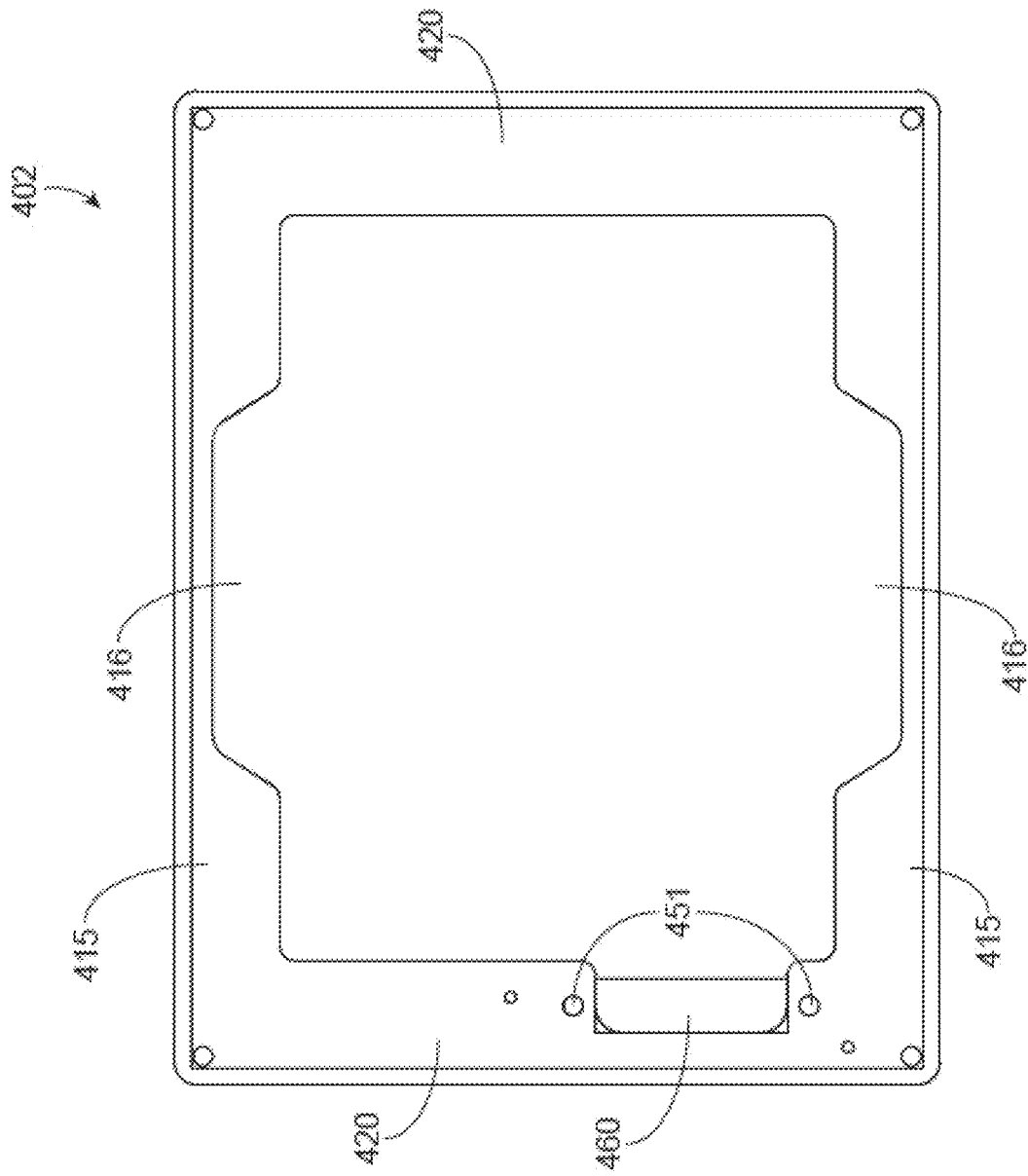
FIG. 15 is a bottom view of the plate holder and actuator of FIG. 14.
Figure 16:
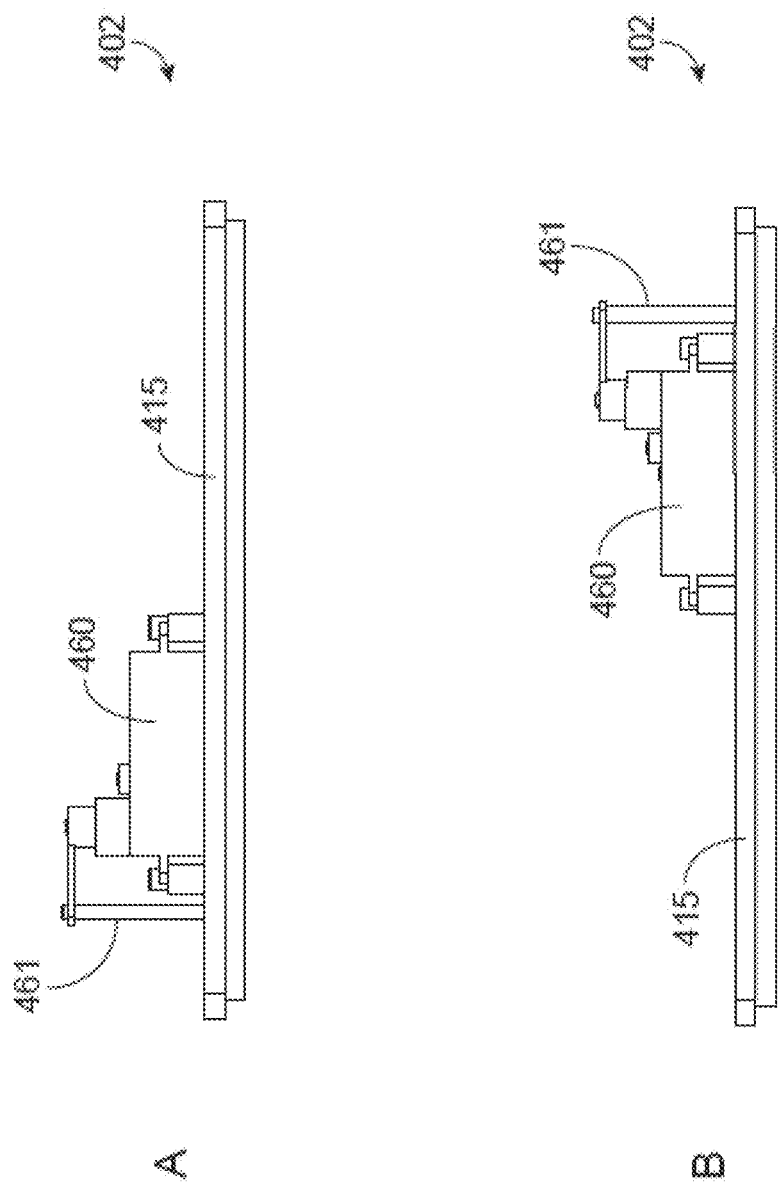
FIG. 16, Panels A-B are side views of the plate holder and actuator of FIG. 14.
Figure 17:
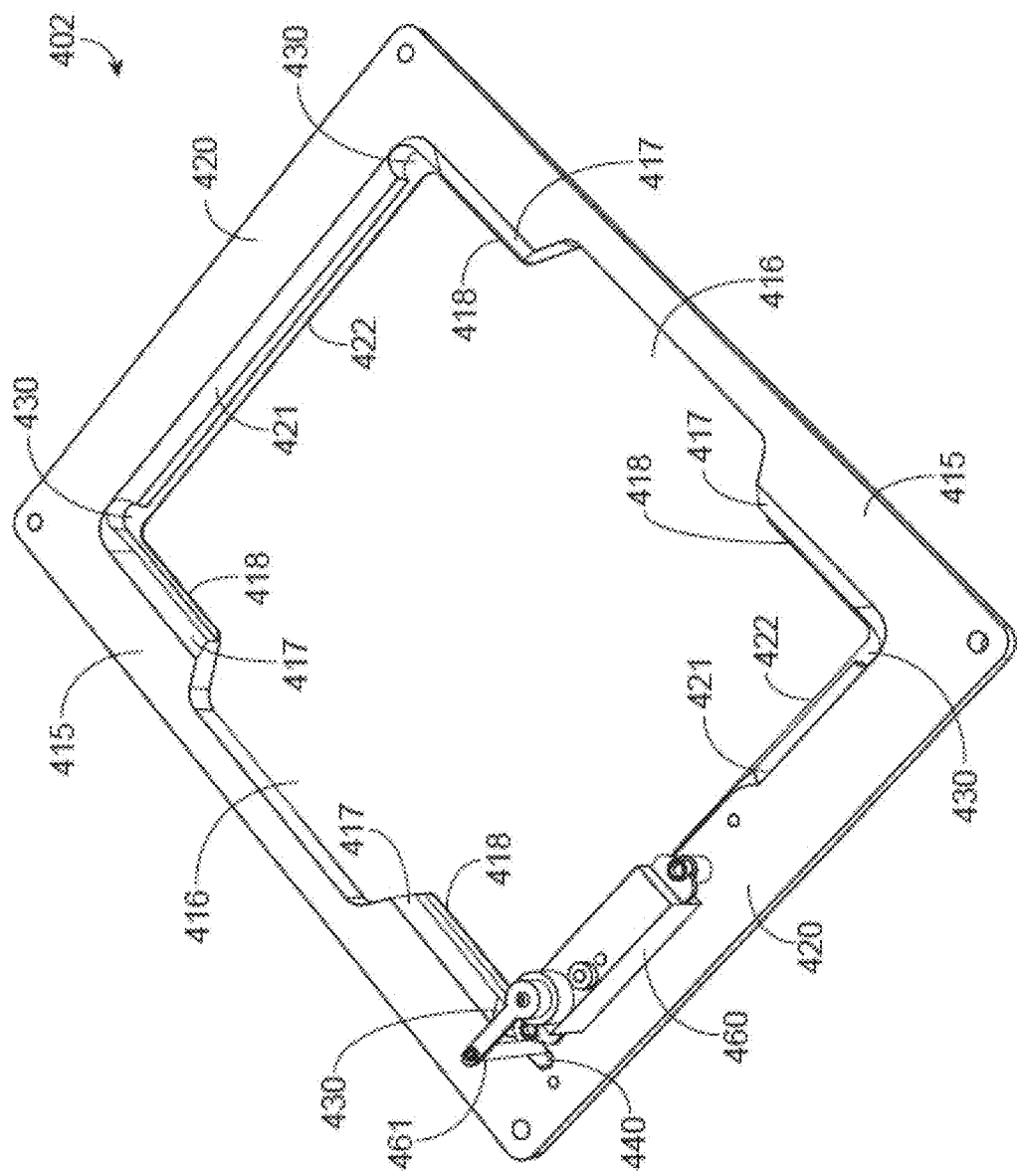
FIG. 17 is a top perspective view of the plate holder and actuator of FIG. 14.
Figure 18:
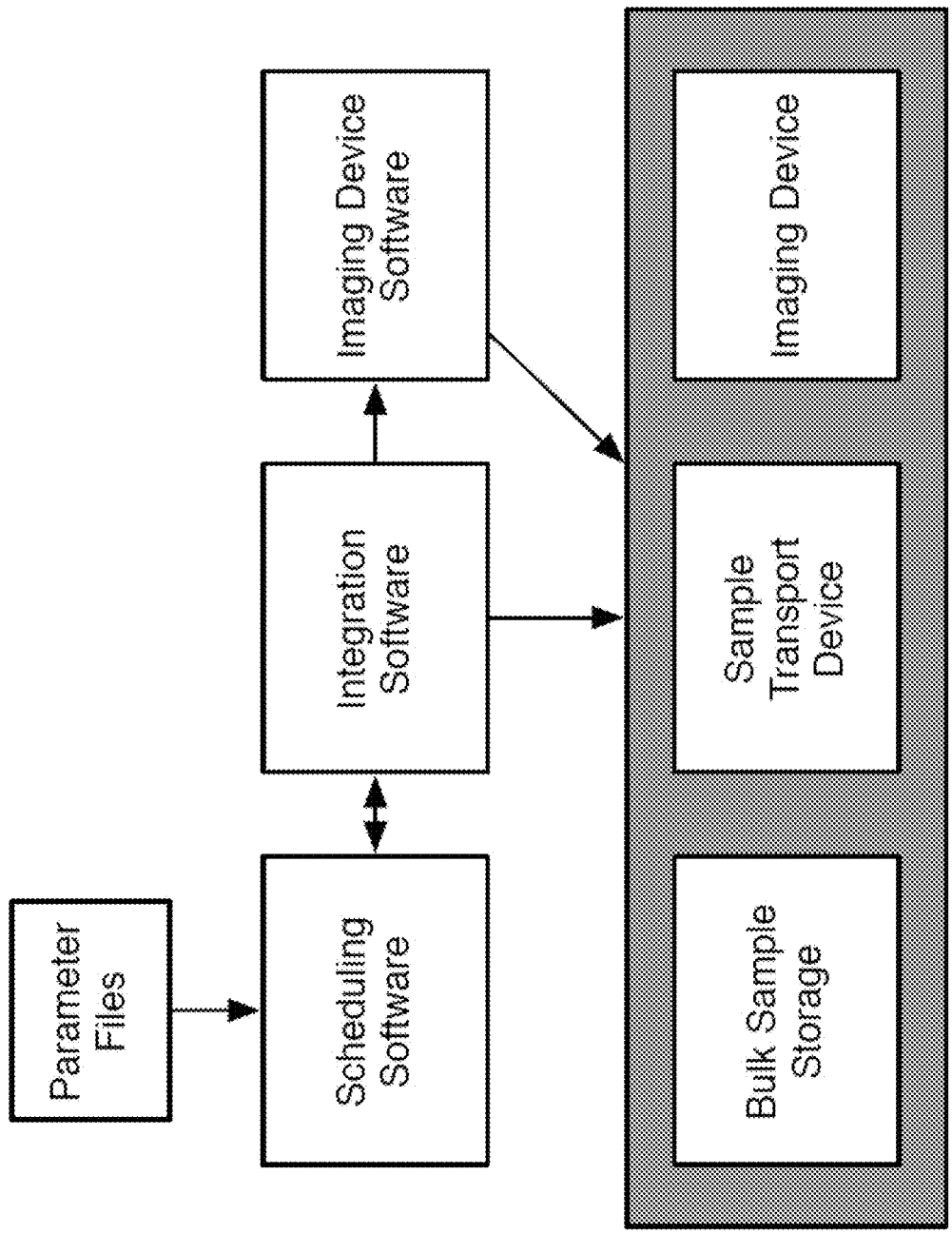
FIG. 18 is a block flow diagram of a process for control of a system of the present disclosure.
Figure 19:
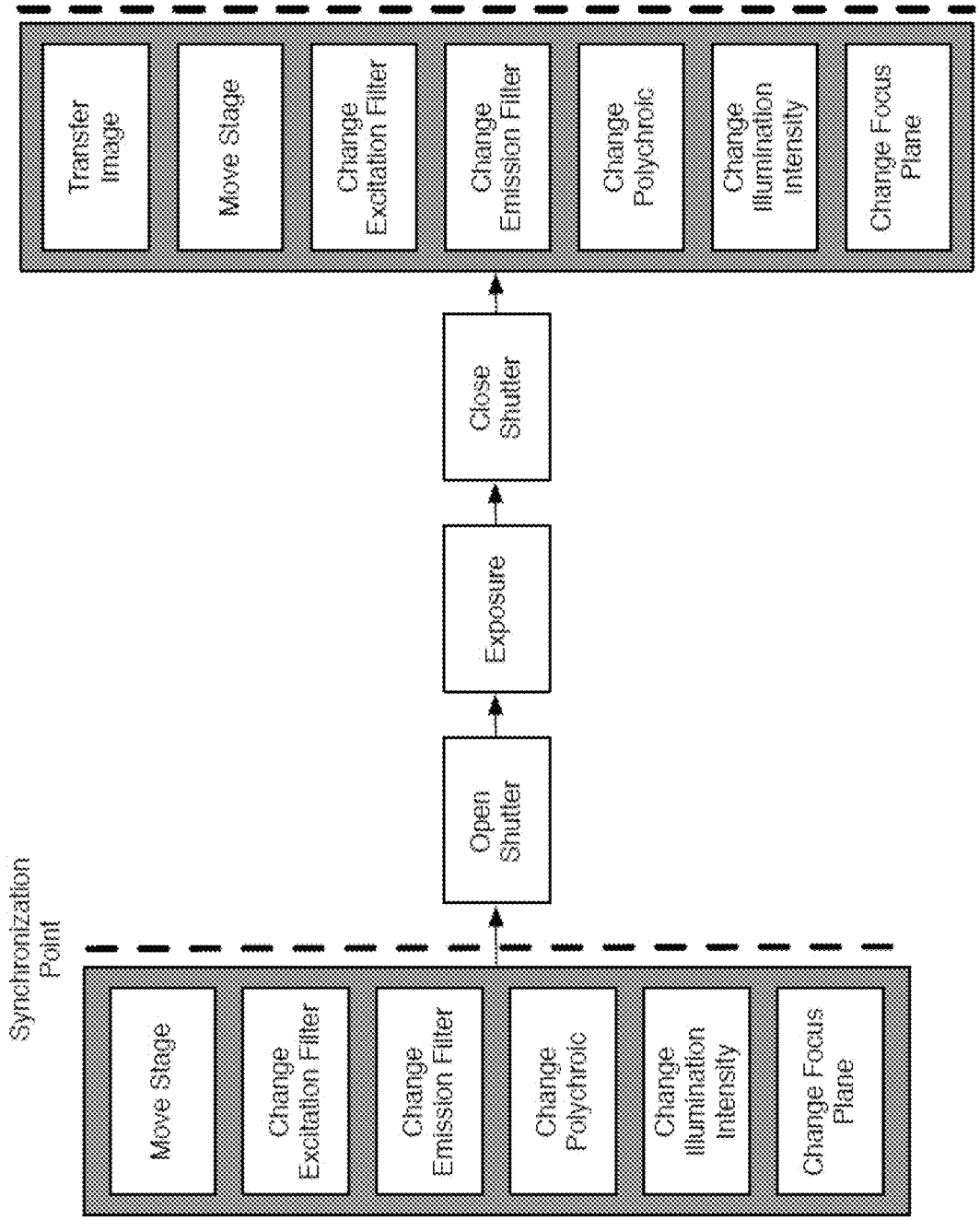
FIG. 19 is a flow diagram depicting an image acquisition process according to some embodiments of the present disclosure.

For example, FIG. 14 is a top view of a plate holder 402 with an electronically controlled actuator 460 installed. The electronic actuator 460 includes an arm 461 and a control unit, and the plate holder is provided with a space (440), e.g., a carved out space, for the placement of the arm 461. This allows the arm 461 to be completely retracted out of the way as the sample plate is deposited and/or removed by the robotic arm. These components are best seen in FIG. 17, which is a top perspective view of the plate holder 402 and actuator 460 of FIG. 14. The control unit includes a motor which, when so instructed by a processor, causes the arm 461 to rotate in a clockwise direction. The arm 461 thus pushes a sample plate positioned in the internal sample plate receiving area into a consistent corner of the internal sample plate receiving area each time a sample plate is positioned in the internal sample plate receiving area, thus securing the sample plate and/or reducing the degrees of freedom of the sample plate. Additional views of the plate holder 402 and actuator 461 are shown in FIGS. 18-19.

Plate Alignment Algorithm

The programming of the present invention allows imaging a biological sample (e.g., cells) and then subsequently returning to and re-imaging that same biological sample at any time interval. Such activity enables study of cause-and-effect relationships in living cells over days or weeks by returning to image the same cells. The invention may use one or more reference marks on a multi-well plate to quickly position the plate in the plate holder on the microscope stage each time the plate is returned to the microscope for imaging. The mark may be one that is consistently set on or into the well plate such as alphanumeric identifiers as element(s) 44 seen in FIG. 4. Alternatively, one or more custom-applied reference points, marks or structures may be employed.

The mark serves as an internal reference for cells on the plate, independent of the position of the plate within the holder. In certain aspects, once a plate is inserted in the holder by the transport subsystem (e.g., as described above), the stage is moved without user intervention to locate a mark in the exact same position as is shown in a previously captured reference image. For example, the stage may be moved without user intervention to the approximate location of the mark by means of computer memory and associated control algorithms. Further, by means of computer memory and associated control algorithms, a reference or fiduciary point for the substrate employed may be located. An imaging step is performed to locate the reference or fiduciary point for the substrate. In certain aspects, a software module is executed by a processor, which directs the imaging device to move the loaded plate to a pre-defined position in X-, Y-, and/or Z-space. This location may correspond to an approximate location of a fiduciary mark, used to locate the plate precisely in space. The location may be refined using a software module executed by a processor, which directs the imaging device to refine the location of the fiduciary mark. Such embodiments may include the use of a scale-invariant feature transform (SIFT) algorithm. In certain instances, a plate alignment algorithm may incorporate an algorithm as described in Lowe D (2004), "Distinctive Image Features from Scale-Invariant Keypoints", *International Journal of Computer Vision* 60 (2): 91-110; and U.S. Pat. No. 6,711,293; the disclosures of which are incorporated herein by reference.

In other aspects, a user may also, or instead, manually move the stage (e.g., with a joystick control 28) to get the mark in the exact same position as is shown in a previously captured reference image, and the acquisition programming is started with the mark in exactly the same position as the reference image (and therefore the same position each time the cells are re-imaged) so that each image in each well is also in the corresponding position.

Returning to a reference mark and finding a position in relation to that mark provides one manner of returning to the same field to observe stationary or substantially stationary cells at separate time intervals. Where more accurate return to a field is desired or required, further refinement of the process is in order. Systems of the present disclosure are able to align images within at least several pixels, even with accuracy to a single pixel or in perfect registration utilizing supplemental mathematical techniques.

In certain aspects, image data obtained may be digitally stored, and converted to a matrix of values. Signals below a threshold value are treated as zeros while others are treated as numerical values (e.g., ones for the sake of simplicity, in which case the matrix will have been binarized). Second or subsequent imaging of approximately the same region (preferably, as generally identified by use of the reference mark(s) as described above) receives the same treatment. Since misalignment of images (as in survivability studies, etc.) to be superimposed via computer software for analysis, results in zeros multiplied against numerical values and greater mismatch of the matrices exacerbates this effect, lower sums for the multiplied matrices represent less aligned positions. Conversely, a peak or spike represents a maximum value of the sum of matrix numbers—indicating full (or at least optimized) alignment.

In certain aspects, second or subsequent imaging of approximately the same region is aligned to prior image(s) using phase correlation to estimate the relative translative offset between the images. Any convenient phase correlation approaches may be employed, including but not limited to those described in Stone H S, IEEE Transactions on Geoscience and Remote Sensing, V. 39, No. 10, October 2001, pp. 2235-2242; De Castro E, et al., IEEE Transactions on pattern analysis and machine intelligence, September 1987; and Reddy B S, et al., IEEE Transactions on Image Processing 5, no. 8 (1996): 1266-1271; the disclosures of which are incorporated herein by reference.

It may in some instances be preferred to utilize a subset (e.g., the central 80%) of the matrices in the registration process. Such an approach helps avoid situations where a portion of one matrix is not represented in the other matrix (and therefore would not contribute to the sum to identify a local maximum—unless the matrices were already identical/aligned) and the potential for unpredictability associated with the same. This may be useful in embodiments that do not incorporate SIFT (described above), which is able to align even with partial overlapping. Furthermore, taking a subset of the available matrix values lowers computational requirements.

Note that even smaller matrices than the exemplary 80% approach may be employed—at least to roughly align images. By further reducing the computation demand on the system (by utilizing smaller matrix subsets), it becomes increasingly feasible to attempt registration of larger sampled areas. Also, with reduced computational demands, it will in some cases be possible to register images that are coarsely aligned (e.g., initially aligned without involving the reference mark approach).

Such action is followed by an imaging step. Preferably, a phase contrast image is produced. However, fluoroscopic imaging of the cells may be employed. In any case, the image is ultimately superimposed with a previous image that is likewise imaged in relation to the reference point. The superposition is preferably accomplished using a matrix registration technique as described above in which the highest sum of the product of two matrices (or matrix subsets) representative of the pixel values is sought. In instances where the information utilized for registration is a phase contrast image, it should be paired for registration with another such image previously provided. The use of phase contrast images over fluorescent-based images is preferred because little, if any, difference should be presented by the phase contrast images.

When registration is performed in connection with one image and subsequent imaging follows, these latter-produced images will be aligned or superimposed as well. While it may be preferred to conduct subsequent scans/imaging in such a manner and the computer processor directs stage movement (generally X and Y-axis movement) to align the images that no post computer processing is required to align them, an alternate approach is to perform registration of the images after all imaging is complete (i.e., off-line). That is to say, stored image data can be aligned using the matrix approach described. Usually, use of a reference point or stored reference position will still be desired for rough alignment, to be followed with fine alignment performed with the matrix method. Accordingly, both on-line and off-line registration techniques are taught hereby.

In an exemplary implementation of this aspect of the invention, computer programming directs taking two pairs of images. It directs taking a first phase contrast image and first fluorescence image, then directs movement of the system's fluorescence emission filter wheel, followed by taking a second pair of phase and fluorescence images. Because movement of the filter wheel may be the cause of image misalignment in the referenced system, each pair of phase and fluorescence images (collected while the wheel is stationary) are aligned. However, the first and second image pairs may be misaligned/misregistered with respect to the other, e.g., due to perturbation of the system caused by movement of the filter wheel. The misalignment, when present, may be corrected automatically via computer control employing the matrix methodology described above utilizing matrices derived from the more comparable phase contrast images that correspond to the fluorescent images—at least in terms of their registration. In other embodiments, movement of the filter wheel does not cause perturbation of the system and corrective alignment as described above is unnecessary.

Camera

Returning to FIG. 3, an imaging system may include a camera 14. In some embodiments, the camera is preferably placed directly beneath the microscope body to eliminate the need for an extra mirror within the microscope body that could reduce the amount of emitted light.

In certain aspects, the camera is a CCD camera. Aspects of embodiments may include an Electron Multiplying CCD (EMCCD) camera, such as an Andor EMCCD iXon3 888 CCD camera. Cameras of interest further include, but are not limited, to, Andor EMCCD iXon3 860, iXon3 897, and iXon3 Ultra 897 Ultra CCD cameras. An EMCCD can enable a large field of view and high quantum efficiency of light to electron conversion across a broad part of the spectrum. The camera can also be a CMOS camera such as an Andor Neo 5.5 or Zyla 5.5 A CMOS camera enables collection of a large field of view while imaging at high frequency (100 fps) to study more rapid biological processes.

Cameras for use in imaging systems of the present disclosure preferably have an exposure of 100 ms or less when reading out the full sensor, such as 50 ms or less, including 30 ms or less, 20 ms or less, 10 ms or less, or 5 ms or less. In some embodiments, cameras for use in imaging systems of the present disclosure preferably have an exposure of 100 ms to 5 ms, e.g., 50 ms to 5 ms, 30 ms to 5 ms, 20 ms to 5 ms, or 10 ms to 5 ms.

In certain aspects, cameras for use in imaging systems of the present disclosure contain 1M active pixels or more, such as 1.5M or more, e.g., 2M or more, 2.5M or more, or 3M or more. In certain aspects, a pixel corresponds to an actual physical dimension of about 0.3 µm. Further, in certain aspects a camera used in imaging systems of the present disclosure include a sensor area of 150 mm$^2$ or more, such as about 150 mm$^2$ to about 175 mm$^2$, about 175 mm$^2$ to about 200 mm$^2$, 200 mm$^2$ to about 225 mm$^2$, about 225 mm$^2$ to about 250 mm$^2$, about 250 mm$^2$ to about 300 mm$^2$, about 300 mm$^2$ to about 400 mm$^2$, about 400 mm$^2$ to about 500 mm$^2$, about 500 mm$^2$ to about 750 mm$^2$, about 750 mm$^2$ to about 1000 mm$^2$, or about 1000 mm$^2$ or more.

In certain aspects, acquiring an image of the sample comprises deconvolving a multi-wavelength image into its component wavelengths. Any convenient means of performing such deconvolving may be employed, with approaches of interest including, but not limited to, those described in T Zimmerman, et al. *FEBS Letters* 546: 87-92 (2003); M E Dickinson, et al. *Journal of Biomedical Optics* 8: 329-338 (2003); Y Hiraoka, et al. *Cell Structure and Function* 27: 367-374 (2002); T Zimmerman. *Advances in Biochemical Engineering/Biotechnology* 95: 245-265 (2005); J M Lerner and R M Zucker. *Cytometry A* 62: 8-34 (2004); R Lansford, et al. *Journal of Biomedical Optics* 6: 311-318 (2001); R A Neher and E Neher. *Journal of Microscopy* 213: 46-62 (2003); Y Garini, et al. *Cytometry A* 69: 735-747 (2006); R M Levnson and J R Mansfield. *Cytometry A* 69: 748-758 (2006); R H Berg. *Journal of Microscopy* 214: 174-181 (2004); C. Spriet, et al. *Microscopy Research and Technique* 70: 85-94 (2007); C. Thaler, et al. *Biophysical Journal* 89: 2736-2749 (2005); D. Megias, et al. *Microscopy Research and Technique* 72: 1-11 (2009); and Y. Chen, et al. *Journal of Microscopy* 228: 139-152 (2007); the disclosures of which are incorporated herein by reference. For example, in certain aspects, such deconvolving is implemented by line scanning method that uses a vertical illumination slit and grating to disperse the emitted light along the horizontal dimension of the CCD. In this case, the CCD is read out as a full image for each slit location with spatial resolution along the vertical dimension and spectral resolution along the horizontal dimension. An alternative implementation is having multiple CCDs to simultaneously capture emitted light. In this case, a series of filters is used to direct emitted light of certain wavelengths to the different CCDs. With either implementation, linear unmixing can be used to further deconvolve overlapping spectra if the spectrum of each probe in the sample is known.

Light Source

Systems of the present disclosure may include a light source having a broad spectral output. In certain aspects, the light source includes a Xenon light source 22 and a fiber optic 24. Light sources of interest further include, but are not limited to, LED/solid state light sources and lasers.

In certain aspects, the output of the light source is adjustable. Aspects of systems include automated output adjustment. In certain embodiments, a control processor is configured to adjust the output of the Xenon light source 22. In certain aspects, the output is tailored for a particular sample. For example, a processor may be configured to identify a sample (e.g., using the sample identification subsystem), which includes one or more parameter files to be read (see, e.g., FIG. 18). One such parameter that may be read by the processor may include the output level of the light to be applied when imaging the sample. The processor may be in communication with the Xenon light source 22, either directly or via imaging device software, to provide such control.

In certain aspects, a light source may include a filter wheel. Where a light source contains a filter wheel, each filter position may be associated with a specified intensity level. The specified intensity level may be automatically selected when a filter is called.

Embodiments of systems of the present disclosure may include Xenon light sources having an output range of about 200 nm to about 800 nm, including about 300 to 700 nm.

In certain aspects, the Xenon light source may be Lambda XL light source, such as a Lambda XL light source with an integrated 10-B controller for filter wheel and Smartshutter (Sutter Instrument Co.).

Optical Filters

An imaging system may include one or more filters. In certain aspects, the filters may be present in a filter wheel 10 or filter wheel and shutter combination 20. The filter wheels 10 or filter wheel and shutter combination 20 may be placed between the light source 22 and the camera 14.

Filters that may be used in aspects of the present system include single-band bandpass filters, edge filters, bandpass clean-up filters, notch filters, dichroic beamsplitters, polarizing filters, and the like.

Filters may be selected to correspond to one or more fluorophores that may be present in a sample. Examples of such fluorophores include, but are not limited to, indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like.

In certain aspects, the filters are commercially available filters (e.g., Semrock Brightline filters). Filters may be specially coated to deal with high output of the light source 22. The specific wavelengths of the filters, the number of the filters, and other variables may vary based upon, for example, the particular type of sample being imaged, the specific fluorescence channel(s), and other factors known to those of skill in the art.

Automated Focusing

In certain aspects, automated focusing includes an automated focusing component, such as that provided by the Nikon TiE Perfect Focus System (PFS) which utilizes the reflection of LED generated long-wavelength light (e.g., 870 nm) on the bottom of a sample plate to determine the distance from the tip of the objective to the bottom of the sample plate. This allows the system to automatically correct for mechanical and thermal induced variations in sample plate position. Utilization of the long-wavelength LED enables the PFS to be used with a large variety of fluorophores emitting in the wavelength range between 340 and 750 nanometers.

In other aspects, commercial imaging software from Metamorph (Universal Imaging Corporation (UIC)) or customized software provides software drivers that are able to automatically focus the microscope via stage controller 40. The drivers send signals to motors that control an X-Y stage position and a Z-axis focus knob 42. Stepper motors may be employed to automate such movement (not shown). Generally, to focus an image that is collected by the system optics, a fast-Fourier analysis is performed to measure the spatial frequency of the image, and then the computer moves the Z-position and repeats the analysis at a new depth. A local maxima in spatial frequency is determined which corresponds to the focal plane. As referenced above, transmitted light (rather than epifluorescence images) is preferably used for focusing because reduced light exposure intervals are required (which limits phototoxicity) and fast acquisition times. The CCD camera resolution can be reduced during image acquisition for determination of the focal plane to increase speed. This provides up to a 100-fold improvement in acquisition speed and substantial reduction in phototoxicity.

Embodiments include the use of both the Perfect Focus System (PFS) and the Z-plane focusing described above. Such embodiments may be useful when using samples (e.g., multi-well plates) with thin bottoms, especially if a long focal length objective is used. In certain embodiments, PFS may find it difficult and/or impossible to get a 'lock.' Accordingly, in such embodiments Z-plane focusing may be employed followed by PFS, thereby enabling PFS to get a 'lock' and making the system more robust.

Imaging Modalities

In some embodiments, a system as described herein can operate in one or both of two different imaging modalities: wide-field fluorescent microscopy and confocal microscopy. Wide-field microscopy allows a user to collect images in two dimensions at each time point. With the addition of confocal microscopy, three-dimensional images can be collected at each time point. In some embodiments, for example, a Yokogawa CSU-W1 spinning disk confocal can be attached to the right port of a microscope as described herein for collection of three-dimensional images (XYZ) at each time point. In such embodiments, the final images collected with the system are in four dimensions (XYZT) where T=time. This allows for collection of new features in samples relative to previous systems. In some embodiments, while utilizing the confocal modality, six laser lines are used for excitation of fluorophores at six different wavelengths simultaneously. For example, it is possible to image live zebrafish embryos, brain slices, and more complex organoids made from stem cells or any structure that has a three-dimensional structure whereas, with wide-field microscopy alone, the system is limited to two-dimensional structures such as monolayers of cells that are relatively flat. The CSU-W1 confocal is equipped with 2 scientific CMOS Zyla 4.2 cameras that collect light in two different channels simultaneously. This hardware, when implemented with suitable software, allows for the collection of faster time-lapse images at each imaging interval. This allows, for example, for the collection of fast time-lapse images on a first day, return to, e.g., the same cell on a subsequent day, and collection of another set of fast time-lapse images (e.g., every 10 seconds for 20 minutes) of, e.g., the same cell.

The fast time-lapse imaging capability allows for user-controlled scheduling and time-lapse control with images taken every 10 seconds or less, e.g., every 5 seconds. For example, seven scheduled time-points can be taken 24 hours apart, with each time-point including 120 images taken every 5 seconds.

Figure 27:
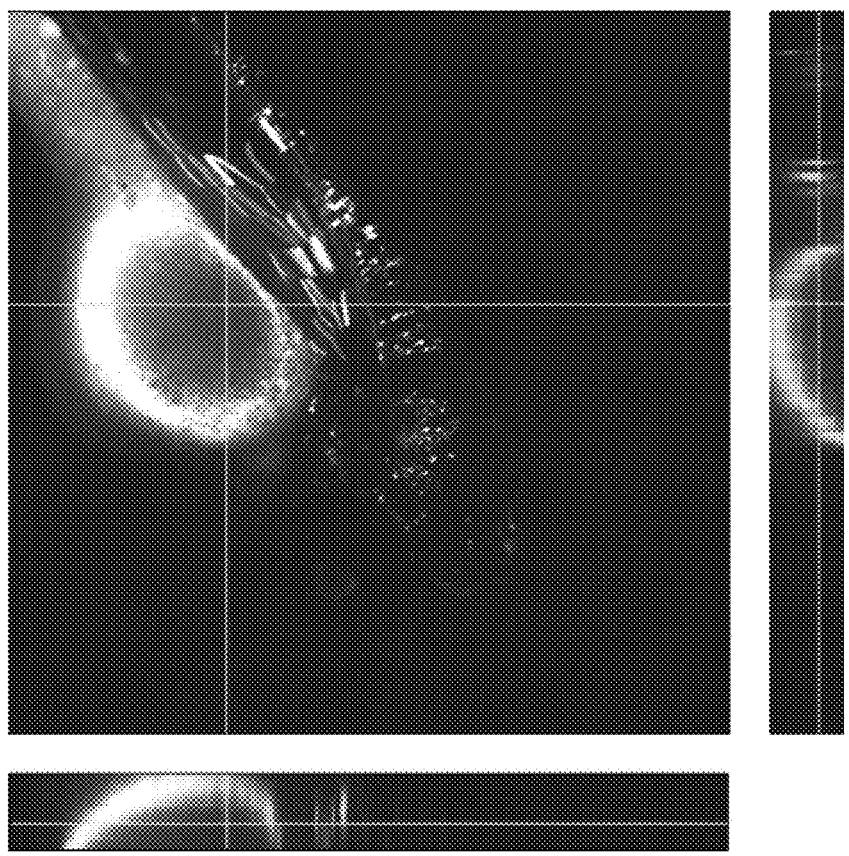
FIG. 27 shows an orthogonal projection of a three-dimensional image of a Zebrafish embryo. The larger panel represents the XY axes while the two thinner panels on the sides and bottom represent the XZ and YZ planes, which show the three dimensional structure. The height of the stack is 150 µm with each image plane representing a 3 µm thick slice.

A discussed above, 3-D images can be produced with the Yokogawa CSU-W1 spinning disk confocal. The Spinning disk performs confocal imaging, removing all out of focal plane light, while also multiplexing the acquisition across the surface of the camera sensor, allowing a high speed acquisition of single focal planes. When the confocal is used in combination with a high precision piezo Zstage (PZ-2150), these focal planes can be stepped through the sample, producing a series of images which can then be reconstructed to form a three-dimensional image. These features can be incorporated into a system as described herein, allowing several time-points, over several days or weeks to be acquired, thereby creating a 4-dimensional image (X,Y, Z,T). By way of example, FIG. 27 shows an image acquired utilizing the Yokogawa CSU-W1 spinning disk confocal in combination with a high precision piezo Zstage (PZ-2150). The large panel shows the image of one focal plane (Nikon CFI Plan Apo Lambda 10X) with the thinner panels on the side and bottom showing the collection of imaging planes collected. The white lines in each panel show the location of each image plane respectively.

Figure 28:
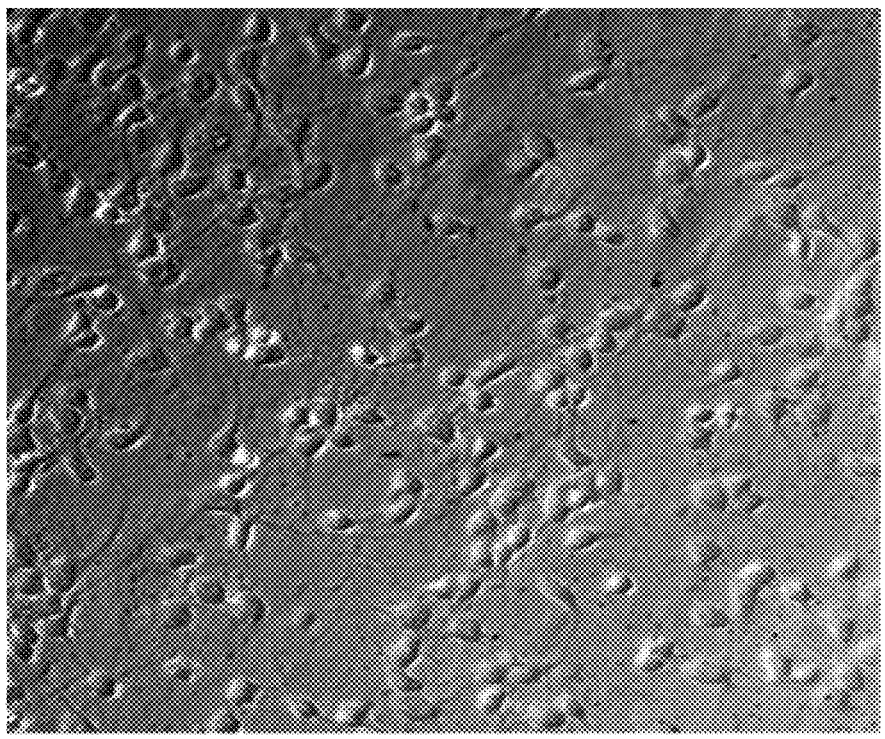
FIG. 28 shows a representative phase contrast image. The phase contrast images are acquired using an objective and condenser aperture. These optical elements enhance or attenuate the light passing through the sample based on a phase shift caused by light passing through inhomogeneous refractive indices. This enhancement and attenuation based on the phase shift, greatly increases the contrast of the image, making small details more accessible. The implementation of these elements can be specified by a user.

In some embodiments, phase-contrast objectives and filters and a motorized condenser can be integrated into a system as described herein to collect phase contrast images. This allows for the capture of phase contrast images of, e.g., the same cells in longitudinal images. By way of example, the image in FIG. 28 was acquired using a 40× phase objective from Nikon (CFI S Plan Fluor ELWD ADM 40×) in combination with a phase 2 aperture (Nikon Ph2) mounted in the motorized condenser. When these two elements are used together, they allow for automated, phase contrast imaging in the same imaging session as Epifluorescence or confocal imaging, increasing the amount of information acquired, e.g., from each well.

Software Control of Peripherals

As described above, a system may include one or more processors configured to control the system and/or subsystem. In certain aspects, the processor(s) may execute instructions from one or more software modules to cause the system or subsystems thereof to facilitate bulk sample storage, to remove and/or identify a specific sample from bulk sample storage, to place a sample on an imaging device, to align a sample on an imaging device, to image a sample, to place a sample into bulk sample storage, and/or to process image(s) taken of a sample.

FIG. 18 presents a block flow diagram of a process for control of a system of the present disclosure. In this embodiment, one or more parameter files are read by scheduling software (e.g., custom written software from BioSero Inc.). The parameter files may be tailored for a specific sample type, wherein a sample identification subsystem is used to identify a particular sample, and a processor is configured to identify the specific parameter file(s) for that sample.

Accordingly, the handling, imaging, and/or image processing may each be tailored for a particular sample. Where samples present on multi-well plates, each well of that multi-well plate may itself have specific parameter file(s) that specify the handling, imaging, and/or image processing for one or more individual wells. For instance, a usage for multi-well plates may involve a drug and/or genetic screen where only a single condition such as a drug or genetic modifier is altered in each well in order to determine its affect on the measured outcome. This experiment may involve identical imaging parameters in each of the measured wells since it is effectively the same experiment in each well. An alternate usage enabled by systems of the present disclosure would be to use each well or a group of wells to carry out experiments unrelated to other wells or groups of wells. These experiments may differ in more ways than a screen normally does such as the cell type being measured, the imaging area covered, the biosensors measured, or the frequency of imaging. The ability to adapt each well to experimental requirements has several advantages, such as (i) increasing the number of experiments which can be carried out without the cost of selecting sub-optimal imaging parameters due to the constraints of adjacent experiments; (ii) reducing material costs by reducing the number of plates necessary for a given number of experiments; and (iii) allowing for experiments to adapt to uncertain and irregular access to cells. For instance, iPS (induced pluripotent stem) cells require weeks to months to mature to a particular cell-type. It is common for some wells to be lost due to cell death or poor differentiation, but it is not easy to predict how many. Being able to carry out several experiments on a single plate allows the experimenter to adapt the investigation to the number and quality of available wells.

Moreover, in certain aspects timepoint-specific imaging parameters can also, or instead, be used if there is an initiating optical stimulus required for the experiment or if there are different stages/question being asked during the experiment which require different imaging parameters. For instance, an optical-pulse chase experiment which relates the rate of turn-over of a photoswitchable protein within a cell to the survival of the cell nicely demonstrates both points. In order to label a population of photoswitchable proteins, a pulse of short-wavelength light is applied at the first timepoint of the experiment. The next several timepoints may be carried out with high frequency and imaging in multiple channels to track the both the cell and the amount of photoswitched protein within the cell. The survival of the cell is normally carried out with much lower frequency and imaging just the morphology marker of the cell to track cell death.

Embodiments of systems and methods of the present disclosure include performing runtime analysis used to control the handling, imaging, and/or image processing of one or more samples. For instance, in certain embodiments an area is scanned—or images are collected—until a certain number of objects have been imaged, where the number of objects may be a user-defined parameter. Analysis of the images during the experimental run enables an interactive runtime which can alter imaging parameters in response to experimental requirements. Examples of these requirements include, but are not limited to, a certain minimum number of cells imaged for statistically relevant comparisons between conditions, a certain range of cellular fluorescent intensities which are within the linear range of the camera, or a time consuming imaging protocol which would be impractical to carry out at every position imaged on a plate such as imaging every second for several minutes to study dynamics or high-resolution spectral imaging. In certain aspects, one or more parameters (e.g., imaging parameters, such as the filter(s) applied or the frequency of imaging) may be altered when a certain object is imaged and detected.

Turning again to FIG. 18, the scheduling software may interface with integration software, which is in communication with one or more components of the system. The integration software may include an interface to the driver(s) for a given component, causing it to take one or more actions as determined by the parameter files and scheduling software. Further, the integration software may interface with imaging device software (e.g., μ-Manager software) to control the imaging device. As appreciated by one of skill in the art, the particular means of connecting software modules (e.g. through an application programming interface (API)) will be dictated by the particular software modules employed. In certain aspects, the means for connecting software modules may include a client/server relationship, wherein one module (e.g., the scheduling software) acts as the server, issuing instructions to one or more clients (e.g., the imaging device software).

In certain aspects, software (e.g., the scheduling software) may be used to manage runtime conflicts. Runtime conflicts may occur, for example, where a system includes a plurality of samples, a plurality of imaging devices, a plurality of transport devices, a mix of different sample types, and the like. In certain embodiments, the scheduling software determines the runtime for a sample by start time and/or priority. For example, every experiment may be initially programmed with (i) start time(s) and/or (ii) duration. When an experiment is entered into the scheduling program, such as by a user, a priority may be assigned. The scheduling software may determine the next sample (e.g., a plate, such as a multi-well plate) to run based upon the following algorithm:

1. List the samples to be run in order of start-time. The list may include samples which have a start-time that has already past but has not yet been sent to a microscope.
2. Using the duration of each experiment, determine which experiment(s) would conflict at any point from the start to end of the experiment.
3. If an experiment conflicts with another experiment which has a higher priority, then remove it from consideration as the next sample to run. Optionally, include a function which increases the priority of an experiment based on the amount of time which has elapsed since the scheduled start-time. This ensures that even low priority samples will eventually be run.
4. The first item on the list is then the highest priority experiment within the context of adjacent experiments that can fit within the time before the start of another experiment of greater priority. Run that first experiment.

In other aspects, the scheduling software may also, or instead, utilize a calendar to determine conflicts. Experiment start times and duration are mapped to a calendar, such as a calendar represented as a horizontal line. Experiments which conflict at any point from the start to end of the experiment are signaled by placing one of the conflicting experiments on a horizontal line below the standard line.

In certain aspects, process control includes one or more instructions that are issued in parallel. FIG. 19 presents an embodiment in which instructions are issued in parallel and/or substantially at the same time. In this embodiment, the integration software and/or imaging device software cause a processor(s) to move the microscope stage, change the excitation filter, change the emission filter, change the polychroic, change the illumination intensity, and change the focus plane of the imaging device at substantially the same time. Because such operations may take varying times, the system may pause (e.g., have a synchronization point) to allow for at least the slowest operation to be complete. After this synchronization point, the system may cause the shutter to be opened (e.g., for a defined period), exposed, and closed. Upon causing the shutter to close, the system may again perform several operations in parallel and/or at substantially the same time, including transferring the image, move the microscope stage, change the excitation filter, change the emission filter, change the polychroic, change the illumination intensity, and change the focus plane of the imaging device. Once stored, the image may be subjected to additional processing, such as described below.

Systems of the present disclosure may produce a notification/alarm, with such notifications or alarms produced using hardware, software, or a combination thereof. For example, systems may include one or more sensors that monitor (e.g., continuously or discretely monitor) factors such as system power, environmental control (e.g., temperature, $CO_2$ concentration inside the bulk storage subsystem, etc.), and the like. To ensure continuous power, a system may include one or more uninterruptible power supplies (UPS) to bridge house power to the system (or a subsystem thereof) and serve as an immediate power source until backup generators are started. In the event of a power outage, the system may be configured to send notification to responsible parties by any convenient means, such as by text and/or email. Moreover, systems may include hardware and/or software configured to monitor system performance and health and to store such information non-transiently, such that fluctuations in system conditions (e.g., environmental control) can be linked to experimental changes observed.

Image Processing

In certain aspects, the systems of the present disclosure may include one or more processors configured to process an image acquired as described above. As shall be detailed below, such processing may include one or more of the following: organize the images for a particular sample; stitch two or more images for a particular sample together; align images; identify objects (e.g., cells, such as neurons) within an image; track an object (e.g., a cell, such as a neuron) through a temporal series of images; extract data (e.g., fluorescence data) from objects identified within an image; and/or analyze the resulting images.

Systems of the present disclosure may employ a single pipeline approach, in which each subsequent step in the pipeline is acting on the resulting images from the previous step. Systems may also, or instead, employ multiple pipelines of image analysis, e.g., 2 or more, 3 or more, 4, or more, 5 or more, or 10 or more. That is, in certain aspects several pipelines all act on the original image(s) and combine the resulting image(s) from each pipeline to create a result, such as segmented regions. In addition or alternatively, these multiple pipelines may also have iterative or sequential components such that the information gained from one pipeline is used in the preprocessing step of the same or another pipeline.

Figure 25:
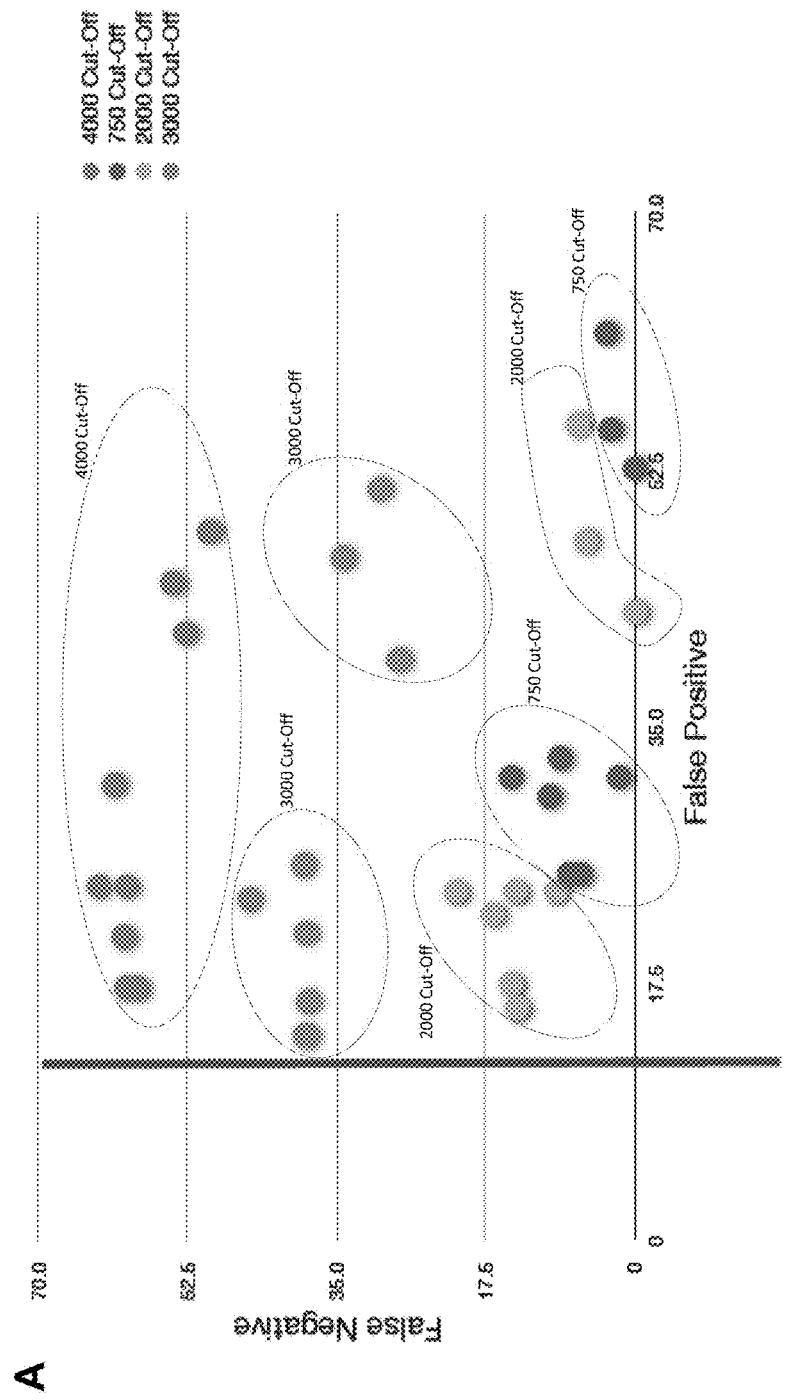
FIG. 25, Panels A-B show the improvement in segmentation when combing the results from more than one segmentation pipeline. Panel A: a plot showing false positive and false negative rates from a pipeline of just intensity measurement using various threshold of intensity to segment the cells. Decreasing the false positive rate by increasing the intensity threshold results in a substantial increase in the false negative rate. Panel B: plot showing false positive and false negative rates using a fixed intensity threshold combined with spatial segmentation (minimum area threshold) using one of several spatial bandpasses. The use of intensity and spatial segmentation results in improved specificity without sacrificing sensitivity as shown by the decrease in false positive rates without an increase in the false negative rate.
Figure 25:
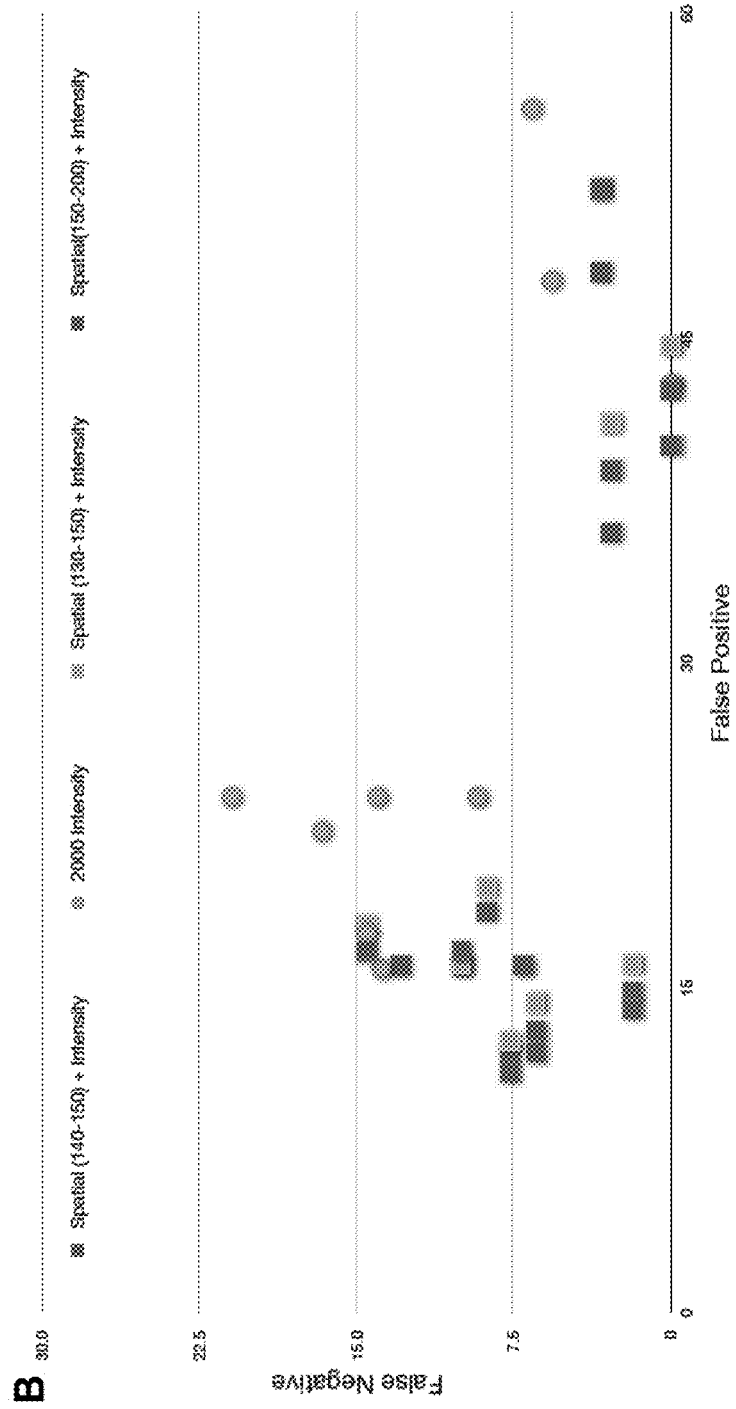

For example, a sample (e.g., a sample that likely includes a cell, such as a neuron) may be imaged by a plurality of imaging pipelines, where the results of each are combined to classify the sample. For instance, a sample including a neuron may be imaged using first, second, and third pipelines employing first, second, and third imaging systems, respectively, and first, second, and third parameter files, respectively, each pipeline classifies an area as a neuron or not. There are several benefits to parallel rather than consecutive pipelines, including (i) each pipeline can have less strict parameters (which helps to keep the false negative rate low) without adversely increasing the false positive rate; (ii) more complex negative filters (in contrast to simple limits such as area min/max) which detect characteristics that should never or rarely be present in the segmented cell type can be used; and (iii) filters which are not particularly sensitive but are reliable indicators of neurons or non-neuronal cells can be used in fuzzy combination as described below. FIG. 25, Panels A-B illustrate that such an approach to segmentation, using intensity and spatial segmentation, results in improved specificity without sacrificing sensitivity.

The individual results from the individual pipelines may be combined using any convenient method, such as absolute classification (e.g., requiring positive identification of an area as a neuron by all pipelines for the object to be classified as a neuron), or fuzzy classification (e.g., via voting and/or a weighted combination of the results of the individual pipelines). Such combinations and classifications may involve applying one or more statistical or learning machine algorithms, such as genetic algorithms, neural networks, hidden Markov models, Bayesian networks, support vector machines, and the like. In certain aspects, segmentation of an image resulting from the aforementioned absolute or fuzzy combination can be done using one of at least two methods: contours on the final binary image or overlap of the final binary image with a segmentation which more fully outlines the desired cellular morphology. While parallel pipelines may more accurately determine whether a cell is of the proper cell type, the combination may not accurately reflect the desired total area or sub-region of the cell. Thus, a previous or other segmentation such as intensity segmentation can be used as the contour if the area within the intensity segmentation contains a sufficient number of positive pixels from the final combined image.

In certain aspects, image processing includes application of one or more machine vision algorithms. Examples of machine vision algorithms of interest include, but are not limited to, those described in Jain, Ramesh, Rangachar Kasturi, and Brian G. Schunck. *Machine vision*. Vol. 5. New York: McGraw-Hill, 1995; Sonka, Milan, Vaclav Hlavac, and Roger Boyle. "Image processing, analysis, and machine vision." (1999); Davies, E. Roy. *Machine vision: theory, algorithms, practicalities*. Morgan Kaufmann, 2004; and Hornberg, Alexander, ed. *Handbook of machine vision*. Wiley-VCH, 2007; the disclosures of which are incorporated herein by reference.

Image Organization

In certain aspects, a processor is configured to execute one or more software modules to organize the image file(s) for a given sample. Software modules may perform one or more of the following organization tasks: renaming of file names, creation of one or more directories, automated conversion of one file type to a different file type, or up- or down-conversion of the image(s).

Figure 20:
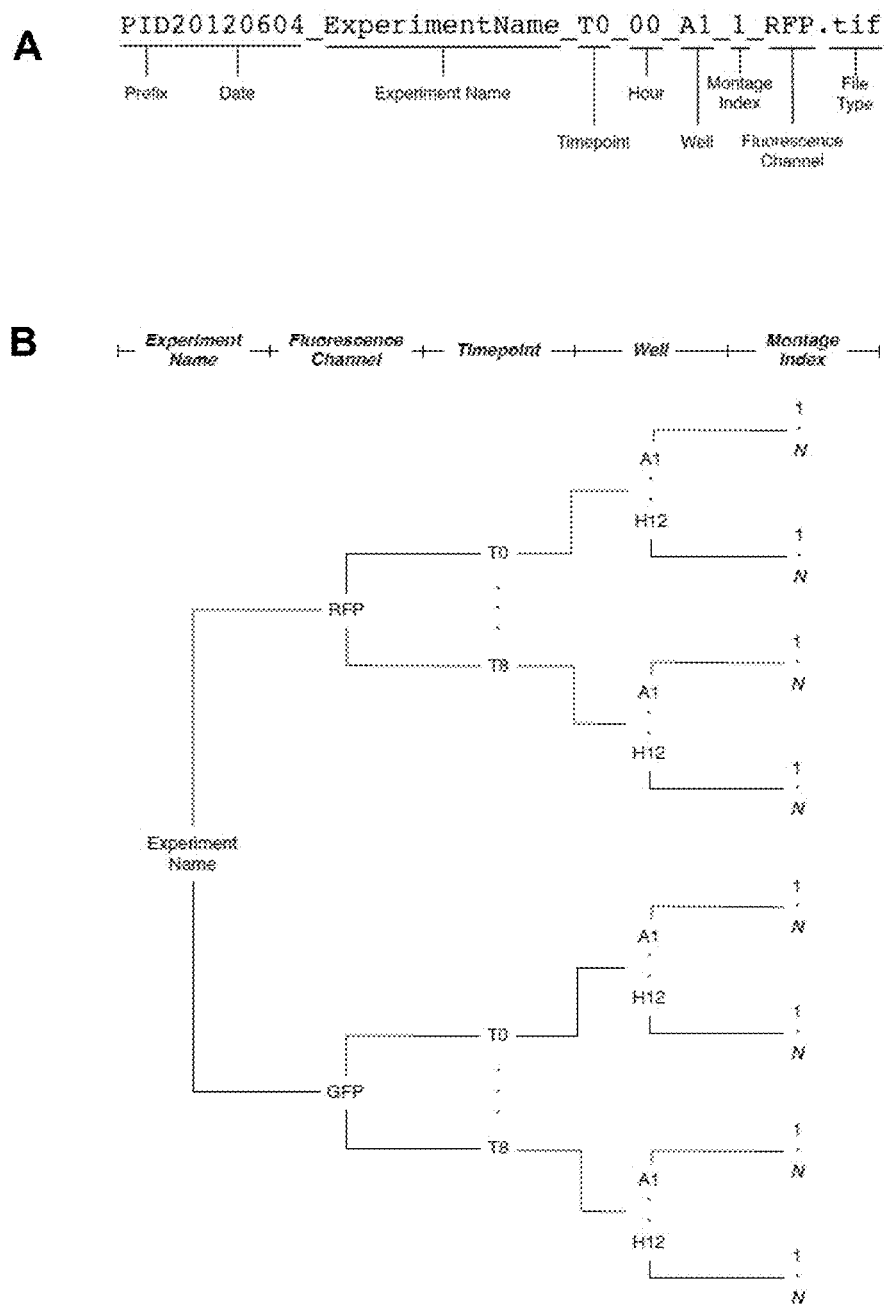
FIG. 20, Panels A-B illustrate the image organization of certain embodiments of the present disclosure. Panel A: Images may be given a file name that includes information about the date of acquisition, experiment name, timepoint, hour, fluorescence channel, well, montage index, and file type. Panel B is an illustration of an organization scheme for image files.

In certain aspects, a software module identifies files in a user-defined path having a user-defined prefix and/or suffix. FIG. 20, Panel A presents a non-limiting example of a file name having a user-defined prefix and suffix. Here, the image file has been created with a name that provides information about the date of acquisition, experiment name, timepoint, hour, fluorescence channel, well, montage index, and file type.

Using the example from FIG. 20, panel A, a software module (e.g., a script, such as a Perl script, Python script, and the like) may be configured to cause a processor to identify all file types in the user-defined path having the prefix "PID" and/or the suffix ".tif". The names of such files may be parsed, such as by using a regex engine (e.g., a Perl regex engine). Once parsed, the processor may create a multi-tiered file organization structure, such as that illustrated in FIG. 20, panel B. In this example, a directory having the experiment name is created in a user-defined path, if the directory is not already created. Within that directory, a separate sub-directory may be created for each fluorescence channel of the experiment (e.g., "RFP," "GFP," etc.). Within each fluorescence channel sub-directory, a sub-directory may be created for each timepoint that is recorded (e.g., T0, T1, . . . T8). A sub-directory may be created for each timepoint, in which separate sub-directories are created for each well(s) of the sample. For example, for a 96-well plate, a total of 96 sub-directories may be created for each timepoint, corresponding to wells A1, A2, . . . H10, H11, and H12. For each well, a separate sub-directory may be created, in which the images for each montage index are stored. Alternatively, all images can be contained in a single root directory and the image filenames can be parsed and organized during analysis. In other words, in some embodiments a hierarchical folder structure need not be utilized. Instead, all images can be contained within a single root folder.

As described above, systems may be preferably configured to allow imaging of live cells grown on tissue culture plastic that can be maintained for long lengths of time (days to months) in tissue culture dishes. Accordingly, in some aspects many timepoints may be taken for a given experiment. Updating a file structure such as that presented in FIG. 20, Panel B may be accomplished by any convenient means. In certain aspects, one or more software modules may perform the following tasks for a given file of the type presented in FIG. 20, Panel A. Once the file name is parsed, the software may check whether a directory corresponding to the Experiment Name exists. If it does not exist, the directory is created; otherwise, the system then checks whether a sub-directory corresponding to the fluorescence channel exists. If the sub-directory corresponding to the fluorescence channel does not exist, it is created; otherwise, the system checks whether a sub-directory corresponding to the particular timepoint exists. In most cases, such a directory will not exist, and must be created. Within that sub-directory, the system creates a sub-directory for the given well identified in the file name (e.g., "A1"), and a corresponding sub-directory within that sub-directory corresponding to the montage index number. The file is then moved or copied to that sub-directory, with the process repeated for any other files contained within the user-defined path.

Means for checking whether a directory has already been created, for creating a directory, for renaming files, and/or for moving files are known in the art.

Image Stitching

Figure 21:
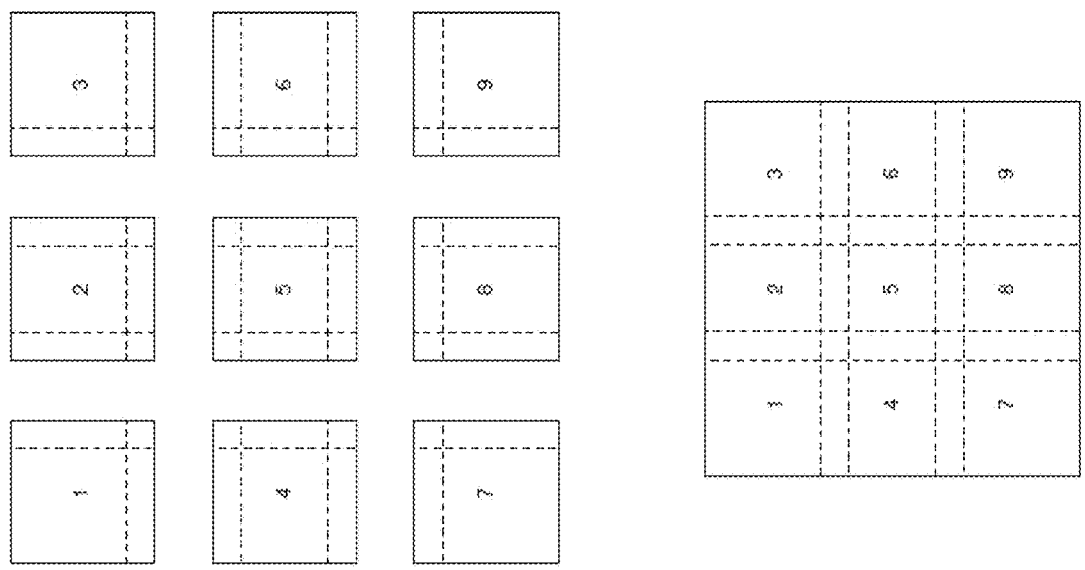
FIG. 21, Panels A-B are illustrations depicting construction of a montage image in connection with some embodiments of the present disclosure. Panel A: Nine images are taken of an individual well of a multi-well plate. For each image, the areas indicated by dashed lines correspond to areas of the image that are substantially identical to those areas indicated in dashed lines of the immediately adjacent images. Panel B: Graphical depiction of a resulting montage image. The nine images from Panel A are overlayed, as indicated by the dashed lines, to produce one image. Panel C provides a montage image of a single well from a 96 multi-well plate. Nine individual images were acquired using a system of the present disclosure and stitched together using a rigid stitching algorithm as described in greater detail herein. Primary cortical neurons were transfected and imaged as described below for FIG. 23. The montage image shows a single well at T=0 using the FITC (green) channel.
Figure 21:
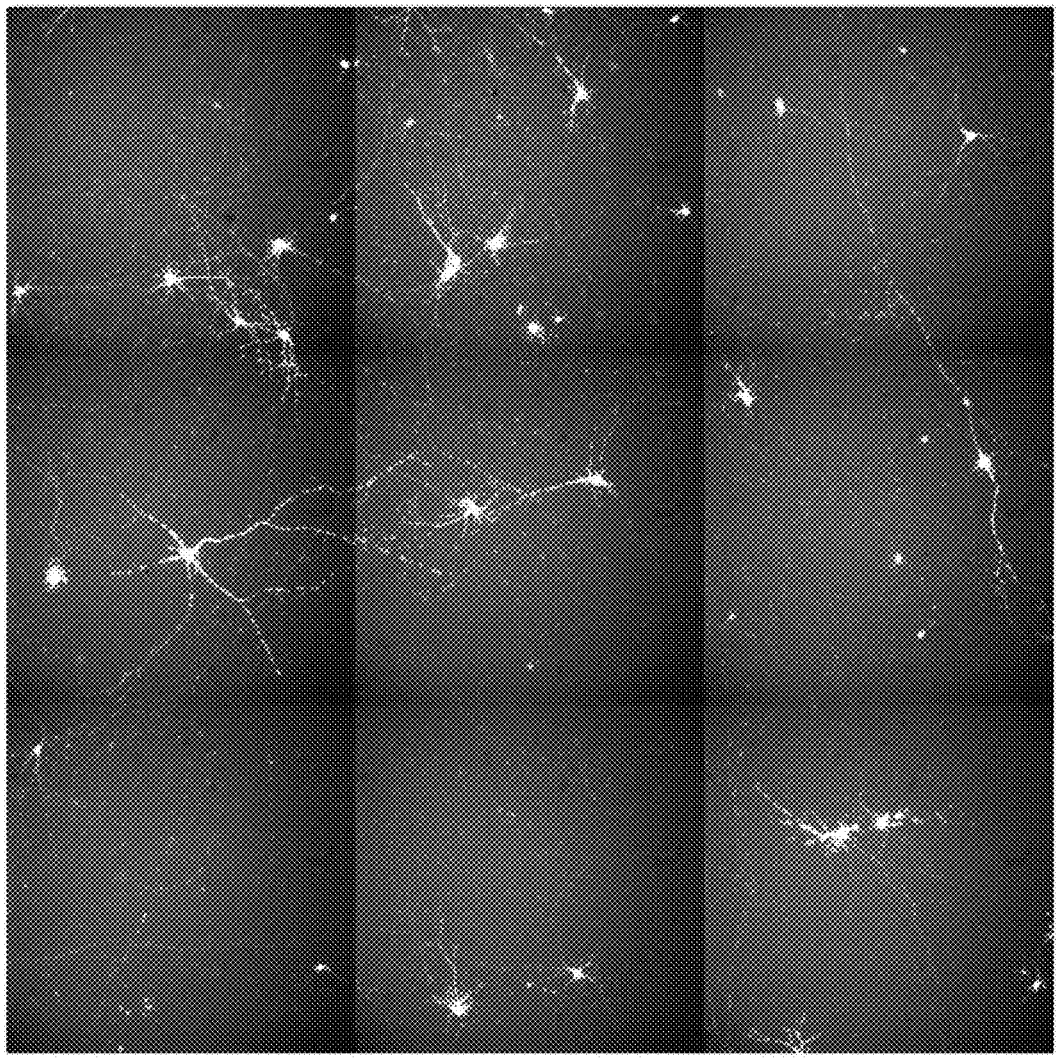

In certain aspects, two or more images may be acquired for a particular sample (e.g., for a particular well). The individual images may be stitched to produce a montage image. FIG. 21, Panels A and B are illustrations depicting general principles of construction of a montage image. Panel A presents nine images taken of an individual well of a multi-well plate. For each image, the areas indicated by dashed lines correspond to areas of the image that are substantially identical to those areas indicated in dashed lines of the immediately adjacent images. These images are then stitched using one or more software modules to produce a montage image, as depicted in Panel B. As is apparent from FIG. 21, Panel B, the resulting montage image contains one or more areas where data from two or more individual images contributed to the resulting montage image.

A variety of stitching software modules may be employed in systems of the present disclosure. In certain aspects, the modules may perform rigid stitching, wherein images are overlaid at specific coordinates. In certain aspects, the modules may perform flexible stitching, in which pixel information at an overlap region is used to adjust the position of the images so as to achieve an improved alignment. Where flexible stitching is employed, a primary cell marker channel (e.g., RFP) may be used to calculate coordinates which may be stored (e.g., in memory). In certain aspects, all subsequent channels (e.g., GFP, etc.) may read this information so there is perfect alignment between the images from different channels.

An examples of stitching algorithms of interest include, but are not limited to, those described in S. Preibisch, et al. (2009) *Bioinformatics,* 25(11):1463-1465; the disclosure of which is incorporated herein by reference. In certain embodiments, software, such as custom (e.g., Pilotscript) or commercially available software, is used to compute starting positions of images within a montage. These images may then be stitched (e.g., using the command "Stitch Collection of Images" using the Stitching plugin in ImageJ). In certain aspects, such stitching is performed where the fusion method is set to linear blending, regression=30; max/avg=2.5, and absolute=3.5.

FIG. 21, Panel C, provides a montage image of a single well from a 96 multi-well plate wherein a rigid stitching algorithm was utilized to form the montage image.

Image Alignment

In certain aspects, a processor may be used to perform an in silico image alignment step before subsequent analysis is performed on the images (e.g., cell tracking, etc.). This may be required because in certain experiments each image is acquired after several hours or more have elapsed (e.g., 12-24 hours or more). When working with biological samples, cells may have moved, died, or changed in intensity between each timepoint. Moreover, additional shifts may be introduced by microscope stage hysteresis.

In certain aspects, pixel intensities are used to map image coordinates by $x=u+\Delta u$. Each timepoint $T(t)$ is aligned to $T(t-1)$, where $t=\{2 \ldots N\}$. Embodiments include the use of an automatic subpixel registration algorithm that minimizes the mean square intensity difference between a reference and a test data set, which can be either images (two-dimensional) or volumes (three-dimensional). In certain aspects, image alignment is performed substantially as described in P. Thévenaz, et al. IEEE Transactions on Image Processing, vol. 7, no. 1, pp. 27-41, January 1998; the disclosure of which is incorporated herein by reference.

Embodiments may include the use of one or more software modules from ImageJ (described in Abramoff, et al., (2004) Biophotonics International 11, 36-42; the disclosure of which is incorporated herein by reference). In certain aspects, the ImageJ plugins StackReg_.jar, MultiStackReg.jar, and/or TurboReg_.jar are used by a software module to perform image alignment.

Cell Identification

Aspects of the subject systems may include one or more software modules to identify particular components (e.g., cells) from images.

Figure 22:
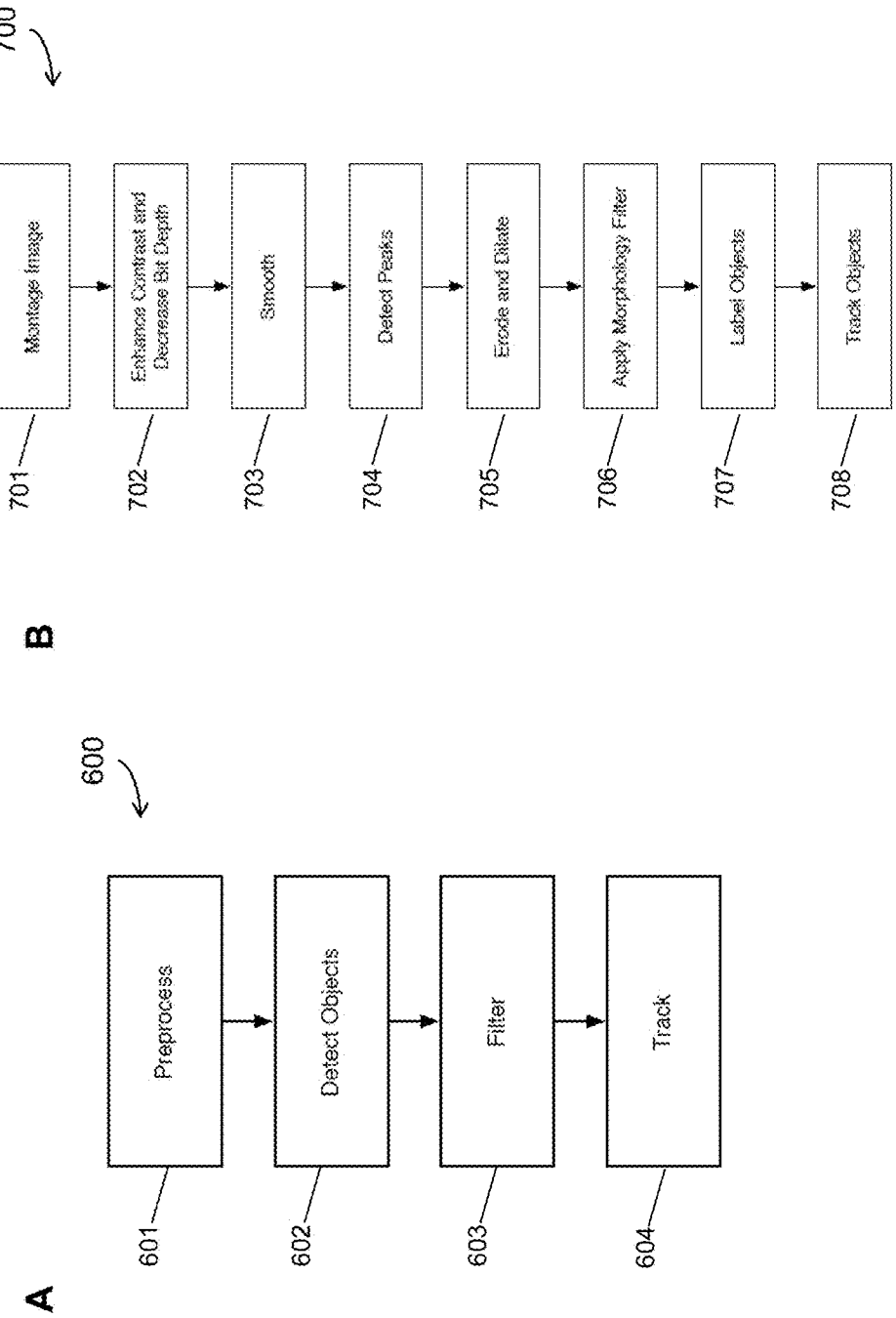
FIG. 22, Panels A-B provide block flow diagrams of methods for labeling and/or tracking objects (e.g., cells) in an image.

A general depiction of the process of labeling objects is presented in FIG. 22, Panel A, which is a block flow diagram of a method for labeling and/or tracking objects (e.g., cells) in an image, such as a montage image. As depicted in this diagram, in the method 600 an image is preprocessed 601. Such preprocessing 601 may be iterative, and/or repeated, such that an image is subjected to one or more preprocessing steps. The preprocessed image is then analyzed for the detection of one or more objects (602). A filtering step 603 may be employed, and objects may be tracked 604 (e.g., tracked over time).

Any convenient preprocessing, object detection, filtering, or tracking methods may be employed in practicing the method 600. For example, in certain aspects of methods for cell identification, the method includes a step of flat-field correction, such as by using and/or obtaining a flat-field reference image, a pseudo flat-field reference image, and/or using a FFT bandpass function. A flat-field reference image may be calculated using any convenient means, such as using median or other percentile metrics or fitting and subtracting a model of the background to the image. Suitable flat-field correction techniques include those described in J A Seibert, et al. *Medical Imaging* 1998: *Physics of Medical Imaging,* 348 (Jul. 24, 1998); the disclosure of which is incorporated herein by reference.

FIG. 22, Panel B depicts a more specific embodiment of such a method 600. In this method 700, the steps of creating a montage image 701, enhancing contrast and decreasing bit depth 702, and smoothing 703 correspond to preprocessing steps 601, using the example of FIG. 22, Panel A. Similarly, the step of detecting peaks 704 corresponds to the step of detecting objects 602. The steps of method 700 of eroding and dilating 705 and applying a morphology filter 706 map to the step of filtering 603. Finally, the steps of method 700 of labeling objects 707 and tracking objects 708 map to the step of tracking 604, using the example of FIG. 22, Panel A.

As depicted in FIG. 22, Panel B, in certain aspects an image, such as a montage image, is first subjected to contrast enhancement and decreased bit depth 702. A smoothing operation 703 may be employed. Next, a peak detection algorithm 704 is used to identify peaks above a user-defined threshold in the image histogram. In certain aspects, the threshold is about 95%, and/or the peak region must be 2 fold greater than surrounding regions. Peaks are defined as an absolute peak and surrounding pixels within a defined range (e.g., all 8 adjacent pixels). Next, the image is eroded and dilated 705 to remove thin objects. For example, objects having a radius of about 10 pixels or less, such as about 5 pixels or less, may be removed.

In certain aspects, a morphology filter 706 is applied, such as a morphology filter that eliminates objects based on area, eccentricity, and/or circularity. After applying a morphology filter 706, the objects may be labeled 707 and tracked 708. Morphology filters may vary depending upon the particular type of sample being investigated, the specific hardware and image acquisition parameters, and other variables known to those of skill in the art. In certain aspects, objects smaller than about 800 to 1000 pixels with 20× magnification on a 1392×1040 px CCD are removed, such as where the sample includes cells such as neurons. Embodiments may also, or instead, utilize a bandpass filter to include or exclude objects, where such a filter that is implemented as a Fourier transform, a difference of Gaussians, or a neurite/distance map.

Circularity is defined using the equation $4\pi(\text{area}/\text{perimeter}^2)$; where a value of 1.0 indicates a perfect circle, and a value of 0.0 indicates an increasingly elongated polygon. For a perfect circle, this number is equal to 1. Since this calculation is done in pixels, the measure will not be very meaningful for very small objects (for example, an object that consists of only one pixel will have both the area and the perimeter equal to 1, so circularity will be $4\pi$, even though the object is relatively close to a circle). As the object gets bigger, the measure improves. For instance, for a circle of radius 2 the area is 21 and the perimeter is 16 (number of border pixels), and the circularity is 1.03.

In certain aspects, objects that have circularity cutoff of 0.8 or higher are retained. In certain aspects, objects that have an eccentricity value above 0.1 (e.g., above 0.2) are retained. In certain aspects, objects having an area of less than about 800 pixels are discarded. Those objects remaining may be labeled.

In certain aspects, one or more filters are employed that are based on dynamic changes within a tracked object over time. For example, rather than employing a set cutoff (e.g., a circularity cutoff), a filter employs a cutoff or range which measures the change between the current value for a feature and one or more prior values. Such a filter may, for instance, be based on one or more features that indicate cell health (e.g., neurites). By measuring dynamic changes, as opposed to static features, such filters may facilitate longitudinal experiments where objects (e.g., individual neurons) are tracked over time.

Embodiments of the systems and methods of the present disclosure include imaging of neurons. In such embodiments, cell identification may involve the characterization of cellular extensions, e.g., neurites, which may be used to provide information about the functional and/or health status of a cell, e.g., a neuron. Such characterization can be used to, e.g., track differences in neurite parameters between conditions, changes in neurite parameters over time, and/or as a segmentation filter to identify neuronal vs. non-neuronal cells. Such embodiments may involve the use of neuron-specific methods which look at cell-specific changes in neurite parameters, and/or image-wide methods which look at how the population of visible neurites, whether from cells on or off the image, change.

Figure 26:
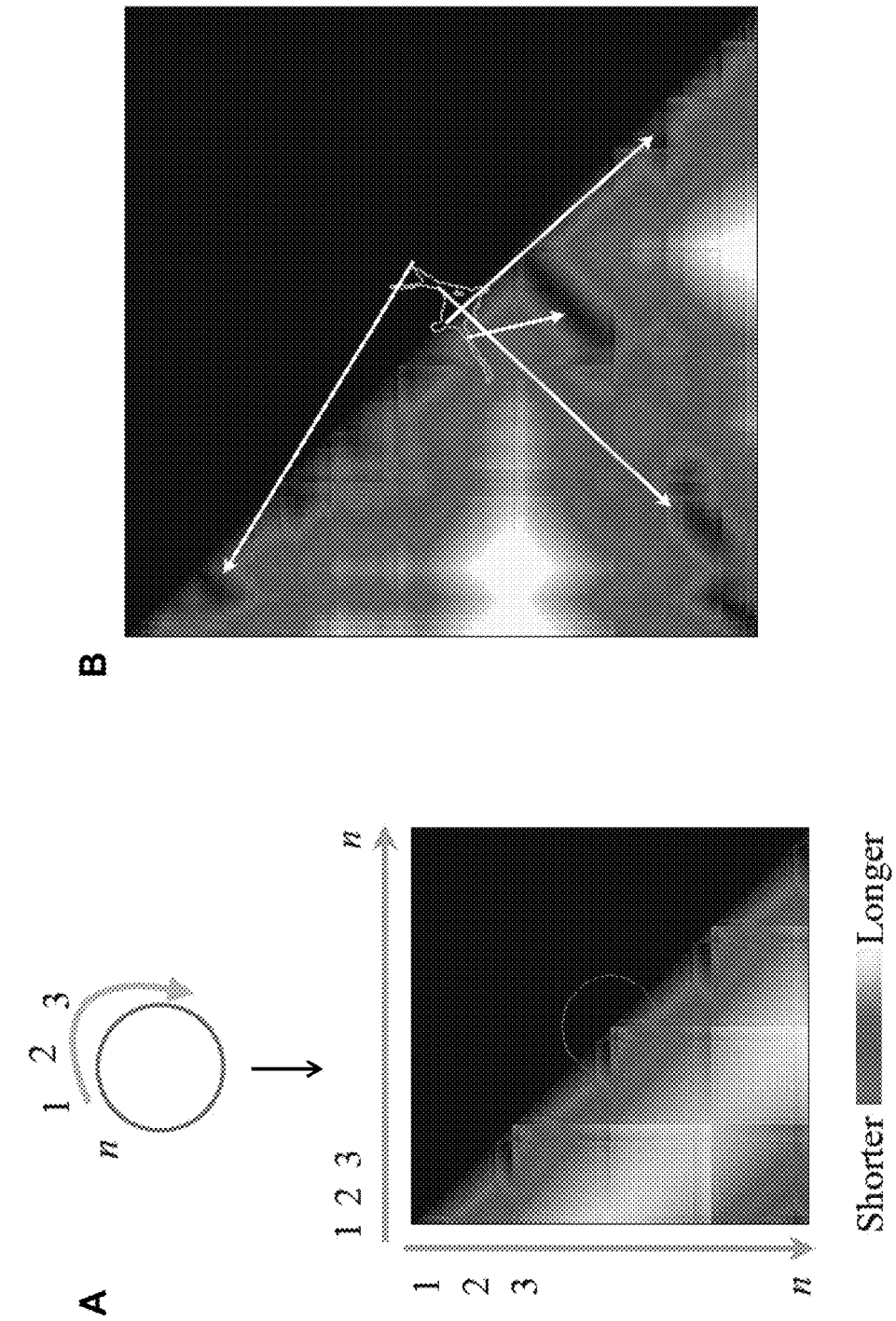
FIG. 26, Panels A-E show automated detection of neurites. Panel A: a distance map is created, where the pixel intensity is equal to the distance between two points on the region of interest (ROI). Darker colors indicate shorter distances. Panel B: distance map showing neurites. The neuron—with neurites—is overlayed in the center of the distance map. Arrows show the mapping between a neurite and the corresponding change in the distance map. In the map, the length of the indentation is equal to the length of the neurite segment, and the pixel intensity equals the width of the neurite segment. Panel C: the initial distance map shown in Panel B includes distances outside of the neuron. In this panel, the distances are restricted to just those distances inside the ROI. Panel D: thresholding intensity on a distance map is thresholding for neurite width, selected between 0-30 pixels (0-10 µm). Panel E: Branching segments can be linked using the distance map; segment ends with matching x or y coordinates are branching.
Figure 26:
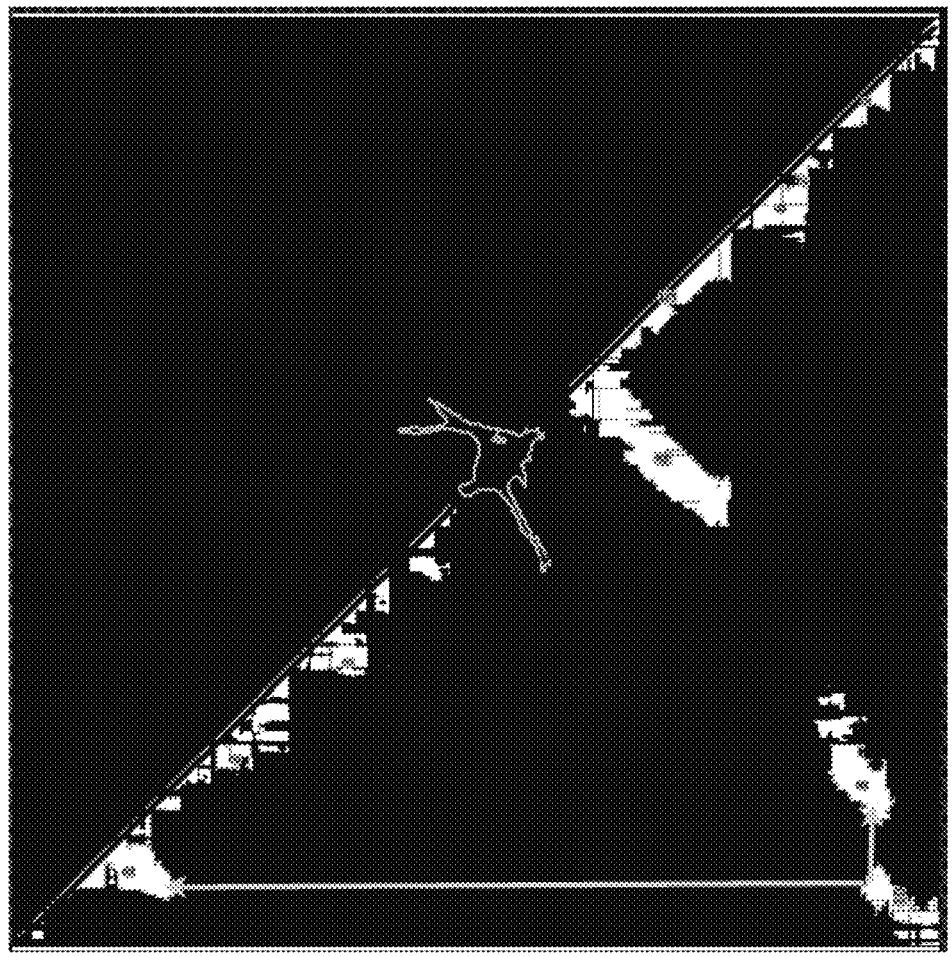

For example, embodiments may include the use of neuron-specific methods. In some aspects, such methods involve a topological analysis of the number, length, and/or width of the branches on a neuron. The topological information is extracted from the set of points which make up the perimeter of the object. For each point, a list of distances to all of the other points along the perimeter is calculated. In some cases, only distances where the length is entirely contained within the object is calculated and the value is left empty or 0 otherwise. This array can be represented as a two dimensional image referred to as a distance map where the x or y coordinates represent the nth point along the perimeter, and the pixel intensity represents the distance from the point #x on the list to point #y on the list. The distance map is symmetric along the diagonal so only half of distances may be calculated and plotted. The distance map analysis thus transforms a morphological analysis into an intensity analysis. Thresholding the image to eliminate all pixels which represent distances greater than 20-30 pixels (~6-10 microns) removes portions of the cell which would be too wide to classify as a neurite. Counting the number of objects which remain after thresholding reflects the number of branches on the neuron. The length of the neurite segment is the length of the "valley" remaining after segmentation, starting with the point closest to the line of diagonal symmetry and ending with the point farthest away. Connections between segments can be determined by finding neurite segments where the endpoint matches vertically or horizontally with another endpoint on a neurite segment. This approach can be used to quantify neurites in an automated fashion (see, e.g., FIG. 26, Panels A-E).

Further, counting the number of neurites in neuronal cultures can be an early and sensitive measure of cell health. Neurite retraction often precedes neuron death when cells are coping with neurodegenerative disease causing proteins. One way to detect neurites with low computational complexity is to quantify the total area of neurites in an image. A line detector may be used to identify pixels in an image that have local structures that represent a line. The determination is based on the second order pixel data (Hessian matrix), which is a measure of local intensity curvature. In certain aspects, such an approach uses the following parameters:

1. Sigma start=1 (approximates expected line width)
2. Sigma step=1 (approximates expected line width)
3. Sigma count=1 (approximates expected line width)
4. Beta1=0.5 (sensitivity to blobness)
5. Beta2=25 (sensitivity to second order structure)

Figure 24:
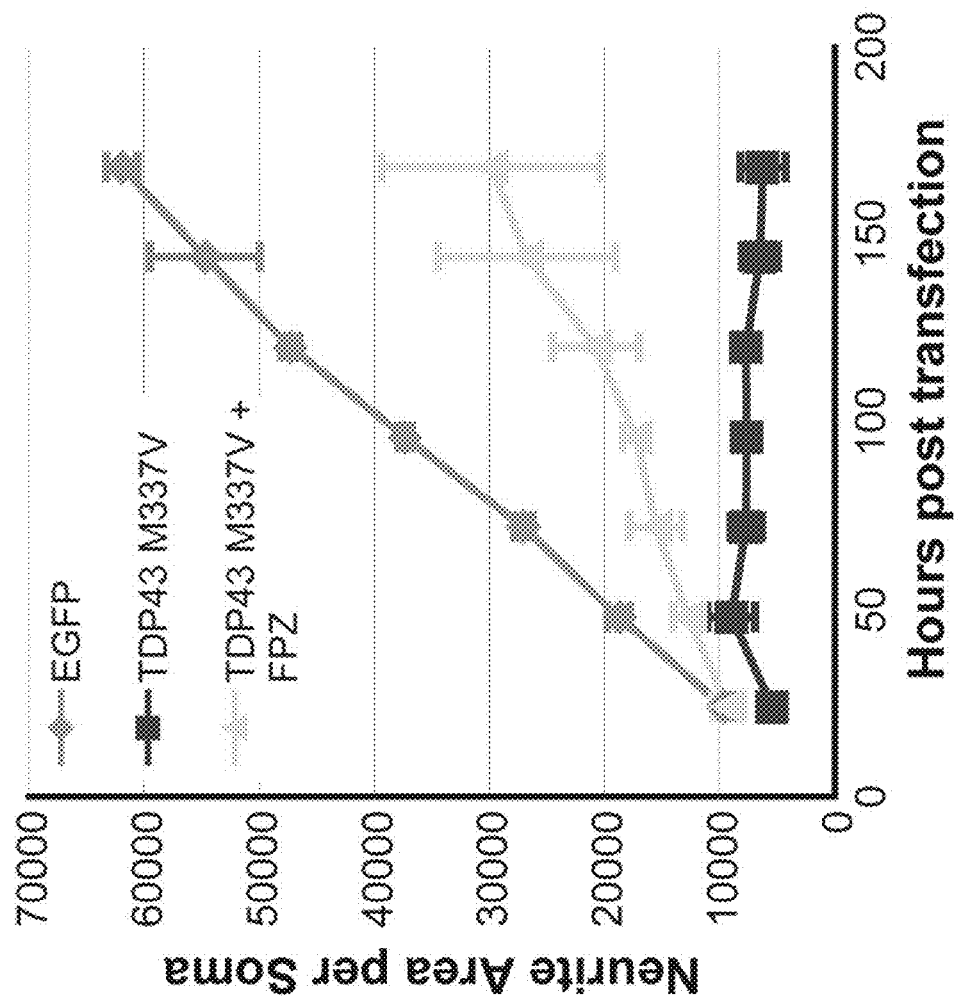
FIG. 24 is a graph showing how autophagy induction mitigates neurite degeneration induced by a disease model of amyotrophic lateral sclerosis (TDP43 M337V). Primary neurons were transfected with GFP as a control or TDP43 M337V. The disease model neurons were treated with fluphenazine (0.1 µM) or vehicle to determine whether autophagy could rescue TDP43 M337V mediated loss of neurites. Images were collected every 24 hours with the robotic microscope and neurites were quantified using automated analysis as described herein.

The output of the line detector is a binary image with pixels that are part of lines having a value of 1 and all other pixels having a value of 0. The pixels of this binary image are then summed to quantify the total area of neurites. For example, FIG. 24 is graph showing autophagy induction mitigates neurite degeneration induced by a disease model of amyotrophic lateral sclerosis (TDP43 M337V). Primary neurons were transfected with GFP as a control or TDP43 M337V. The disease model neurons were treated with fluphenazine (0.1 µM) or vehicle to determine the whether autophagy could rescue the disease model phenotype. Images were collected every 24 hours with the robotic microscope and neurites were quantified using automated analysis as described above.

In certain aspects, one or more of the above steps may be performed using commercially available software, such as the advanced imaging toolbox from Pipeline Pilot (Accelrys), ImageJ, Matlab, Perkin Elmer Velocity, Media Cybernetics ImagePro Plus, Metamorph, and/or Nikon Elements. In other aspects, one or more steps of the process are performed by custom software modules.

Cell Tracking

As describe above, in certain aspects the systems are configured to allow for precise return to and re-imaging of the same field (e.g., the same cell) that has been previously imaged. Accordingly, in certain embodiments cells may be tracked across different time points using one or more software modules.

At a given time point, objects may be identified using the algorithms and/or modules as described above. For a given time point, once objects are identified they may be 'tracked' by comparing the position, intensity, size, circularity, etc. of the object at a prior and/or subsequent time point.

Cell-tracking algorithms can be categorized into a number of different types. For example, the centroid cell-tracking algorithm calculates the center-of-mass (centroid) of the object of interest. It performs best when all objects move in exactly the same way between consecutive frames, relative to each other and irrespective of changes in their shapes and intensities. In contrast, the Gaussian cell-tracking algorithm directly fits Gaussian curves to the intensity profile and performs best when the intensities of the objects are same between consecutive frames, even if their movement is random relative to each other. Another type is a cross-correlation algorithm, which compares an image to a matrix of pixels (user defined) of a successive image. The matrix may be shifted relative to the image in 1-pixel increments. For each increment, a correlation value is calculated that describes how well the values in the matrix match those of the image, and the program determines the shift that yields the maximum correlation value. This algorithm is computationally more intensive than the other two and significantly slows the analysis, depending on the size of the matrix selected.

In certain aspects, cells may be tracked based on a strict overlap, wherein if two segmented objects overlap in consecutive images, then the object in the latter image is relabeled to the same label in the former image. In other aspects, cells are tracked by minimum centroid-to-centroid distance, and/or minimum border-to-border distance. Aspects may include the use of a maximum velocity value, which specifies the maximum allowed displacement for a cell in consecutive images. In various aspects, any of such cell-tracking algorithms described herein may be employed in the systems and methods of the present disclosure.

In certain aspects, objects are tracked between a time point $T_1$ and a later time point $T_2$ by identifying the objects present in the respective images (e.g., using a cell identification software module, as described above). Data recorded for each object present at $T_1$ may be recorded, such as the well number, the object index, the time point, the position, intensity, size, circularity, etc. of the object. Likewise, data recorded for each object present at $T_2$ may be recorded, such as the well number, the object index, the time point, the position, intensity, size, circularity, etc. of the object. Objects present at $T_2$ that were not present at $T_1$ may be handled in a variety of ways. In certain aspects, the newly appearing object may be assigned an object number corresponding to the next highest available number.

Tracking may be facilitated by using one or more commercially available software modules, or custom software modules. In certain aspects, cells may be tracked by using, for example, Pipeline Pilot (Accelrys) and/or ImageJ.

Data Extraction

A number of features may be extracted from the aforementioned images, including morphology features, intensity features, texture features, location features, and the like. In certain aspects, the features that are extracted correspond to a particular object, such as a cell (e.g., a neuron). Embodiments of the systems and methods of the present disclosure also, or instead, include calculating one or more features that take into account one or more neighbors of an object (e.g., neighboring cells), as is described more fully below.

Morphology features of interest include, but are not limited to, area, perimeter, circularity, convex hull, roughness, and topological descriptors. Intensity features of interest include, but are not limited to, mean intensity, intensity order statistics, standard deviation, skewness, and kurtosis. Texture features of interest include, but are not limited to, entropy, neighborhood intensities, homogeneity, and Law's descriptors (e.g., Level, Edge, Spot, Wave, Ripple). Location features of interest include, but are not limited to, centroid, bounding box, and edge touching.

In certain aspects, one or more region shape statistics are extracted, with such region shape statistics of interest including, but not limited to: equivalent diameter (diameter of the circle of the same area); convex area (area of the convex hull); extent (area divided by the area of the bounding box); solidity (area divided by the area of the convex hull); Euler number (number of holes subtracted from the number of connected blobs); form factor (measure of circularity, where circularity is equal to $4\pi(area/perimeter^2)$); nearest neighbor (centroid-centroid); nearest neighbor (boundary-boundary); smallest bounding rectangle parameters, such as orientation (angle between the x-axis and the longer side of the smallest rectangle that contains the whole object), length (longer side of the smallest rectangle that contains the whole object), width (shorter side of the smallest rectangle that contains the whole object), and center (X and Y coordinates of the center of the smallest rectangle that contains the whole object); fitted ellipse parameters (filled or contour), such as eccentricity (measure of ellipse elongation; distance from the center to either focus, divided by the length of major semi-axis), orientation (angle between x-axis and the major axis in radians), major axis length, and minor axis length.

In certain aspects, one or more region pixel intensity statistics are extracted, with such region pixel intensity statistics of interest including, but not limited to, mean; range (difference between the maximum and the minimum values); variance (variance of pixel values); mean absolute deviation (average absolute difference between the pixel values and the mean pixel value); standard deviation (standard deviation of pixel values); skewness of pixel values; kurtosis of pixel values; sum of pixel values; sum squared of pixel values; entropy of pixel values; center of mass (location of the center of mass); mass displacement (distance between the geometric center and the center of mass); spatial moments (spatial moments of orders up to 3); central moments (central moments of orders up to 3); normalized central moments (normalized central moments of orders up to 3); Hu moments (Hu moments of orders up to 3); order statistics, such as intensity order statistics for percentages specified in Order Statistics Percentages, such statistics derived from the co-occurrence matrix (CM) including energy (sum of squared elements of the CM), contrast (measure of contrast between a pixel and its neighbor over the whole object), correlation (measure of how correlated a pixel is to its neighbor over the whole object), homogeneity (measure of closeness of the CM to the CM of a homogeneous region), and entropy (entropy of the CM elements).

Features of interest may be extracted from an individual object and/or a population. Populations of interest include, but are not limited to, populations defined as all objects that are within a certain distance from a specified object. For example, where an object of interest is a cell, the neighbor(s) of that cell can be identified to define a population consisting of the cell of interest, along with its neighbor(s). Accordingly, such an approach facilitates the identification of cell non-autonomous effects by including parameters of neighboring cells as variables in determining a cell's fate. These non-autonomous effects could arise from cell-to-cell interaction such as a neural circuit or the release of molecules from a cell such as growth factors. Depending on the experiment, all or a subset of the cells visible in an image may have neighbor analysis applied. In addition, the cells for which neighbor analysis is applied and the cells which are considered neighbors may be drawn from the same set or from distinct sets. The distinction between the two populations may be based on parameters computed from the images such as inclusion bodies or morphology, or they may be based upon experimental manipulation such as cell-specific reporters or transfection with different markers at two timepoints to label separate populations.

The cells which are considered adjacent can be determined using any convenient method. For example, in a first method, all other cells in the image are ranked by distance from closest to farthest, and a pre-determined number of cells from the top of the list are classified as neighbors. In a second method, all cells within a certain maximum distance and possibly further than a certain minimum distance are classified as neighbors. In a third method, only cells which have physical connections where one part of a cell is in apposition with another cell are classified as neighbors. Apposition can be determined using morphology or through the use of fluorescent markers which localize to cellular junctions. These methods are not exclusive so several may be applied to the same dataset. In all three methods, cells which are within a certain distance of the edge can be excluding from analysis due to incomplete data on their neighbors.

Such neighbor analysis may be used to compute a number of variables. Variables which are used in determining a cell fate in neighbor analysis can include the normally calculated cellular parameters for each neighboring cell as well as aggregate data such as the cumulative, average, or median of any cellular parameter where neighboring cells are defined using one of the above methods. The center of the cell can be determined using at least three different methods. For example, in a first method, the center is defined as the average of the x and y coordinates of all the pixels within the cell. In a second method, the center is defined as the weighted average of all the cell's pixels where the pixel intensity is used as the weight. In a third method, a subcellular region of the cell such as the nucleus is used to calculate the center using either the average or weighted average.

The end result of extraction is typically an extensive set of features, commonly called a feature vector. Data that is extracted may be exported (e.g., as comma-separated values) to programs like Microsoft Excel or statistical packages like R for advanced analysis.

In certain embodiments, such data may be analyzed using one or more machine or statistical learning algorithms to facilitate the identification of relationship(s) between one or more features and a state, such as a disease state. Examples of machine learning algorithms of interest include, but are not limited to, AODE; artificial neural networks; backpropagation; Bayesian statistics; Naive Bayes classifier; Bayesian network; Bayesian knowledge base; Case-based reasoning; Decision trees; Inductive logic programming; Gaussian process regression; Learning Vector Quantization; Instance-based learning; Nearest Neighbor Algorithm; Analogical modeling; Probably approximately correct learning (PAC) learning; Symbolic machine learning algorithms; Sub symbolic machine learning algorithms; Support vector machines; Random Forests; Ensembles of classifiers; Regression analysis; Information fuzzy networks (IFN); Linear classifiers; Fisher's linear discriminant; Logistic regression; Quadratic classifiers; k-nearest neighbor; C4.5; Hidden Markov models; Data clustering; Expectation-maximization algorithm; Self-organizing maps; Radial basis function network; Vector Quantization; Generative topographic map; A priori algorithm; Eclat algorithm; FP-growth algorithm; Hierarchical clustering; Single-linkage clustering; Conceptual clustering; Partitional clustering; K-means algorithm; Fuzzy clustering, dynamic Bayesian networks; and the like.

Exemplary Embodiments

Non-limiting exemplary embodiments of the present disclosure are provided as follows:
1. An imaging system, the system including:
    an imaging device including a sample holder;
    a transport device configured to place a sample in the sample holder;
    a processor in communication with the imaging device and the transport device; and
    memory operably coupled to the processor, wherein the memory includes instructions stored thereon for acquiring an image of the sample, wherein the instructions, when executed by the processor, cause the processor to:
    move the sample via the transport device to the sample holder of the imaging device;
    identify a fiduciary mark on the sample using the imaging device;
    move the sample holder so that the fiduciary mark is in substantially the same position as in a reference image; and
    acquire an image of the sample using the imaging device.
2. The system according to 1, wherein the sample includes a plate.
3. The system according to 1, wherein the plate is a multi-well plate.
4. The system according to 3, wherein the multi-well plate includes about 96 wells or more.
5. The system according to any of 2-4, wherein the plate includes plastic.
6. The system according to 5, wherein the plate is black.
7. The system according to any of 1-6, further including a bulk sample storage subsystem.
8. The system according to 7, wherein the transport device is configured to move the sample from the bulk sample storage subsystem to the sample holder of the imaging device.
9. The system according to 7 or 8, wherein the instructions, when executed by the processor, cause the processor to cause the transport device to move the sample from the bulk sample storage subsystem to the sample holder of the imaging device.
10. The system according to any of 7-9, wherein the transport device is configured to move the sample from the sample holder of the imaging device to the bulk sample storage subsystem.
11. The system according to any of 7-10, wherein the instructions, when executed by the processor, cause the processor to cause the transport device to move the sample from the sample holder of the imaging device to the bulk sample storage subsystem.
12. The system according to any of 7-11, wherein the bulk sample storage subsystem is configured to store 5 or more samples.
13. The system according to any of 7-12, wherein the bulk sample storage subsystem is configured to store 20 or more samples.
14. The system according to any of 7-13, wherein the bulk sample storage subsystem includes a heating element configured to maintain the bulk sample storage subsystem at a specified temperature.
15. The system according to any of 7-14, wherein the bulk sample storage subsystem includes a cooling element configured to maintain the bulk sample storage subsystem at a specified temperature.
16. The system according to any of 7-15, wherein the bulk sample storage subsystem includes a robotic arm configured to transfer a sample from the bulk sample storage subsystem to the transport device.
17. The system according to any of 7-16, wherein the bulk sample storage subsystem includes a robotic arm configured to transfer a sample from the transport device to the bulk sample storage subsystem.
18. The system according to any of 1-17, wherein the transport device is a robotic arm.
19. The system according to 18, wherein the robotic arm includes a plurality of grippers configured to engage the sample.
20. The system according to 19, wherein the grippers exert a lateral pressure on the sample.
21. The system according to 18 or 19, wherein the grippers include adjustable elements for engaging samples of different sizes.
22. The system according to 21, wherein the adjustable elements are manually adjustable.
23. The system according to any of 1-22, further including a sample identification subsystem.
24. The system according to 23, wherein the sample identification subsystem includes a barcode reader configured to read a barcode on the plate.
25. The system according to 23 or 24, wherein the sample identification subsystem is in electronic communication with a processor configured to identify the sample.
26. The system according to 25, wherein the processor is configured to tailor the image acquisition steps for the sample.
27. The system according to any of 1-26, wherein acquiring an image of the sample includes deconvolving a multi-wavelength image into its component wavelengths.
28. The system according to any of 1-27, wherein the imaging device includes an inverted microscope body.
29. The system according to 28, wherein the sample is imaged from below.
30. The system according to any of 1-29, wherein the fiduciary mark is located on the bottom of the sample.
31. The system according to any of 1-30, wherein the sample holder is attached to a microscope stage of the imaging device.
32. The system according to any of 1-31, wherein the sample holder is removable from the imaging device.
33. The system according to any of 1-32, wherein the sample holder includes at least two walls defining a cutout portion, an internal beveled edge, and an internal bottom lip portion.
34. The system according to 33, wherein the internal beveled edge comprises an angle relative to a plane of the bottom lip portion of the sample holder that is from about 85 deg. to about 25 deg.
35. The system according to 34, wherein the angle is from about 70 deg. to about 40 deg.
36. The system according to any of 1-35, wherein the sample holder is sized and shaped to receive a sample having a 127.5 mm×85 mm footprint.
37. The system according to any of 1-36, wherein the sample holder includes a sample receiving area including at least one corner and an actuator configured to bias the sample into the at least one corner.
38. The system according to any of 1-17, wherein the imaging device includes a camera having an exposure of 30 ms or less.
39. The system according to any of 1-38, wherein the imaging device includes a camera having a sensor area of about 170 mm$^2$ to about 250 mm$^2$.
40. The system according to any of 1-39, wherein the camera is an EMCCD camera.
41. The system according to any of 1-40, wherein the imaging device includes a Xenon light source.
42. The system according to any of 1-41, wherein the imaging device includes a filter wheel.
43. The system according to any of 1-42, wherein the memory operably coupled to the processor includes instructions stored thereon that, when executed by the processor, cause the processor to:
    acquire an image of the sample using the imaging device;
    identify a fiduciary mark in the image;

compare the image of the fiduciary mark with a reference image; and move the sample so that the fiduciary mark is in substantially the same position as in the reference image.

44. The system according to 43, wherein the comparison of the image of the fiduciary mark with the reference image includes a scale-invariant feature transform algorithm.

45. The system according to any of 1-44, wherein the imaging device includes an automated focusing component.

46. The system according to any of 1-45, wherein the memory operably coupled to the processor includes instructions stored thereon that, when executed by the processor, cause the processor to perform at least one action selected from:

organize a plurality of images for a particular sample;

stitch two or more images for a particular sample together;

align two or more images of a particular sample;

identify objects within an image of a sample;

track an object through a temporal series of images; and extract data from objects identified within an image.

47. The system according to any of 1-46, including a second processor in communication with the imaging device; and memory operably coupled to the second processor, wherein the memory includes instructions stored thereon for processing an image of the sample, wherein the instructions, when executed by the second processor, cause the second processor to perform at least one action selected from:

organize a plurality of images for a particular sample;

stitch two or more images for a particular sample together;

align two or more images of a particular sample;

identify objects within an image of a sample;

track an object through a temporal series of images; and extract data from objects identified within an image.

48. The system according to any of 1-47, wherein the sample includes biological material.

49. The system according to any of 1-48, wherein the sample includes one or more cells.

50. The system according to 49, wherein the one or more cells are neurons.

51. An imaging system, the system including:

an imaging device; and a robotic arm configured to automatically retrieve a sample from a first surface and place the sample on the imaging device, wherein the system is configured to automatically identify a fiduciary mark on the sample, move the sample so that the fiduciary mark is in substantially the same position as in a reference image, and acquire an image of the sample.

52. The system according to 51, wherein the robotic arm is configured to automatically retrieve the sample from the imaging device and place the sample on a second surface.

53. The system according to 51 or 52, wherein the imaging device includes a sample holder.

54. The system according to any of 51-53, wherein the sample includes a plate.

55. The system according to 54, wherein the plate is a multi-well plate.

56. The system according to 55, wherein the multi-well plate includes about 96 wells or more.

57. The system according to any of 54-56, wherein the plate includes plastic.

58. The system according to 57, wherein the plate is black.

59. The system according to any of 51-58, further including a bulk sample storage subsystem.

60. The system according to 59, wherein the first surface is contained within the bulk sample storage subsystem.

61. The system according to any of 59-60, wherein the bulk sample storage subsystem is configured to store 5 or more samples.

62. The system according to any of 59-61, wherein the bulk sample storage subsystem is configured to store 20 or more samples.

63. The system according to any of 59-62, wherein the bulk sample storage subsystem includes a heating element configured to maintain the bulk sample storage subsystem at a specified temperature.

64. The system according to any of 59-63, wherein the bulk sample storage subsystem includes a cooling element configured to maintain the bulk sample storage subsystem at a specified temperature.

65. The system according to any of 59-64, wherein the bulk sample storage subsystem includes a robotic arm configured to transfer a sample from the bulk sample storage subsystem to the first surface.

66. The system according to any of 51-65, wherein the bulk sample storage subsystem includes a robotic arm configured to transfer a sample from the second surface to the bulk sample storage subsystem.

67. The system according to any of 51-66, wherein the robotic arm includes a plurality of grippers configured to engage the sample.

68. The system according to 67, wherein the grippers exert a lateral pressure on the sample.

69. The system according to 67 or 68, wherein the grippers include adjustable elements for engaging samples of different sizes.

70. The system according to 69, wherein the adjustable elements are manually adjustable.

71. The system according to any of 51-70, further including a sample identification subsystem.

72. The system according to 71, wherein the sample identification subsystem includes a barcode reader configured to read a barcode on the plate.

73. The system according to 71 or 72, wherein the sample identification subsystem is in electronic communication with a processor configured to identify the sample.

74. The system according to 73, wherein the processor is configured to tailor the image acquisition steps for the sample.

75. The system according to any of 51-74, wherein the imaging device includes an inverted microscope body.

76. The system according to 75, wherein the sample is imaged from below.

77. The system according to any of 51-76, wherein the fiduciary mark is located on the bottom of the sample.

78. The system according to any of 53-77, wherein the sample holder is attached to a microscope stage of the imaging device.

79. The system according to any of 53-78, wherein the sample holder is removable from the imaging device.

80. The system according to any of 53-79, wherein the sample holder includes at least two walls defining a cutout portion, an internal beveled edge, and an internal bottom lip portion.

81. The system according to 80, wherein the internal beveled edge includes an angle relative to a plane of the bottom lip portion of the sample holder that is from about 85 deg. to about 25 deg.

82. The system according to 81, wherein the angle is from about 70 deg. to about 40 deg.
83. The system according to any of 53-82, wherein the sample holder is sized and shaped to receive a sample having a 127.5 mm×85 mm footprint.
84. The system according to any of 53-83, wherein the sample holder includes a sample receiving area including at least one corner and an actuator configured to bias the sample into the at least one corner.
85. The system according to any of 51-84, wherein the imaging device includes a camera having an exposure of 30 ms or less.
86. The system according to any of 51-85, wherein the camera is an EMCCD camera.
87. The system according to any of 51-86, wherein the imaging device includes a Xenon light source.
88. The system according to any of 51-87, wherein acquiring an image of the sample includes deconvolving a multi-wavelength image into its component wavelengths.
89. The system according to any of 51-88, further including a processor in communication with the imaging device and the robotic arm device; and memory operably coupled to the processor, wherein the memory operably coupled to the processor includes instructions stored thereon that, when executed by the processor, cause the processor to:
acquire an image of the sample using the imaging device;
identify a fiduciary mark in the image;
compare the image of the fiduciary mark with a reference image; and
move the sample so that the fiduciary mark is in substantially the same position as in the reference image.
90. The system according to 89, wherein the comparison of the image of the fiduciary mark with the reference image includes a scale-invariant feature transform algorithm.
91. The system according to any of 51-90, wherein the imaging device includes an automated focusing component.
92. The system according to any of 51-91, further including a processor in communication with the imaging device; and memory operably coupled to the processor, wherein the memory operably coupled to the processor includes instructions stored thereon that, when executed by the processor, cause the processor to perform at least one action selected from:
organize a plurality of images for a particular sample;
stitch two or more images for a particular sample together;
align two or more images of a particular sample;
identify objects within an image of a sample;
track an object through a temporal series of images; and
extract data from objects identified within an image.
93. The system according to any of 51-92, wherein the sample includes biological material.
94. The system according to any of 51-93, wherein the sample includes one or more cells.
95. The system according to 94, wherein the one or more cells are neurons.
96. A sample holding device, the device including:
two first walls of approximately equal length positioned in opposition, the first walls each defining a cutout portion, an internal beveled edge and an internal bottom lip portion; and
two second walls of approximately equal length positioned in opposition, the second walls each defining an internal beveled edge and an internal bottom lip portion;
wherein each of the two second walls are shorter in length than each of the two first walls, and
wherein the two first walls and the two second walls together define a sample receiving area.
97. The device of 96, wherein the device is so dimensioned as to receive a sample having a 127.5 mm×85 mm footprint:
98. The device according to 96 or 97, wherein the internal beveled edges of the first walls include an angle relative to a plane of the bottom lip portion of the first walls that is from about 85 deg. to about 25 deg.
99. The device according to 98, wherein the angle is from about 70 deg. to about 40 deg.
100. The device according to any of 96-99, wherein the internal beveled edges of the second walls include an angle relative to a plane of the bottom lip portion of the second walls that is from about 85 deg. to about 25 deg.
101. The device according to 100, wherein the angle is from about 70 deg. to about 40 deg.
102. The device according to any of 96-101, wherein the device is configured to attach to an imaging device.
103. The device according to any of 96-102, wherein the device includes an actuator configured to secure a sample placed in the device.
104. The device according to any of 96-103, wherein the device includes aluminum.
105. A computer-implemented method of acquiring an image of a sample, the method including:
moving the sample using a transport device controlled by a processor to a sample holder of an imaging device;
identifying, with the processor, a fiduciary mark on the sample;
aligning, with the processor, the sample holder so that the fiduciary mark is in substantially the same position as in a reference image; and
acquiring, using the imaging device controlled by the processor, an image of the sample.
106. The method according to 105, further including moving the sample, using the transport device controlled by the processor, from the imaging device to a first surface.
107. The method according to 105 or 106, further including processing, with the processor, at least one image of the sample.
108. The method according to 107, wherein processing includes at least one action selected from:
organizing a plurality of images of the sample;
stitching two or more images of the sample together;
aligning two or more images of the sample;
identifying objects within an image of the sample;
tracking an object through a temporal series of images of the sample;
extracting data from objects identified within an image; and
analyzing an image.
109. The method according to 108, wherein stitching two or more images of the sample together includes flexible stitching.
110. The method according to 108, wherein aligning two or more images of the sample includes minimizing the mean square intensity difference between a reference and a test data set.
111. The method according to 108, wherein identifying objects within an image of the sample includes identifying one or more cells.

112. A computer-implemented method of identifying objects in an image of a sample, the method including:
enhancing, with a processor, the image contrast;
decreasing, with the processor, the image bit depth;
smoothing, with the processor, the image;
detecting, with the processor, peaks in the image;
eroding, with the processor, the image;
dilating, with the processor, the image; and
applying, with the processor, a morphology filter to identify objects in the image.

113. The method according to 109, wherein the morphology filter includes a circularity filter and a size filter.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Implementation of an Automated Robotic Microscope System

An automated robotic microscope system was developed that was configured to reduce user intervention relative to existing technologies, and allow for precise return to and re-imaging of the same field (e.g., the same cell) that has been previously imaged.

In this particular embodiment, the system was configured primarily to image cells on multi-well plates, such as a Midsci 96-well plate. Plates containing biological material (e.g., neurons) are stored using an STX44-ICBT 70 deg. C. incubator, equipped with a Transfer Nest™ (LiCONiC Instruments, Liconic US, Inc., Woburn, Mass.). Adjacent to the Transfer Nest™ was positioned a Metrologic MS7120 ORBIT barcode scanner, configured to read barcodes printed on the side of the Midsci plates.

Plates positioned on the Transfer Nest™ could be moved to a plate holder on an imaging device using a KiNEDx KX-300-250 robotic arm (Peak Robotics, Colorado Springs, Colo.), equipped with a plate gripper including first and second gripper arms. Custom extensions were manufactured to allow the robotic arm to interact with the plates (FIGS. 5-6).

The KiNEDx KX-300-250 robotic arm was used to transfer plates to a custom manufactured plate holder. The plate holder was ground from aluminum, having a shape as depicted in FIGS. 7-10. Subsequently, a custom plate holder was manufactured to custom specifications by Applied Scientific Instrumentation (Eugene, Oreg.), with a cutout for an electronic actuator (as depicted in FIGS. 10-17). The plate holder was secured to the stage of a Eclipse Ti-EB inverted research microscope (Nikon Instruments Inc., Melville N.Y.). To the microscope body was also attached an Andor EMCCD iXon3 888 CCD camera (Andor Technology, Belfast, Northern Ireland); Lambda XL light source with an integrated 10-B controller for filter wheel and Smartshutter (Sutter Instrument Co.); and Nikon TiE Perfect Focus System (Nikon Instruments Inc., Melville N.Y.). Optical filters were obtained from Semrock (Rochester, N.Y.).

The system employed several software modules. Scheduling was handled by Green Button Go (BioSero Inc.), using a custom plugin to interface with μ-Manager software (distributed by UCSF, San Francisco, Calif.). Image stitching and alignment modules incorporated ImageJ (described in Abramoff, et al., (2004) Biophotonics International 11, 36-42; the disclosure of which is incorporated herein by reference) plugins Stitching.jar (described in S. Preibisch, et al. (2009) *Bioinformatics,* 25(11):1463-1465; the disclosure of which is incorporated herein by reference), StackReg_.jar, and TurboReg_.jar. Software modules for cell identification and tracking included Pipeline Pilot (Accelrys), ImageJ, and custom software.

Figure 23:
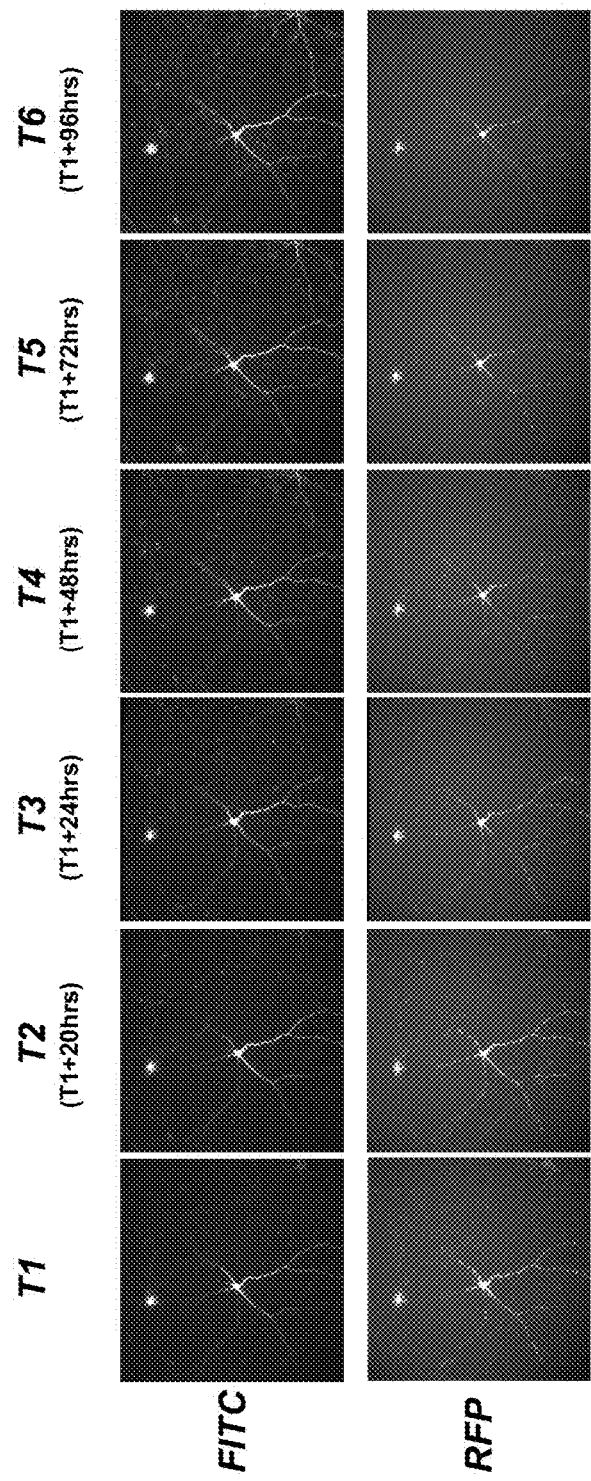
FIG. 23 provides images of one of several primary cortical neurons that were transfected with two plasmids: EGFP and a new mitophagy reporter construct MitoEOS2. The FITC (green) channel (top row) shows the morphology of the neuron which can be used as a mask for determining signal intensity but can also be used for additional image analysis routines such as analysis of neurites as a readout of neuron health. The fluorescence of the MitoEOS2 construct can be irreversibly shifted from green to red upon illumination with blue light. The RFP images (bottom row) show the same neuron shown in the top row of images red-shifted by exposure to a pulse of blue light at the beginning of imaging. The same neuron was imaged eleven times with the first seven images taken every four hours and the last four images separated by twenty four hours. The top and bottom rows are images of the same neuron at T1, T2, T3, T4, T5, and T6, wherein T2 is 20 hr after T1, T3 is 24 hours after T1, T4 is 48 hr after T1, T5 is 72 hr after T1, and T6 is 96 hours after T1. This figure demonstrates the ability of systems of the present disclosure to enable experiments and testing of hypotheses that deal with causality over extended time periods, such as 96 hours or more.

This system allows for precise return to and re-imaging of the same field (e.g., the same cell) that has been previously imaged. This capability enables experiments and testing of hypotheses that deal with causality over time. FIG. 23 provides one such example. This example provides images of one of several primary cortical neurons that were transfected with two plasmids: EGFP and a new mitophagy reporter construct MitoEOS2. The FITC (green) channel (top row) shows the morphology of the neuron which can be used as a mask for determining signal intensity but can also be used for additional image analysis routines such as analysis of neurites as a readout of neuron health. The fluorescence of the MitoEOS2 construct can be irreversibly shifted from green to red upon illumination with blue light. The RFP images (bottom row) show the same neuron shown in in the top row of images red-shifted by exposure to a pulse of blue light at the beginning of imaging. The same neuron was unaged eleven times with the first seven images taken every four hours and the last four images separated by twenty four hours. The top and bottom rows are images of the same neuron at T1, T2, T3, T4, T5, and T6, wherein T2 is 20 hr after T1, T3 is 24 hours after T1, T4 is 48 hr after T1, T5 is 72 hr after T1, and T6 is 96 hours after T1. This figure thus demonstrates the ability of systems of the present disclosure to enable experiments and testing of hypotheses that deal with causality over extended time periods.

Example 2

Selection of Multi-Well Plates

In certain aspects, multi-well plates may be used to grow, store, and/or observe biological materials using systems of the present disclosure. The impact of plate type was analyzed as follows.

A series of plates were acquired for testing, including: Corning 96-well pre-coated with Poly-D-Lysine (PDL) (Cat #3372); BD BioCoat 96-well pre-coated with PDL (Cat #354640); BD BioCoat 96-well pre-coated with PDL-Laminin (L) (Cat #354596); Nunc MicroWell pre-coated with PDL (Cat #152039); Corning Special Optics 96-well (Cat #CLS3614); BD Optilux 96-well (Cat #353948); Nunc Optical Bottom 96-well (Cat #165305); Midsci 96-well (Cat #TP92096); Nunc 96-well Coverglass bottom (Cat #265300); Matek 96-well glass bottom (Cat #PG96G-1.5-5-F—no PDL); Matek 96-well glass bottom (Cat #PG96G-1.5-5-F—with PDL); IBIDI 96-well u-plate (Cat #89626). Corning (Cat #3596) plates were used as control plates. Plates that were not pre-coated were coated with Poly-D-Lysine (50 ug/ml-Millipore Cat #A-003-E) and Laminin (5 ug/ml—Sigma Cat #L2020-1MG). Plates were left overnight at 37° C. with the coating media, followed by two sterile water washes.

All plates were tested at the same time. Plates were coated using the coating media from the same pool and were plated using the neurons also from the same pool.

Survival of primary mouse neurons: To test how well primary mouse neurons survived on each plate relative to control, each well was imaged once in brightfield on DIV 3, 10, 20, 30 and 40. The number of cells in each image was averaged to give the mean and SD for each plate. This was then plotted against the DIV for each plate. Plates that showed significant survival difference for primary mouse neurons when compared to the control plates were: BD BioCoat 96-well pre-coated with PDL (Cat #354640); BD BioCoat 96-well pre-coated with PDL-L (Cat #354596); Corning Special Optics 96-well (Cat #CLS3614); Nunc 96-well Coverglass bottom (Cat #265300); and Matek 96-well glass bottom (Cat #PG96G-1.5-5-F—with PDL).

Number of images in 'perfect' focus: Plates may be imaged with the bottom side facing the optics of a microscope (FIG. 4). Plates were tested to determine which could be imaged in this manner to give images in sharp focus. The number of images in sharp focus was counted by eye for each plate for each DIV image stack. The number of focused images per plate was plotted against the DIV. Plates Corning Special Optics 96-well (Cat #CLS3614); Nunc Optical Bottom 96-well (Cat #165305); Midsci 96-well (Cat #TP92096); Nunc 96-well Coverglass bottom (Cat #265300); Matek 96-well glass bottom (Cat #PG96G-1.5-5-F—no PDL); and Matek 96-well glass bottom (Cat #PG96G-1.5-5-F—with PDL) gave 92+(96%) focused wells in each plate.

Plates in which 95 wells out of the 96 were in sharp focus were Midsci 96-well (Cat #TP92096); Nunc 96-well Coverglass bottom (Cat #265300); Matek 96-well glass bottom (Cat #PG96G-1.5-5-F—no PDL); Matek 96-well glass bottom (Cat #PG96G-1.5-5-F—with PDL).

Media loss at 40 DIV: To measure how much media loss occurred at 40 DIV for each plate, each plate was weighed at DIV 0 and then at DIV 40. Most plates showed a similar media loss and none of them were significantly different from the control plates.

Overall Performance: Plates that showed similar survival to the control plates and had 96% or more focused images per plate were Nunc Optical Bottom 96-well (Cat #165305); Midsci 96-well (Cat #TP92096); and Matek 96-well glass bottom (Cat #PG96G-1.5-5-F—no PDL).

The Midsci 96-well plate was selected for further testing because it gave focused images. 10 Midsci 96-well plates were imaged at DIV 4, 5, 6, 7, 8, 9, 10, 11, 12, 13, 14. The number of focused images per plate was counted, and each had 95-96 wells in sharp focus for each DIV.

Example 3

Neuron Tracking

The following experiment was conducted to select parameters for segmentation algorithms which would allow for automated neuron tracking over time. Several individuals were trained to visually identify neurons in an image of a single well of a multi-well plate. These individuals then selected neurons in each slice of a stack of the morphology channel (i.e., in multiple images of the same well taken over time). The neurons were selected by selecting a point which signified roughly the brightest point of the neuron. Various segmentation algorithms were then compared by determining and comparing the number of neurons detected by the algorithm relative to the number of neurons selected by the human analyzers. This provided an accuracy, false-positive, and false-negative rate for the segmentation algorithms. Parameters for the segmentation algorithms were selected and/or adjusted until a false-negative of less than 10% was achieved. For example, when using a peak detection algorithm to identify peaks in the image histogram, a user-defined threshold of 95% and or a peak region 2 fold greater than surrounding regions was selected. Peaks were defined as an absolute peak and surrounding pixels within a defined range (e.g., all 8 adjacent pixels). Parameters were also adjusted to remove thin objects having a radius of about 10 pixels or less. In addition, a morphology filter having a circularity cutoff of 0.8 or higher was applied to eliminate objects smaller than about 800 to 1000 pixels.

Example 4

Survival Times

The following experiment was conducted to select parameters for algorithms which would allow for automated determination of neuronal survival times. Several individuals were trained to visually identify neurons in an image of a single well of a multi-well plate. These individuals then counted the survival times for neurons using the morphology channel for an experiment with a positive and negative control (i.e. a situation where you would expect to see a survival difference). Hazard curves using survival statistics were generated from these hand-counted experiments. The hazard curves generated using automated segmentation were then compared to the hazard curves from hand-counted experiments to determine how well the algorithms were performing. These trials were used to validate the eccentricity and area filters, and suitable thresholds for such filters, in the automated identification of neurons from an image.

Example 5

Monitoring Mitochondrial Degradation Over Time in Neurons

Primary cortical neurons were transfected with two plasmids, EGFP and a new mitophagy reporter construct MitoEOS2, and cultured in a 96 well plate. The plate was imaged at multiple time points using a robotic microscopy system as described herein. The fluorescence of the MitoEOS2 construct was irreversibly shifted from green to red by exposure to a pulse of blue light prior to imaging. The plate was then imaged eleven times with the first seven images taken every four hours and the last four images separated by twenty-four hours. This is an additional benefit of the disclosed systems in that they allow for adjustment of imaging parameters to capture biological processes that occur over different timescales such as hours or days.

FIG. 23 provides images of one of several primary cortical neurons that were transfected and imaged as described above. The FITC (green) channel (top row) shows the morphology of the neuron which can be used as a mask for determining signal intensity but can also be used for additional image analysis routines such as analysis of neurites as a readout of neuron health. The RFP images (bottom row) show the same neuron shown in in the top row of images red-shifted by exposure to a pulse of blue light at the beginning of imaging. The same neuron was imaged eleven times with the first seven images taken every four hours and the last four images separated by twenty four hours. The top and bottom rows are images of the same neuron at T1, T2, T3, T4, T5, and T6, wherein T2 is 20 hr after T1, T3 is 24 hours after T1, T4 is 48 hr after T1, T5 is 72 hr after T1, and T6 is 96 hours after T1.

As can be seen from the RFP images (bottom row), the signal from the mitophagy reporter construct MitoEOS2 visibly decreases over time indicating mitochondrial degradation. These images demonstrate the ability of the systems disclosed herein to monitor changes in individual cells over time, e.g., during the normal life cycle of the cells or when exposed to one or more experimental conditions. Furthermore, as can be seen from the images in FIG. 23, the disclosed systems allow monitoring and analysis of changes in cell morphology over time such as analysis of neurites as a readout of neuron health.

Example 6

Automated Lipofectamine 2000 Transfection of Primary Neurons

A liquid handling workstation (MICROLAB® STARlet ML 8 96-prep system, available from Hamilton Robotics, Reno Nev.) was incorporated into the automated microscope system described in Example 1, above. As a proof-of-concept, the liquid handling workstation was configured to perform Lipofectamine 2000 transfection of primary neurons as part of the automated system.

The reagents required were obtained from commercial sources and included Opti-Mem, Lipofectamine 2000 Transfection Reagent, DNA, RNAi, NB\KY. Reagents were stored in reservoirs obtained from Seahorse Bioscience (Massachusetts, USA).

The system was configured to perform the following steps:
1. Pick up 96 (1-200 µl) tips.
2. Aspirate 200 µl growth medium from Cell plate and dispense to Cultured medium reservoir
3. Pipette 200 µl per well (total 20 ml) from NB/KY reservoir and dispense to Cell plate (dispensed on side as to not disturb cell monolayer)
4. Tip change, pick up 96 (1-200 µl) tips.
5. Pipette 50 µl per well (total 5 ml) from Opti-MEM reservoir and dispense 25 µl to DNA dilution plate and 25 µl to Lipofectamine dilution plate.
6. Tip change, pick up one column (1-200 µl) tips.
7. Pipette 36 µl from Lipofectamine reservoir and dispense 3 µl sequentially to each column of Lipfectamine dilution plate.
8. Tip change, pick up 96 (1-200 µl) tips
10. Tip change, pick up 96 (1-200 µl) tips.
11. Pipette 1 µl from RNAi reservoir and dispense to DNA dilution plate.
12. Wait 5 min.
13. Pipette 25 µl from DNA dilution plate and dispense drop-wise to Lipofectamine dilution plate.
14. Incubate at least 20 minutes at room temperature.
15. Pipette 50 µl from Lipofectamine dilution plate and dispense drop-wise to Cell plate.
16. Transfer Cell plate off deck to incubator for incubation (20 m to 3 hours).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An imaging system, the system comprising:
   a sample holder comprising at least two walls defining a cutout portion, an internal beveled edge, and an internal bottom lip portion;
   an imaging device; and
   a robotic arm configured to automatically retrieve a sample from a first surface and place the sample on the imaging device,
   wherein the system is configured to:
     automatically identify a fiduciary mark on the sample,
     move the sample so that the fiduciary mark is in substantially the same position as in a reference image, and
     acquire an image of the sample.

2. The system according to claim 1, wherein the robotic arm is configured to automatically retrieve the sample from the imaging device and place the sample on a second surface.

3. The system according to claim 1, wherein the sample comprises a plate.

4. The system according to claim 3, wherein the plate is a multi-well plate.

5. The system according to claim 4, wherein the multi-well plate comprises about 96 wells or more.

6. The system according to claim 3, wherein the plate comprises plastic.

7. The system according to claim 6, wherein the plate is black.

8. The system according to claim 1, further comprising a bulk sample storage subsystem.

9. The system according to claim 8, wherein the first surface is contained within the bulk sample storage subsystem.

10. The system according to claim 8, wherein the bulk sample storage subsystem is configured to store 5 or more samples.

11. The system according to claim 8, wherein the bulk sample storage subsystem is configured to store 20 or more samples.

12. The system according to claim 8, wherein the bulk sample storage subsystem comprises a heating element configured to maintain the bulk sample storage subsystem at a specified temperature.

13. The system according to claim 8, wherein the bulk sample storage subsystem comprises a cooling element configured to maintain the bulk sample storage subsystem at a specified temperature.

14. The system according to claim 8, wherein the bulk sample storage subsystem comprises a robotic arm configured to transfer a sample from the bulk sample storage subsystem to the first surface.

15. The system according to claim 8, wherein the bulk sample storage subsystem comprises a robotic arm configured to transfer a sample from the second surface to the bulk sample storage subsystem.

16. The system according to claim 1, wherein the robotic arm comprises a plurality of grippers configured to engage the sample.

17. The system according to claim 16, wherein the grippers exert a lateral pressure on the sample.

18. The system according to claim 16, wherein the grippers comprise adjustable elements for engaging samples of different sizes.

19. The system according to claim 18, wherein the adjustable elements are manually adjustable.

20. The system according to claim 1, further comprising a sample identification subsystem.

21. The system according to claim 20, wherein the sample identification subsystem comprises a barcode reader configured to read a barcode on the plate.

22. The system according to claim 20 wherein the sample identification subsystem is in electronic communication with a processor configured to identify the sample.

23. The system according to claim 22, wherein the processor is configured to tailor the image acquisition steps for the sample.

24. The system according to claim 1, wherein the imaging device comprises an inverted microscope body.

25. The system according to claim 24, wherein the sample is imaged from below.

26. The system according to claim 1, wherein the fiduciary mark is located on the bottom of the sample.

27. The system according to claim 1, wherein the sample holder is attached to a microscope stage of the imaging device.

28. The system according to claim 1, wherein the sample holder is removable from the imaging device.

29. The system according to claim 1, wherein the internal beveled edge comprises an angle relative to a plane of the bottom lip portion of the sample holder that is from about 85 deg. to about 25 deg.

30. The system according to claim 29, wherein the angle is from about 70 deg. to about 40 deg.

31. The system according to claim 1, wherein the sample holder is sized and shaped to receive a sample having a 127.5 mm×85 mm footprint.

32. The system according to claim 1, wherein the sample holder comprises a sample receiving area comprising at least one corner and an actuator configured to bias the sample into the at least one corner.

33. The system according to claim 1, wherein the imaging device comprises a camera having an exposure of 30 ms or less.

34. The system according to claim 1, wherein the camera is an EMCCD camera.

35. The system according to claim 1, wherein the imaging device comprises a Xenon light source.

36. The system according to claim 1, wherein acquiring an image of the sample comprises deconvolving a multi-wavelength image into its component wavelengths.

37. An imaging system, the system comprising:
a sample holder comprising at least two walls defining a cutout portion, an internal beveled edge, and an internal bottom lip portion;
an imaging device; and
a robotic arm configured to automatically retrieve a sample from a first surface and place the sample on the imaging device,
wherein the system is configured to:
move the sample to an approximate location on a stage of the imaging device,
automatically identify a fiduciary mark on the sample,
move the sample from the approximate location until the fiduciary mark is aligned with a reference image,
acquire a plurality of images of the sample, the plurality of images being a temporal series of images of the sample, and
track an object's movement within the sample via the plurality of images.

* * * * *